United States Patent
Sato et al.

(10) Patent No.: US 8,703,760 B2
(45) Date of Patent: Apr. 22, 2014

(54) ANTIPLATELET AGENT

(75) Inventors: Hiroshi Sato, Osaka (JP); Kazutoshi Yokoyama, Osaka (JP); Kazushi Sato, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 0 days.

(21) Appl. No.: 13/516,952

(22) PCT Filed: Dec. 17, 2010

(86) PCT No.: PCT/JP2010/072743
§ 371 (c)(1),
(2), (4) Date: Jun. 18, 2012

(87) PCT Pub. No.: WO2011/074658
PCT Pub. Date: Jun. 23, 2011

(65) Prior Publication Data
US 2012/0258951 A1   Oct. 11, 2012

(30) Foreign Application Priority Data
Dec. 18, 2009 (JP) ................................ 2009-287946

(51) Int. Cl.
*A61K 31/00* (2006.01)
*A61K 31/535* (2006.01)
*A61K 31/50* (2006.01)
*A61K 31/4965* (2006.01)
*A61K 31/44* (2006.01)

(52) U.S. Cl.
USPC ............ 514/210.21; 514/234.2; 514/248; 514/252.02; 514/252.03; 514/252.04; 514/252.06; 514/255.05; 514/303; 514/333

(58) Field of Classification Search
None
See application file for complete search history.

(56) References Cited

U.S. PATENT DOCUMENTS

| | | | |
|---|---|---|---|
| 4,329,459 A | 5/1982 | McCall | |
| 4,713,381 A | 12/1987 | Ao et al. | |
| 4,985,444 A | 1/1991 | Shiokawa et al. | |
| 5,314,880 A | 5/1994 | Whittaker et al. | |
| 5,344,843 A | 9/1994 | Guthrie et al. | |
| 5,434,150 A | 7/1995 | Austel et al. | |
| 5,741,804 A | 4/1998 | Keenan et al. | |
| 6,030,992 A | 2/2000 | Gitter et al. | |
| 6,841,549 B1 | 1/2005 | Asano et al. | |
| 2003/0199482 A1 | 10/2003 | Seibert et al. | |
| 2004/0002524 A1 | 1/2004 | Chesworth et al. | |
| 2004/0176390 A1 | 9/2004 | Blumberg et al. | |
| 2004/0176396 A1 | 9/2004 | Biftu et al. | |
| 2005/0054631 A1 | 3/2005 | Jiang et al. | |
| 2005/0222197 A1 | 10/2005 | Beight et al. | |
| 2005/0234029 A1 | 10/2005 | Dodic et al. | |
| 2005/0245520 A1 | 11/2005 | Dodic et al. | |
| 2006/0128685 A1 | 6/2006 | Kanaya et al. | |
| 2006/0223850 A1 | 10/2006 | Dube et al. | |
| 2007/0066618 A1 | 3/2007 | Shimojo et al. | |
| 2007/0105899 A1 | 5/2007 | Suzuki et al. | |
| 2007/0254868 A1 | 11/2007 | Lauffer et al. | |
| 2009/0227538 A1 | 9/2009 | Früchtel et al. | |
| 2010/0029657 A1 | 2/2010 | Levin et al. | |
| 2011/0112135 A1 | 5/2011 | Singhaus, Jr. et al. | |
| 2011/0207750 A1 | 8/2011 | Chu et al. | |

FOREIGN PATENT DOCUMENTS

| | | |
|---|---|---|
| EP | 1 853 270 B1 | 4/2010 |
| JP | 63 500031 | 1/1988 |
| JP | 2 243689 | 9/1990 |
| JP | 5 279353 | 10/1993 |
| JP | 5 508153 | 11/1993 |
| JP | 6 25181 | 2/1994 |
| JP | 9-216883 | 8/1997 |
| JP | 9 216883 | 8/1997 |
| JP | 2002-193947 | 7/2002 |
| JP | 2002 193947 | 7/2002 |
| JP | 2005 507854 | 3/2005 |
| JP | 2005 533756 | 11/2005 |
| JP | 2005 534675 | 11/2005 |
| JP | 2005 537291 | 12/2005 |
| JP | 2005 539000 | 12/2005 |

(Continued)

OTHER PUBLICATIONS

Anderson (Chem and Biol 10:787-797, 2003).*

(Continued)

*Primary Examiner* — Craig Ricci
(74) *Attorney, Agent, or Firm* — Oblon, Spivak, McClelland, Maier & Neustadt, L.L.P.

(57) ABSTRACT

The present invention relates to a novel antiplatelet agent and a novel compound which is an active ingredient for the agent. The present invention provides the antiplatelet agent comprising a compound represented by the formula I:

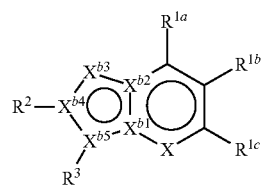

wherein,
X is N, or $CR^{1d}$,
$X^{b1}$-$X^{b5}$ are the same or different, and are nitrogen or carbon,
$R^{1a}$-$R^{1d}$ are the same or different, and are hydrogen, an optionally substituted alkyl, an optionally substituted alkoxy, an optionally substituted alkylthio, an alkenyl, a cycloalkyl, a halogen, cyano, or hydroxyl or optionally substituted by 1 or 2 alkylamino,
$R^2$ is an optionally substituted aryl or an optionally substituted heteroaryl,
$R^3$ is an optionally substituted aryl or an optionally substituted heteroaryl, or
pharmaceutically acceptable salt thereof as an active ingredient.

17 Claims, No Drawings

(56) References Cited

FOREIGN PATENT DOCUMENTS

| | | |
|---|---|---|
| JP | 2006-502164 | 1/2006 |
| JP | 2006 524638 | 11/2006 |
| JP | 2008 509138 | 3/2008 |
| JP | 2008-516962 | 5/2008 |
| JP | 2008 530182 | 8/2008 |
| JP | 2009 533327 | 9/2009 |
| WO | WO 91/19497 | 12/1991 |
| WO | WO 97/31635 | 9/1997 |
| WO | WO 01/02400 | 1/2001 |
| WO | WO 03 000682 | 1/2003 |
| WO | WO 03 045950 | 6/2003 |
| WO | WO 03/045950 A1 | 6/2003 |
| WO | WO 2004/021989 A2 | 3/2004 |
| WO | WO 2005 108370 | 11/2005 |
| WO | WO 2006/017384 A2 | 2/2006 |
| WO | WO 2006/017384 A3 | 2/2006 |
| WO | WO 2006/044509 A2 | 4/2006 |
| WO | WO 2006/044509 A3 | 4/2006 |
| WO | WO 2008 064830 | 6/2008 |
| WO | WO 2009 086123 | 7/2009 |
| WO | WO 2010 051245 | 5/2010 |
| WO | WO 2010/070237 A1 | 6/2010 |

OTHER PUBLICATIONS

Thiel (Nature Biotechnol 2:513-519, 2004).*
Donglai Yang, et al., "A Versatile Method for the Synthesis of Benzimidazoles from O-Nitroanilines and Aldehydes in One Step via a Reductive Cyclization", Synthesis, No. 1, 2005, pp. 47-56.
International Search Report issued on Feb. 22, 2011 in PCT/JP10/072743 filed on Dec. 17, 2010.
Extended Search Report issued May 31, 2013 in European Patent Application No. 10837682.3.
Combined Office Action and Search Report issued Oct. 24, 2013 in Taiwanese Patent Application No. 099144423 (with English Translation of Category of Cited Documents).
Office Action issued Dec. 17, 2013 in Japanese Patent Application No. 2011-546176.

* cited by examiner

ANTIPLATELET AGENT

TECHNICAL FIELD

The present invention relates to a novel antiplatelet agent and a novel compound constituting an active ingredient thereof.

BACKGROUND ART

Glycoprotein Ib (hereafter, GPIb) and glycoprotein VI (hereafter, GPVI) exist on a platelet membrane and play important roles each as a von Willebrand factor (hereafter, vWF) receptor and a collagen receptor in case of forming pathologic thrombus as can be found in a region of arteriosclerosis (non-patent document 1). Collagen is exposed by vascular endothelium damage in case of plaque rupture at the arteriosclerosis region, and a high shearing stress is caused by angiostenosis. The vWF tends to be solid-phased on the exposed collagen, and the platelet accumulates and sticks on the arteriosclerosis region by being connected with the vWF on the solid-phased collagen via the GPI. Thereafter, the GPVI on the platelet combines with the collagen, and the platelet is activated and accumulated to induce pathologic thrombus causing ischemic heart disease such as myocardial infarction, ischemic stroke, peripheral arterial obstruction (non-patent document 2). Haemostasis as a defence mechanism of organisms is formed via activation of the platelet by a tissue factor or a soluble agonist (thromboxane A2 (TXA2), adenosine 2 phosphate (ADP), etc.) released from the extravascular damaged-region. Since aspirin and clopidogrel, as existing medicines, have great influences on the hemostasis mechanism and inhibit the functions of TAXA2 and ADP, they enhance the antithrombotic function as well as the hemorrhagic function (non patent document 3). According to the results of the ATT (Antithrombotic Trialists' Collaboration) which was obtained by the meth-analysis of the Randomized Controlled Trial (RCT) of the preventing effect by the existing antiplatelet agent (single administration of aspirin, ticlopidine, etc.), therapeutic reduction effect of the cardiovascular event by the existing antiplatelet agent is at most 25%, and the degree of satisfaction is not high (non patent document 4). Clinical study of the combined therapy was conducted by using conventional antiplatelet agents (CURE, MATCH, CHARISMA) aiming at a higher therapeutic effect, but it was shown that a risk for bleeding also increases (non patent documents: 5-7).

Heterocyclic compounds such as benzimidazole derivatives are disclosed in patent documents 1-13, and in a non-patent document 8. However, these compounds have not been reported to provide an antiplatelet function, and their characteristics are different from those of the compounds of the present invention. Heterocyclic compounds which have a platelet aggregation inhibitory action are disclosed in the document 14. However, their characteristics are different from those of the compounds of the present invention.

The preparation process of benzimidazole derivatives are disclosed in non-patent document 8.

PRIOR ART DOCUMENTS

Patent Documents

[Patent document 1] WO 1997/031365
[Patent document 2] WO 2001/002400
[Patent document 3] US 20090227538 A
[Patent document 4] US 20050054631 A
[Patent document 5] WO 2006/044509 A
[Patent document 6] US 20040176390 A
[Patent document 7] WO 2010/070237 A
[Patent document 8] US 20050222197 A
[Patent document 9] US 20100029657 A
[Patent document 10] US 20060148805 A
[Patent document 11] US 20090232780 A
[Patent document 12] US 20080132501 A
[Patent document 13] US 20060223849 A
[Patent document 14] US 20060128685 A

Non Patent Documents

[Non patent documents 1] Nature Rev. Drug Discov., 2, 1-15 (2003)
[Non patent documents 2] Thromb. Haemost., 97. 435-443 (2007)
[Non patent documents 3] Platelet and Thrombosis-Basic and Clinic—Edited by Yasuo Ikeda
[Non patent documents 4] Br. Med. J, 324, 71-86 (2002)
[Non patent documents 5] N. Eng. J. Med., 345, 494-502 (2001)
[Non patent documents 6] Lancet, 364, 331-337 (2004)
[Non patent documents 7] N. Eng. J. Med., 354, 1706-1717 (2006)
[Non patent documents 8] Synthesis, 1, 47 (2005)

SUMMARY OF INVENTION

Problem to be Solved by the Invention

The present inventions relate to a novel antiplatelet agent and a novel compound constituting an active ingredient thereof.

Method to Solve the Problem

The inventors of the present invention have made an intensive study to solve the problem mentioned above, and have found that a specified heterocyclic derivative can solve the problem, thus resulting in completion of the present invention.

The present invention relates to a following compound or a pharmaceutically acceptable salt thereof, and/or a use thereof.

The present invention includes the following embodiments.

(1) An antiplatelet agent comprising a compound of formula I:

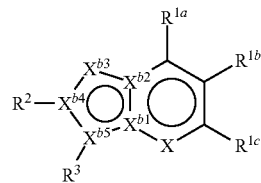

wherein
X is N, or $CR^{1d}$,
$X^{b1}$-$X^{b5}$ are the same or different, and are nitrogen or carbon,
$R^{1a}$-$R^{1d}$ are the same or different, and are hydrogen, an optionally substituted alkyl, an optionally substituted alkoxy, an optionally substituted alkylthio, an alkenyl, a cycloalkyl, a halogen, cyano, hydroxyl, or an amino optionally substituted by 1 or 2 alkyl, $R^2$ is an optionally substituted aryl, or an optionally substituted heteroaryl, $R^3$ is an optionally substituted aryl, or an optionally substituted heteroaryl, provided at least three of $X^{b1}$-$X^{b5}$ are carbon, when $X^{b1}$ is nitrogen, $X^{b2}$, $X^{b4}$ and $X^{b5}$ are carbon, when $X^{b2}$ is nitrogen, $X^{b1}$ and $X^{b4}$ are carbon, and when $X^{b4}$ is nitrogen, $X^{b5}$ is carbon or a pharmaceutically acceptable salt thereof as an active ingredient.

(2) The antiplatelet agent according to (1), wherein $X^{b3}$ is nitrogen.

(3) The antiplatelet agent according to (2), wherein $X^{b4}$ is carbon.

(4) The antiplatelet agent according to (2) or (3), wherein $X^{b2}$ is carbon.

(5) The antiplatelet agent according to (1) comprising a compound of formula Ia:

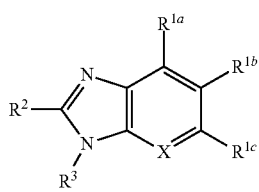

wherein each symbol is the same as described above, or a pharmaceutically acceptable salt thereof as an active ingredient.

(6) The antiplatelet agent according to (1) comprising a compound of formula Ib:

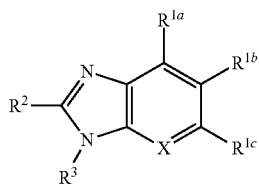

wherein each symbol is the same as described above, or a pharmaceutically acceptable salt thereof as an active ingredient:

(7) The antiplatelet agent according to (1) comprising a compound of formula Ic:

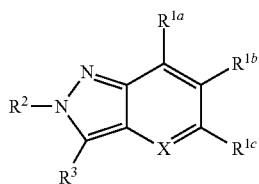

wherein each symbol is the same as described above, or a pharmaceutically acceptable salt thereof as an active ingredient.

(8) The antiplatelet agent according to (1) comprising a compound of formula Id:

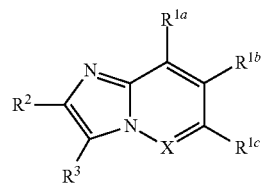

wherein each symbol is the same as described above, or a pharmaceutically acceptable salt thereof as an active ingredient.

(9) The antiplatelet agent according to (1) comprising a compound of formula Ie:

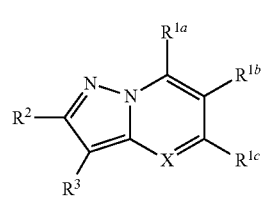

wherein each symbol is the same as described above, or a pharmaceutically acceptable salt thereof as an active ingredient.

(10) The antiplatelet agent according to any one of (1)-(9) wherein $R^{1b}$ is an optionally substituted alkyl, an optionally substituted alkoxy, an optionally substituted alkylthio, an alkenyl, a cycloalkyl, a halogen, cyano, or an amino optionally substituted by 1 or 2 alkyl.

(11) The antiplatelet agent according to any one of (1)-(10) wherein $R^{1a}$ and $R^{1d}$ are hydrogen.

(12) The antiplatelet agent according to any one of (1)-(11) wherein X is N.

(13) The antiplatelet agent according to any one of (1)-(12) wherein substituents of the "optionally substituted aryl" or "optionally substituted heteroaryl" in $R^2$ are the same or different 1-3 groups selected from an optionally substituted alkyl; an optionally substituted alkoxy; an optionally substituted alkylthio; an alkenyl; a halogen; cyano; a carbamoyl optionally substituted by 1 or 2 alkyl; an amino optionally substituted by 1 or 2 alkyl; hydroxyl; an alkanoyl; a cycloalkylcarbonyl; an arylcarbonyl; nitro; an optionally substituted aliphatic heteromonocyclic group; an aryl and a heteroaryl.

(14) The antiplatelet agent according to any one of (1)-(13) wherein substituents of the "optionally substituted aryl" or "optionally substituted heteroaryl" in $R^3$ are the same or different 1-3 groups selected from an optionally substituted alkyl; an optionally substituted alkoxy; an optionally substituted alkylthio; a cycloalkyl; an amino optionally substituted by 1 or 2 alkyl; an aliphatic heteromonocycle and a halogen.

(15) The antiplatelet agent according to any one of (1)-(14) wherein $R^2$ is an optionally substituted heteroary.

(16) The antiplatelet agent according to any one of (1)-(15) wherein $R^3$ is an optionally substituted heteroaryl.

(17) A compound of formula II:

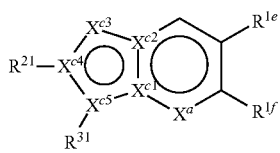

wherein
$X^a$ is N or CH,
$X^{c1}$-$X^{c5}$ are the same or different, and are nitrogen or carbon,
$R^{1e}$ is an alkyl optionally substituted by an aryl or a halogen; an alkoxy optionally substituted by an aryl, a halogen or a cycloalkyl; an alkylthio optionally substituted by an aryl, a halogen or a cycloalkyl; an alkenyl; cyano; a cycloalkyl; a halogen; or an amino optionally substituted by 1 or 2 alkyl,
$R^{1f}$ is hydrogen, an alkyl, an alkoxy, hydroxyl, cyano or a halogen,
$R^{21}$ is an optionally substituted heteroaryl,
$R^{31}$ is an optionally substituted 6-membered heteroaryl, and
at least three of $X^{c1}$-$X^{c5}$ are carbon,
provided
when $X^{c1}$ is nitrogen, $X^{c2}$, $X^{c4}$ and $X^{c5}$ are carbon,
when $X^{c2}$ is nitrogen, $X^{c1}$ and $X^{c4}$ are carbon,
when $X^{c4}$ is nitrogen, $X^{c5}$ is carbon, and
when $X^{c1}$ and $X^{c3}$ are nitrogen, $R^{1e}$ is an alkyl substituted by a halogen or an alkoxy substituted by a halogen,
or a pharmaceutically acceptable salt thereof.

(18) The compound according to (17) wherein $X^{c3}$ is nitrogen or a pharmaceutically acceptable salt thereof.

(19) The compound according to (18) wherein $X^{c4}$ is carbon, or a pharmaceutically acceptable salt thereof.

(20) The compound according to (18) or (19) wherein $X^{c2}$ is carbon, or a pharmaceutically acceptable salt thereof.

(21) The compound according to (17) wherein the compound is represented by the formula IIa:

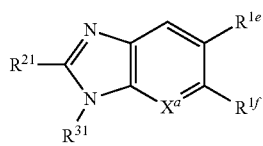

wherein each symbol is the same as described above, or a pharmaceutically acceptable salt thereof.

(22) The compound according to (17) wherein the compound is represented by formula IIb:

wherein each symbol is the same as described above, or a pharmaceutically acceptable salt thereof.

(23) The compound according to (17) wherein the compound is represented by formula IIc:

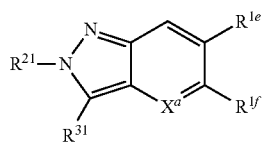

wherein each symbol is the same as described above, or a pharmaceutically acceptable salt thereof.

(24) The compound according to (17) wherein the compound is represented by formula IId:

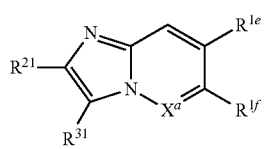

wherein $R^{1e}$ is an alkyl substituted by a halogen or an alkoxy substituted by a halogen, and each other symbol is the same as described above, or
a pharmaceutically acceptable salt thereof

(25) The compound according to (17) wherein the compound is represented by formula IIe:

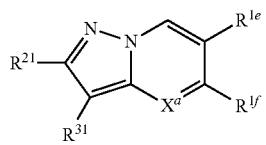

wherein each symbol is the same as described above, or a pharmaceutically acceptable salt thereof.

(26) The compound according to any one of (17)-(25) wherein the substituents of the "optionally substituted heteroaryl" in $R^{21}$ are the same or different 1-3 groups selected from an optionally substituted alkyl; an optionally substituted alkoxy; an optionally substituted alkylthio; an alkenyl; a halogen; cyano; a carbamoyl optionally substituted by 1 or 2 alkyl; an amino optionally substituted by 1 or 2 alkyl; hydroxyl; an alkanoyl; a cycloalkylcarbonyl; an arylcarbonyl; nitro; an optionally substituted aliphatic heteromonocyclic group; an aryl; and a heteroaryl, and
the substituents of the "optionally substituted 6-membered heteroaryl" in $R^{31}$ are the same or different 1-3 groups selected from an optionally substituted alkyl; an optionally substituted alkoxy; an optionally substituted alkylthio; a cycloalkyl; an amino optionally substituted by 1 or 2 alkyl; an aliphatic heteromonocycle; and a halogen, or
a pharmaceutically acceptable salt thereof.

(27) The compound according to any one of (17)-(26) wherein $R^{1e}$ is an alkyl substituted by a halogen or an alkoxy substituted by a halogen, or pharmaceutically acceptable salt thereof.

(28) The compound according to any one of (17)-(27) wherein $R^{1e}$ is trifluoromethyl or trifluoromethoxy, or pharmaceutically acceptable salt thereof.

(29) The compound according to any one of (17)-(28) wherein $R^{1f}$ is hydrogen or pharmaceutically acceptable salt thereof.

(30) The compound according to any one of (17)-(29) wherein the substituents of the "optionally substituted heteroaryl" in $R^{21}$ are the same or different 1-3 groups selected from an optionally substituted alkyl; an optionally substituted alkoxy; a halogen; cyano; a carbamoyl optionally substituted by 1 or 2 alkyl; an amino optionally substituted by 1 or 2 alkyl; hydroxyl; nitro; and an optionally substituted aliphatic heteromonocyclic group, or
a pharmaceutically acceptable salt thereof.

(31) The compound according to any one of (17)-(30) wherein substituents of the "optionally substituted heteroaryl" in $R^{21}$ are the same or different 1-3 groups selected from an alkyl, an alkoxy, a halogen, cyano, a carbamoyl optionally substituted by 1 or 2 alkyl, or nitro, or
pharmaceutically acceptable salt thereof.

(32) The compound according to any one of (17)-(31) wherein substituents of the "optionally substituted heteroaryl" in $R^{21}$ are 1-3 groups selected from an alkyl, a halogen, and cyano, or a pharmaceutically acceptable salt thereof.

(33) The compound according to any one of (17)-(32), wherein substituents of the "optionally substituted 6-membered heteroaryl" in $R^{31}$ are 1-3 groups selected from an alkyl, an alkoxy, a halogen, and an amino optionally substituted by 1 or 2 alkyl, or a pharmaceutically acceptable salt thereof.

(34) The compound according to any one of (17)-(33) wherein $X^a$ is N, or a pharmaceutically acceptable salt thereof.

(35) An antiplatelet agent comprising the compound according to any one of (17)-(34) or a pharmaceutically acceptable salt thereof as an active ingredient.

(36) A medicine for prevention or treatment of ischemic stroke, acute coronary syndrome, microvascular dysfunction, peripheral arterial disease, arteriosclerosis obliterans, ischemic heart disease, thrombotic microangiopathy, or unstable or stable angina, comprising a compound which is an active ingredient of an antiplatelet agent according to any one of (1)-(16) or a compound according to any one of (17)-(34) or a pharmaceutically acceptable salt thereof.

(37) A method of preventing platelet aggregation comprising administrating an effective amount of a compound which is an active ingredient of an antiplatelet agent according to any one of (1)-(16) or a compound according to any one of (17)-(34) or a pharmaceutically acceptable salt thereof.

(38) A method of preventing or treating ischemic stroke, acute coronary syndrome, microvascular dysfunction, peripheral arterial disease, arteriosclerosis obliterans, ischemic heart disease, thrombotic microangiopathy, or unstable or stable angina, comprising administrating an effective amount of a compound which is an active ingredient of an antiplatelet agent according to any one of (1)-(16) or a compound according to any one of (17)-(34) or a pharmaceutically acceptable salt thereof.

(39) The compound for use in preventing platelet aggregation, which is an active ingredient of an antiplatelet agent according to any one of (1)-(16) or a compound according to any one of (17)-(34) or a pharmaceutically acceptable salt thereof.

(40) The compound for use in preventing or treating ischemic stroke, acute coronary syndrome, microvascular dysfunction, peripheral arterial disease, arteriosclerosis obliterans, ischemic heart disease, thrombotic microangiopathy, or unstable or stable angina, which is an active ingredient of an antiplatelet agent according to any one of (1)-(16) or a compound according to any one of (17)-(34) or a pharmaceutically acceptable salt thereof.

(41) The use of the compound which is an active ingredient of an antiplatelet agent according to any one of (1)-(16) or a compound according to any one of (17)-(34) or a pharmaceutically acceptable salt thereof, for the manufacture of an antiplatelet agent.

(42) A use of the compound which is an active ingredient of an antiplatelet agent according to any one of (1)-(16) or a compound according to any one of (17)-(34) or a pharmaceutically acceptable salt thereof, for the manufacture of a medicament for preventing or treating ischemic stroke, acute coronary syndrome, microvascular dysfunction, peripheral arterial disease, arteriosclerosis obliterans, ischemic heart disease, thrombotic microangiopathy, or unstable or stable angina.

In the followings are explained the groups represented by each term and each symbol used herein. Alkyl of the "alkyl" and "alkylthio" is exemplified by $C_{1-6}$, preferably $C_{1-4}$ linear or branched alkyls, in particular, methyl, ethyl, propyl, isopropyl, butyl, isobutyl, 1-methylproplyl, pentyl or hexyl.

The "alkoxy" is exemplified by a $C_{1-6}$, preferably $C_{1-4}$ linear or branched alkoxy, in particular, methoxy, ethoxy, propoxy, isopropoxy, butoxy, iso-butoxy, tert-butoxy, pentyloxy or hexyloxy, The "halogen" is exemplified by fluorine, chlorine, bromine or iodine.

The "alkanoyl" is exemplified by a $C_{1-6}$, preferably $C_{1-4}$ linear or branched alkanoyl, in particular, formyl, acetyl, propionyl, butyryl, pentanoyl or hexanoyl.

The "alkenyl" is exemplified by a $C_{2-6}$, preferably $C_{2-4}$ linear or branched alkenyl, in particular, vinyl, allyl, 1-methyl-2-propenyl, 3-butenyl, 2-pentenyl or 3-hexenyl.

Cycloalkyl in the "cycloalkyl" and "cycloalkylcarbonyl" is exemplified by a $C_{3-8}$, preferably $C_{3-6}$ cycloalkyl, in particular cyclopropyl, cyclobutyl, cyclopentyl or cyclohexyl.

Aryl in the "aryl", "aryloxy" and "arylcarbonyl" is exemplified by a $C_{6-14}$ monocyclic, bicyclic or tricyclic aryl, preferably $C_{6-10}$ monocyclic or bicyclic aryl. In particular, it is exemplified by phenyl, naphthyl, phenanthryl or anthryl.

The "heterocyclic group" is exemplified by an aliphatic heterocyclic group and a heteroaryl containing for example, 1-4 heteroatom(s) selected from nitrogen atom, oxygen atom and sulfur atom, in which optionally, a part or all of 3-12 members may be, as a whole, saturated.

The "aliphatic heterocyclic group" is exemplified by an aliphatic heteromonocyclic group or a heterobicyclic group.

The "aliphatic heteromonocyclic group" is exemplified by an aliphatic heterocyclic group containing 1-4 heteroatom(s) selected from nitrogen atom, oxygen atom and sulfur atom, in which as a whole, a part or all of 3-12 members, preferably 4-7 members are saturated.

The "heterobicyclic group" is exemplified by a heterobicyclic group containing 1-4 heteroatom(s) selected from, for example, nitrogen atom, oxygen atom and sulfur atom, in which as a whole, a part or all of 7-12 members are saturated.

The "heteroaryl" is a 5 to 10-membered aromatic cyclic group which has at least one heteroatom (nitrogen, oxygen or sulfur, etc.) and carbon, and includes a 5 to 6-membered monocyclic group, a 8 to 10-membered bicyclic group formed by condensation of the same or different monocyclic heteroaromatic rings, and a 8 to 10-membered bicyclic group formed by condensation of a monocyclic heteroaromatic ring and benzene.

In the followings are explained preferable embodiments. Substituents of the "optionally substituted alkyl", "optionally substituted alkoxy" and "optionally substituted alkylthio" in $R^{1a}$-$R^{1d}$ are exemplified by an aryl, a halogen, a cycloalkyl, hydroxyl, an alkoxy, and an amino optionally substituted by 1 or 2 alkyl, and further preferably by a cycloalkyl and a halogen, and particularly preferably by a halogen. These substituents may be 1 or plural (e.g., 1-3), and may be the same or different.

$R^{1a}$-$R^{1e}$ is, preferably the same or different, and is an alkyl substituted by a halogen, an alkoxy optionally substituted by a halogen or a cycloalkyl, an alkylthio optionally substituted by a halogen or a cycloalkyl, an alkenyl, a cycloalkyl, a halogen, cyano, hydroxyl, and an amino optionally substituted by 1 or 2 alkyl, etc. In particular, specific examples are difluoromethyl, trifluoromethyl, methoxy, ethoxy, propoxy, isopropoxy, difluoromethoxy, trifluoromethoxy, cyclopropylmethoxy, vinyl, a fluorine atom, a chlorine atom, a bromine atom, cyclopropyl, ethyl and cyano.

$R^{1b}$ and $R^{1e}$ are further preferably exemplified by an alkyl substituted by a halogen, and an alkoxy substituted by a halogen, in particular, 2,2,2-trifluoroethoxy, 1-trifluoromethyl-ethoxy, difluoromethoxy, trifluoromethoxy, difluoromethyl, and trifluoromethyl. Among them, trifluoromethyl and trifluoromethoxy are recited as specifically preferable examples.

$R^{1c}$ and $R^{1f}$ are selected preferably from hydrogen, methyl, methoxy, hydroxyl, cyano, and a chlorine atom, and particularly preferably from hydrogen.

$R^{1a}$ and $R^{1d}$ are, preferably, hydrogen.

Aryl of the "optionally substituted aryl" in $R^2$ is, preferably phenyl or naphthyl, and particularly preferably phenyl.

The "optionally substituted heteroaryl" in $R^2$ or the "optionally substituted heteroaryl" in $R^{21}$ is exemplified by, preferably, a 5 to 6-membered heteroaryl, and particularly preferably, a 6-membered heteroaryl. In particular are recited pyrolyl, imidazolyl, pyrazolyl, thiazolyl, isoxazolyl, oxazolyl, triazolyl, pyrazinyl, pyridazinyl, pyrimidyl, pyridyl, quinolyl, preferably, pyrazolyl, thiazolyl, isoxazolyl, oxazolyl, pyrazinyl, pyridazinyl, pyrimidyl and pyridyl, and particularly preferably, pyridyl and pyrazinyl.

Substituents of "optionally substituted heteroaryl" and "optionally substituted aryl" in $R^2$, and "optionally substituted heteroaryl" in $R^{21}$ are the same or different, and exemplified by, preferably, an optionally-substituted alkyl; an optionally-substituted alkoxy; an optionally-substituted alkylthio; an alkenyl; a halogen; cyano; a carbamoyl optionally-substituted by 1 or 2 alkyl; an amino optionally-substituted by 1 or 2 alkyl; hydroxyl; nitro; and an optionally-substituted aliphatic heteromonocyclic group, and further preferably, an alkyl, an alkoxy, a halogen, cyano, carbamoyl and nitro, and particularly preferably, cyano and a halogen. In particular, they are the same or different, and are methyl, ethyl, vinyl, propenyl, methoxy, methylthio, a fluorine atom, a chlorine atom, a bromine atom, pyrrolidinyl, hydroxypyrrolidinyl, dimethylaminopyrrolidinyl, methoxy-pyrrolidinyl, oxopyrrolidinyl, methoxymethyl-pyrrolidinyl, morpholyl, piperidinyl, methylpiperazinyl, methoxyazetidil, amino, methylamino, dimethylamino, hydroxyl, hydroxymethyl, cyano, nitro and carbamoyl. These substituents may be one or in plural (e.g., 1-3), and the same or different.

When the "optionally substituted heteroaryl" in $R^2$ and $R^{21}$ is a 6-membered monocyclic heteroaryl, the substituents thereof are preferably the same or different, and are an alkyl, an alkoxy, a halogen, cyano, a carbamoyl and nitro, and particularly preferably, fluorine and cyano. These substituents may be 1 or in plural (e.g., 1-3), and the same or different.

When the "optionally substituted heteroaryl" in $R^2$ and $R^{21}$ is a 5-membered monocyclic heteroaryl, their substituents are the same or different and preferably exemplified by an alkyl.

The substituents of the "optionally substituted heteroaryl" and "optionally substituted aryl" in $R^2$, and the substituents of the "optionally substituted alkyl", "optionally substituted alkoxy" and "optionally substituted alkylthio" in the substituents of the "optionally substituted heteroaryl" in $R^{21}$ are, for example, an alkoxy; a halogen; hydroxyl; an amino optionally-substituted by 1 or 2 alkyl, and preferably, an alkoxy; a halogen; hydroxyl; an amino optionally-substituted by 1 or 2 alkyl. These substituents may be 1 or plural (e.g., 1-3), and the same or different.

Substituents in the "optionally substituted aliphatic heteromonocyclic group", which is a substituent of the "optionally substituted heteroaryl" and "optionally substituted aryl" in $R^2$ and "optionally substituted heteroaryl" in $R^{21}$, are exemplified by, an alkyl optionally substituted by hydroxyl or an alkoxy; an alkoxy; an amino optionally-substituted by 1 or 2 alkyl; and oxo.

The "optionally substituted aliphatic heteromonocyclic group" as a substituent of the "optionally substituted heteroaryl" and the "optionally substituted aryl" in $R^2$ and of the "optionally substituted heteroaryl" in $R^{21}$ are exemplified by, in particular, pyrrolidyl, morpholinyl, piperidyl or piperazyl.

A preferable example of $R^2$ and $R^{21}$ is a group represented by the formula:

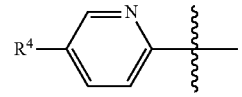

wherein $R^4$ is an alkyl, an alkoxy, a halogen, cyano, a carbamoyl or nitro.

$R^4$ is, particularly preferably, fluorine or cyano.

Aryl of the "optionally substituted aryl" in $R^3$ is, preferably, phenyl or naphthyl, in particular preferably, phenyl.

Heteroaryl of the "optionally substituted heteroaryl" in $R^3$ is exemplified by, preferably, a monocyclic heteroaryl, in particular preferably, a 6-membered heteroaryl. In particular, indole, pyridyl, pyrazinyl, pyrimidyl and pyridazinyl are recited, and preferably, pyridyl, pyrazinyl, pyrimidyl and pyridazinyl are recited.

Heteroaryl of the "optionally substituted 6-membered heteroaryl" in $R^{31}$ is exemplified, in particular, by pyridyl, pyrazinyl, pyrimidyl and pyridazinyl, and preferably, by pyridyl, pyrazinyl and pyridazinyl, and especially, by pyridyl and pyridazinyl.

Substituents of "optionally substituted alkyl", "optionally substituted alkoxy" and "optionally substituted alkylthio" which are substituents of "optionally substituted heteroaryl" and "optionally substituted aryl" in $R^3$ and of "optionally substituted 6-membered heteroaryl" in $R^{31}$ are exemplified, by a halogen; hydroxyl; an amino optionally substituted by 1 or 2 alkyl, and these substituents may be 1 or plural (e.g., 1-3), and the same or different.

Substituents of the "optionally substituted heteroaryl" and "optionally substituted aryl" in $R^3$ and of the "optionally substituted 6-membered heteroaryl" in $R^{31}$ are exemplified, preferably, by an alkyl; an alkoxy; an alkylthio; a cycloalkyl; an amino optionally-substituted by 1 or 2 alkyl; an aliphatic heteromonocycle; and a halogen, in particular preferably, by an alkyl; an alkoxy; a halogen; and an amino optionally substituted by 1 or 2 alkyl. In particular are recited methyl, ethyl, methoxy, ethoxy, methylthio, methylamino, dimethylamino, pyrrolidinyl, cyclopropyl, a fluorine atom, and a chlorine atom, and preferably, methyl, ethyl, methoxy, methylamino, and dimethylamino. These substituent may be 1 or plural (e.g., 1-3), and may be the same or different.

A substituting position of the substituents of the "optionally substituted heteroaryl" and "optionally substituted aryl" in $R^3$ and of the "optionally substituted 6-membered heteroaryl" in $R^{31}$ is, preferably, in para-position toward a benzimidazole ring or an imidazopyridine ring.

A preferable example of $R^3$ or $R^{31}$ is a group represented by the formula:

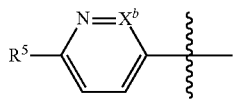

wherein $X^b$ is N or CH, and $R^5$ is an alkyl; an alkoxy; an amino optionally substituted by 1 or 2 alkyl; and a halogen.

Examples of the compounds represented by formulae I and II, or pharmaceutically acceptable salts thereof are the compounds recited in the Examples or pharmaceutically acceptable salts thereof, and preferably selected from 1-(6-methoxypyridazin-3-yl)-2-pyridin-2-yl-5-(trifluoromethyl)-1H-benzimidazole (Example 1);
2-(6-fluoropyridin-2-yl)-1-(6-methoxypyridazin-3-yl)-5-(trifluoromethyl)-1H-benzimidazole (Example 2);
1-(6-methoxypyridazin-3-yl)-2-pyridin-2-yl-5-(trifluoromethoxy)-1H-benzimidazole (Example 3);
2-(5-fluoropyridin-2-yl)-3-(6-methoxypyridin-3-yl)-6-(trifluoromethyl)-3H-imidazo[4,5-b]pyridine (Example 4);
N-methyl-5-[2-pyridin-2-yl-6-(trifluoromethyl)-3H-imidazo[4,5-b]pyridin-3-yl]pyridin-2-amine (Example 5);
N,N-dimethyl-5-[2-pyridin-2-yl-6-(trifluoromethyl)-3H-imidazo[4,5-b]pyridin-3-yl]pyridin-2-amine (Example 6);
6-[1-(6-methoxypyridazin-3-yl)-5-(trifluoromethyl)-1H-benzimidazole-2-yl]nicotinonitrile (Example 7);
5-[3-(6-methoxypyridin-3-yl)-6-(trifluoromethyl)-3H-imidazo[4,5-b]pyridin-2-yl]pyrazine-2-carbonitrile (Example 8);
2-(6-methoxypyridazin-3-yl)-1-(6-methoxypyridin-3-yl)-5-(trifluoromethyl)-1H-benzimidazole (Example 9);
3-(6-methoxypyridin-3-yl)-2-(1H-pyrrol-2-yl)-6-(trifluoromethyl)-3H-imidazo[4,5-b]pyridine (Example 10);
2-(1H-imidazol-4-yl)-3-(6-methoxypyridin-3-yl)-6-(trifluoromethyl)-3H-imidazo[4,5-b]pyridine (Example 11);
1,2-dipyridin-2-yl-5-(trifluoromethyl)-1H-benzimidazole (Example 12);
3-(6-methoxypyridin-3-yl)-2-pyridin-2-yl-6-(trifluoromethyl)-3H-imidazo[4,5-b]pyridine (Example 13);
1-(6-methoxypyridin-3-yl)-2-pyridin-2-yl-5-(trifluoromethyl)-1H-benzimidazole (Example 14);
1-(6-methoxypyridazin-3-yl)-2-(1-methyl-1H-pyrazol-4-yl)-5-(trifluoromethyl)-1H-benzimidazole (Example 15);
5-ethyl-1-(6-methoxypyridin-3-yl)-2-pyridin-2-yl-1H-benzimidazole (Example 17);
1-(6-methoxypyridin-3-yl)-2-phenyl-5-(trifluoromethyl)-1H-benzimidazole (Example 18);
2-(5-bromopyridin-2-yl)-1-(6-methoxypyridin-3-yl)-5-(trifluoromethyl)-1H-benzimidazole (Example 20);
2-(5-fluoropyridin-2-yl)-1-(6-methoxypyridin-3-yl)-5-(trifluoromethyl)-1H-benzimidazole (Example 21);
1,2-bis(6-methoxypyridin-3-yl)-5-(trifluoromethyl)-1H-benzimidazole (Example 24);
5-cyclopropyl-1-(6-methoxypyridin-3-yl)-2-pyridin-2-yl-1H-benzimidazole (Example 27);
5-(cyclopropylmethoxy)-1-(6-methoxypyridin-3-yl)-2-pyridin-2-yl-1H-benzimidazole (Example 31);
2-(5-bromopyridin-2-yl)-1-(6-methoxypyridazin-3-yl)-5-(trifluoromethyl)-1H-benzimidazole (Example 35);
2-(5-chloropyridin-2-yl)-1-(6-methoxypyridin-3-yl)-5-(trifluoromethyl)-1H-benzimidazole (Example 36);
1-(6-methoxypyridin-3-yl)-2-pyridin-2-yl-5-(trifluoromethoxy)-1H-benzimidazole (Example 40);
1-(6-methoxypyridazin-3-yl)-2-(1-methyl-1H-pyrazol-3-yl)-5-(trifluoromethyl)-1H-benzimidazole (Example 52);
1-(6-methoxypyridazin-3-yl)-2-(5-nitropyridin-2-yl)-5-(trifluoromethyl)-1H-benzimidazole (Example 53);
1-(6-methoxypyridazin-3-yl)-2-(1,3-thiazol-2-yl)-5-(trifluoromethyl)-1H-benzimidazole (Example 54);
6-chloro-1-(6-methoxypyridin-3-yl)-2-pyridin-2-yl-5-(trifluoromethyl)-1H-benzimidazole (Example 55);
2-(5-ethylpyridin-2-yl)-1-(6-methoxypyridazin-3-yl)-5-(trifluoromethyl)-1H-benzimidazole (Example 56);
1-(6-methoxypyridazin-3-yl)-2-(4-methylpyridin-2-yl)-5-(trifluoromethyl)-1H-benzimidazole (Example 58);
2-(5-fluoropyridin-2-yl)-1-(6-methoxypyridazin-3-yl)-5-(trifluoromethyl)-1H-benzimidazole (Example 62);
1-[6-(methylthio)pyridazin-3-yl]-2-pyridin-2-yl-5-(trifluoromethyl)-1H-benzimidazole (Example 67);
2-(5-fluoropyridin-2-yl)-1-(6-methoxypyridazin-3-yl)-5-(trifluoromethoxy)-1H-benzimidazole (Example 71);
2-(5-methylisoxazol-3-yl)-1-(6-methoxypyridazin-3-yl)-5-(trifluoromethyl)-1H-benzimidazole (Example 72);
3-(6-methoxypyridin-3-yl)-2-(1-methyl-1H-pyrazol-3-yl)-6-(trifluoromethyl)-3H-imidazo[4,5-b]pyridine (Example 73);
2-(4-bromopyridin-2-yl)-1-(6-methoxypyridazin-3-yl)-5-(trifluoromethyl)-1H-benzimidazole (Example 75);
2-[1-(6-methoxypyridazin-3-yl)-5-(trifluoromethyl)-1H-benzimidazole-2-yl]nicotinonitrile (Example 81);
1-(6-methoxypyridazin-3-yl)-2-(1,3-oxazol-4-yl)-5-(trifluoromethyl)-1H-benzimidazole (Example 88);
1-(6-methoxypyridazin-3-yl)-2-(1,3-thiazol-4-yl)-5-(trifluoromethyl)-1H-benzimidazole (Example 89);
1-(6-methoxypyridazin-3-yl)-2-(5-methylpyrazine-2-yl)-5-(trifluoromethyl)-1H-benzimidazole (Example 90);
1-(6-methoxypyridazin-3-yl)-2-(2-methyl-1,3-thiazol-4-yl)-5-(trifluoromethyl)-1H-benzimidazole (Example 94);
3-(6-methoxypyridin-3-yl)-2-(1,3-oxazol-4-yl)-6-(trifluoromethyl)-3H-imidazo[4,5-b]pyridine (Example 107);
3-(6-methoxypyridin-3-yl)-2-(5-methylisoxazol-3-yl)-6-(trifluoromethyl)-3H-imidazo[4,5-b]pyridine (Example 108);
3-(6-methoxypyridin-3-yl)-2-(1,3-thiazol-4-yl)-6-(trifluoromethyl)-3H-imidazo[4,5-b]pyridine (Example 109);
3-(6-methoxypyridin-3-yl)-2-(2-methyl-1,3-thiazol-4-yl)-6-(trifluoromethyl)-3H-imidazo[4,5-b]pyridine (Example 110);
3-(6-methylpyridin-3-yl)-2-pyridin-2-yl-6-(trifluoromethyl)-3H-imidazo[4,5-b]pyridine (Example 118);
3-(6-methoxypyridin-3-yl)-2-(2-methyl-1,3-oxazol-4-yl)-6-(trifluoromethyl)-3H-imidazo[4,5-b]pyridine (Example 122);
3-(5-methoxypyrazine-2-yl)-2-pyridin-2-yl-6-(trifluoromethyl)-3H-imidazo[4,5-b]pyridine (Example 125);
3-(6-methoxypyridin-3-yl)-2-(5-methyl-1,3-oxazol-4-yl)-6-(trifluoromethyl)-3H-imidazo[4,5-b]pyridine (Example 126);
6-[3-(6-methylpyridin-3-yl)-6-(trifluoromethyl)-3H-imidazo[4,5-b]pyridin-2-yl]nicotinonitrile (Example 130);

1-(6-methoxypyridazin-3-yl)-2-(2-methyl-1,3-oxazol-4-yl)-5-(trifluoromethyl)-1H-benzimidazole (Example 139);
2-(5-fluoropyridin-2-yl)-3-(5-methoxypyrazine-2-yl)-6-(trifluoromethyl)-3H-imidazo[4,5-b]pyridine (Example 144);
6-isopropoxy-3-(6-methoxypyridin-3-yl)-2-pyridin-2-yl-3H-imidazo[4,5-b]pyridine (Example 145);
6-(difluoromethoxy)-3-(6-methoxypyridin-3-yl)-2-pyridin-2-yl-3H-imidazo[4,5-b]pyridine (Example 146);
3-(6-methoxypyridin-3-yl)-2-pyridin-2-yl-6-(trifluoromethoxy)-3H-imidazo[4,5-b]pyridine (Example 147);
3-(5-methoxypyrazine-2-yl)-2-(1,3-thiazol-4-yl)-6-(trifluoromethyl)-3H-imidazo[4,5-b]pyridine (Example 148);
5-[2-(5-fluoropyridin-2-yl)-6-(trifluoromethyl)-3H-imidazo[4,5-b]pyridin-3-yl]-N-methylpyridin-2-amine (Example 149);
6-{3-[6-(methylamino)pyridin-3-yl]-6-(trifluoromethyl)-3H-imidazo[4,5-b]pyridin-2-yl}nicotinonitrile (Example 150);
3-(5-methoxypyrazine-2-yl)-2-(1,3-oxazol-4-yl)-6-(trifluoromethyl)-3H-imidazo[4,5-b]pyridine (Example 151);
3-(5-methoxypyrazine-2-yl)-2-(2-methyl-1,3-oxazol-4-yl)-(trifluoromethyl)-3H-imidazo[4,5-b]pyridine (Example 152);
3-(5-methoxypyrazine-2-yl)-2-(1-methyl-1H-pyrazol-3-yl)-6-(trifluoromethyl)-3H-imidazo[4,5-b]pyridine (Example 153);
3-(5-methoxypyrazine-2-yl)-2-(5-methylisoxazol-3-yl)-6-(trifluoromethyl)-3H-imidazo[4,5-b]pyridine (Example 154);
1-(6-methoxypyridazin-3-yl)-2-(1,3-oxazol-4-yl)-5-(trifluoromethoxy)-1H-benzimidazole (Example 155);
1-(6-methoxypyridazin-3-yl)-2-(1-methyl-1H-pyrazol-3-yl)-5-(trifluoromethoxy)-1H-benzimidazole (Example 156);
5-[3-(5-methoxypyridazin-2-yl)-6-(trifluoromethyl)-3H-imidazo[4,5-b]pyridin-2-yl]pyrazine-2-carbonitrile (Example 157);
1-(6-methoxypyridazin-3-yl)-2-(2-methyl-1,3-oxazol-4-yl)-5-(trifluoromethoxy)-1H-benzimidazole (Example 158);
2-(5-chloropyridin-2-yl)-3-(6-methoxypyridin-3-yl)-6-(trifluoromethyl)-3H-imidazo[4,5-b]pyridine (Example 159);
3-(6-methoxypyridin-3-yl)-2-(1-methyl-1H-1,2,3-triazol-4-yl)-6-(trifluoromethyl)-3H-imidazo[4,5-b]pyridine (Example 160);
1-(5-methoxypyrazine-2-yl)-2-pyridin-2-yl-5-(trifluoromethyl)-1H-benzimidazole (Example 161);
3-(6-methoxypyridin-3-yl)-2-(1-methyl-1H-pyrazol-3-yl)-6-(trifluoromethyl)-3H-imidazo[4,5-b]pyridine (Example 162);
1-(6-methoxypyridazin-3-yl)-2-(1-methyl-1H-1,2,3-triazol-4-yl)-5-(trifluoromethyl)-1H-benzimidazole (Example 163);
3-(5-methoxypyrazine-2-yl)-2-(1-methyl-1H-1,2,3-triazol-4-yl)-6-(trifluoromethyl)-3H-imidazo[4,5-b]pyridine (Example 164);
3-(5-methoxypyrazine-2-yl)-2-(1-methyl-1H-pyrazol-4-yl)-6-(trifluoromethyl)-3H-imidazo[4,5-b]pyridine (Example 165);
1-(6-methoxypyridazin-3-yl)-2-(1-methyl-1H-pyrazol-4-yl)-5-(trifluoromethoxy)-1H-benzimidazole (Example 166);
1-(6-methoxypyridazin-3-yl)-2-(1-methyl-1H-1,2,3-triazol-4-yl)-5-(trifluoromethoxy)-1H-benzimidazole (Example 167);
1-(6-methoxypyridazin-3-yl)-2-(5-methylisoxazol-3-yl)-5-(trifluoromethoxy)-1H-benzimidazole (Example 168);
3-(5-methoxypyrazine-2-yl)-2-(1-methyl-1H-imidazol-4-yl)-6-(trifluoromethyl)-3H-imidazo[4,5-b]pyridine (Example 169);
6-ethoxy-3-(6-methoxypyridin-3-yl)-2-pyridin-2-yl-3H-imidazo[4,5-b]pyridine (Example 170);
6-(cyclopropylmethoxy)-3-(6-methoxypyridin-3-yl)-2-pyridin-2-yl-3H-imidazo[4,5-b]pyridine (Example 171);
2-(2-ethyl-1,3-oxazol-4-yl)-3-(6-methoxypyridin-3-yl)-6-(trifluoromethyl)-3H-imidazo[4,5-b]pyridine (Example 172);
3-(6-methoxypyridin-3-yl)-6-propoxy-2-pyridin-2-yl-3H-imidazo[4,5-b]pyridine (Example 173);
6-isobuthoxy-3-(6-methoxypyridin-3-yl)-2-pyridin-2-yl-3H-imidazo[4,5-b]pyridine (Example 174);
3-(6-methoxypyridin-3-yl)-2-pyridin-2-yl-6-(2,2,2-trifluoroethoxy)-3H-imidazo[4,5-b]pyridine (Example 175);
3-(6-methoxypyridin-3-yl)-2-pyridin-2-yl-6-(2,2,2-trifluoro-1-methylethoxy)-3H-imidazo[4,5-b]pyridine (Example 176);
2-(5-fluoropyridin-2-yl)-3-(6-methoxypyridin-3-yl)-6-(trifluoromethoxy)-3H-imidazo[4,5-b]pyridine (Example 177);
6-(difluoromethoxy-2-(5-fluoropyridin-2-yl)-3-(6-methoxypyridin-3-yl)-3H-imidazo[4,5-b]pyridine (Example 178);
3-(6-methoxypyridin-3-yl)-2-pyridin-2-yl-7-(trifluoromethyl)imidazo[1,2-b]pyridazine (Example 179);
3-(6-methoxypyridin-3-yl)-2-pyridin-2-yl-6-(trifluoromethyl)pyrazolo[1,5-a]pyrimidine (Example 180);
2-(5-fluoropyridin-2-yl)-3-(6-methoxypyridin-3-yl)-7-(trifluoromethyl)imidazo[1,2-b]pyridazine (Example 181);
1-(6-methoxypyridin-3-yl)-2-pyridin-2-yl-5-(trifluoromethyl)-1H-indole (Example 182);
1-(6-methoxypyridin-3-yl)-2-pyridin-2-yl-5-(trifluoromethyl)-1H-pyrrolo[2,3-b]pyridine (Example 183);
2-(5-fluoropyridin-2-yl)-1-(6-methoxypyridin-3-yl)-5-(trifluoromethyl)-1H-pyrrolo[2,3-b]pyridine (Example 184);
2-(5-fluoropyridin-2-yl)-3-(6-methoxypyridin-3-yl)-6-(trifluoromethyl)-2H-indazole (Example 185);
3-(6-methoxypyridin-3-yl)-2-pyridin-2-yl-6-(trifluoromethyl)-2H-pyrazolo[4,3-b]pyridine (Example 186);
1-(5-methoxypyrazine-2-yl)-2-pyridin-2-yl-5-(trifluoromethyl)-1H-pyrrolo[2,3-b]pyridine (Example 187);
3-(6-methoxypyridin-3-yl)-2-pyridin-2-yl-6-(trifluoromethyl)-2H-indazole (Example 188);
3-(6-methoxypyridin-3-yl)-2-pyridin-2-yl-7-(trifluoromethyl)imidazo[1,2-a]pyridine (Example 190);
2-(5-fluoropyridin-2-yl)-3-(6-methoxypyridin-3-yl)-7-(trifluoromethyl)imidazo[1,2-a]pyridine (Example 191); and
2-(5-fluoropyridin-2-yl)-3-(6-methoxypyridin-3-yl)-6-(trifluoromethyl)pyrazolo[1,5-a]pyrimidine (Example 192)
or pharmaceutically acceptable salts thereof.

As the salts of said compounds represented by the formulae I and II, salts of acid adducts or base adducts can be used. The kind of the salts is not limited specifically as far as the salts are physiologically acceptable.

The pharmaceutically acceptable salts are, when the compound has a basic group, exemplified by salts of an inorganic acid such as hydrochloride, sulfate, phosphate or hydrobromide, or salts of an organic acid such as acetate, fumarate, oxalate, citrate, methanesulfonate, benzenesulfonate, tosylate or maleate. When the compound has an acidic group, salts of an alkali metal such as sodium or potassium, or salts or an alkaline earth metal such as calcium are exemplified as said salts.

When the compounds of the formulae I and II or the salts thereof include optically active compounds, they can be separated into an individual optical isomer by the usual method of optical resolution. Alternatively, the compounds of the formulae I and II or the optical active salts thereof can be synthesized by utilizing an optically-pure starting material or a compound having a known steric configuration.

One or more than two kinds of the compounds of the present invention represented by the formulae I and II or the salt thereof may be administered as it is to patients, but preferably, may be administered in well-known forms of preparation by adding active ingredients and pharmacologically and pharmaceutically acceptable additives.

The compound of the present invention can be administered to human or animals by appropriate administration routes after prepared in an appropriate dosage form (powders, injections, tablets, capsules or topycal external preparations) together with appropriate usual diluents and other additives, via appropriate routes of administration depending on its dosage form (e.g., intravenous administration, oral administration, cutaneous administration or topical administration).

As pharmacologically and pharmaceutically acceptable additives, can be used excipients, disintegrating agents, binders, lubricating agents, coating agents, pigments, diluents, bases and isotonizing agents.

Examples of preparations appropriate for oral administration are tablets, capsules, powders, fine granules, granules, liquids or syrups, and examples of preparations appropriate for non-oral administration are injections, drops or suppositories.

In the preparations appropriate for the oral administration, additives such as excipients, disintegrating agents, binding agents, lubricating agents, coating agents or bases can be used. And, when the compound of the present invention is administered to patients of therapeutic target, other ingredients appropriate for treating the target individuals and the compound of the present invention may be used together.

An administration route of the medicine of the present invention is not limited specifically, but the route of orally or non-orally administration can be adopted. The dose is determined depending on the individuals' age, weight, general health status, sex, diet, administration time, administration method, excretory time, combination of medicines, condition of disease under treatment at the time, and by consideration of these or other factors. The compounds of the present invention or the optical isomers thereof or pharmaceutically acceptable salts thereof are low in toxicity and can be used safely. The dose per day differs depending on status and weight of the individuals, kinds of the compounds, routes of administration, etc., and, for example, in case of non-oral, about 0.1-1000 mg/man/day, preferably about 500 mg/man/day are desirably administered via subcutaneously, intravenously, intramuscularly, or rectally, and in case of oral, about 0.1-1000 mg/man/day, preferably 1 about 500 mg/man/day are desirably administered.

Effect of the invention

The compound of the present invention depresses platelet aggregation induced by GPIb and GPVI. Since the GPIb and the GPVI work selectively when pathologic thrombus is formed induced by plaque rupture at an arteriosclerosis region, they do not accentuate bleeding risk and exert strong antithrombotic action.

The compound of the present invention is potent in the inhibitory activity of the platelet aggregation induced either by ristocetin via the GPIb or by collagen via GPVI, compared to the inhibitory activity of the platelet aggregation caused by ADP. Therefore, the compound of the present invention can be an antiplatelet agent which does not accentuate the bleeding risk.

The compound of the present invention is potent in the inhibitory activity of the platelet aggregation induced either by ristocetin via the GPIb or by collagen via GPVI, compared to the inhibitory activity of the platelet aggregation caused by ADP. Therefore, the compound of the present invention can be the antiplatelet agent which is expected to have high platelet-aggregation inhibitory action in high-speed condition of blood flow at the angiostenosis region by arteriosclerosis, etc. (at a time of pathologic thrombus formation: "high-shearing stress state"), compared to low-speed condition of the blood flow at the wounded region (at time of hemostasis formation: "low-shearing stress state").

The compound of the present invention has the antiplatelet function, and by the function, the compound can be a medicine for preventing, reducing and/or treating diseases relating to the function, for example, ischemic stroke, acute coronary syndrome, microvascular dysfunction, peripheral arterial disease, arteriosclerosis obliterans, ischemic heart disease, thrombotic microangiopathy (including thrombotic thrombocytopenic purpura and hemolytic uremia syndrome), and unstable or stable angina.

DESCRIPTION OF EMBODIMENTS

The compounds of the formulae Ia-Ie and the synthetic intermediates thereof can be produced by the following methods. The compounds of the formulae IIa-IIe can be also produced similarly to the compounds of the formulae Ia-Ie.

Unless otherwise recited in the producing methods, examples, and comparative examples, the following symbols indicate the following meanings:
APCI: atmospheric pressure chemical ionization
Ac: acetyl
Boc: t-butoxycarbonyl
Bu: butyl
DEPC: diethylcyanophosphorate
DMAC: dimethylacetamide
DMF: dimethylformamide
DMSO: dimethylsulfoxide
EDCI: 1-ethyl-3-(3-dimethylaminopropyl)carbodiimide
ESI: electrospray ionization
Et: ethyl
HATU: O-(7-azabenzotriazol-1-yl)-N,N,N',N',-tetramethyluroniumhexafluorophosphate
HOBu: 1-hydroxydibenzotriazole
Me: methyl
SEM: 2-(trimethylsilyl)ethoxymethyl
THF: tetrahydrofuran
TMS: trimethylsilyl Production Method 1

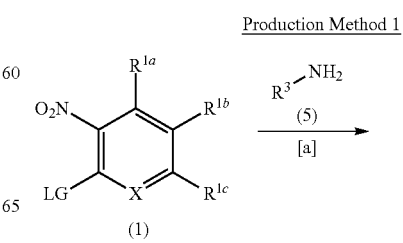

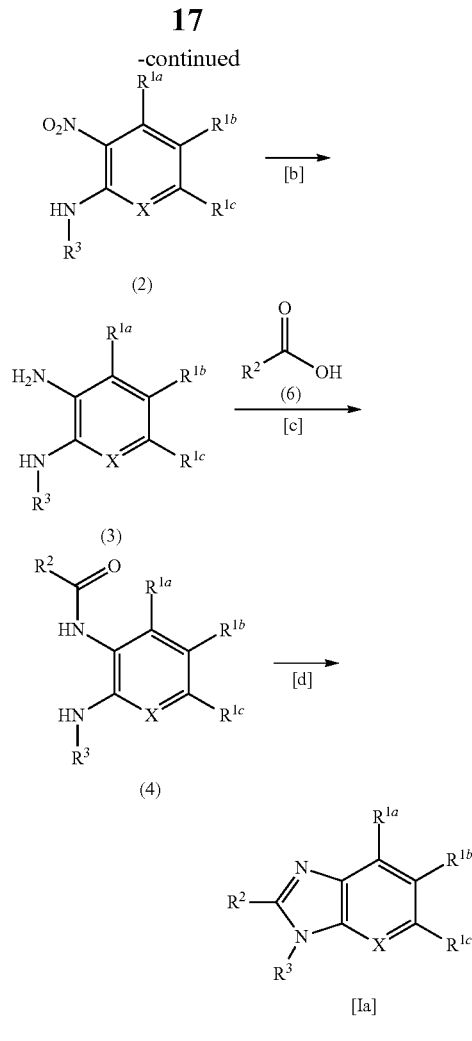

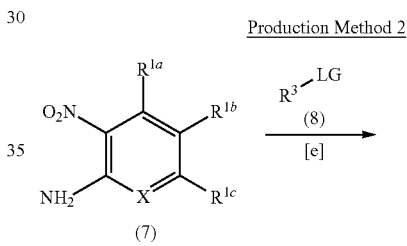

wherein, LG means a leaving group, for example, a halogen, and other symbols mean the same meanings as described above.

[Step a]

A compound (2) can be produced by reacting the compounds (1) and (5), in the presence or absence of catalyst, in appropriate solvents or without solvent.

In the absence of catalyst, the reaction proceeds suitably in the presence or absence of a base. As the base, alkali metal salts such as potassium carbonate, or organic bases such as triethylamine or diisopropylethylamine can be suitably used. The present reaction proceeds suitably at temperatures of, especially, 0° C.-150° C. As solvents, non-solvent or any solvents which do not affect the reaction can be used, for example, DMF, DMAC or DMSO can be suitably used. In the presence of catalysts, the catalysts and processes described in "Angewandte Chem. Int. Ed., 34, 6338 (2008), Angewandte Chem. Int. Ed., 48, 6954 (2009)", etc. can be suitably used.

[Step b]

The compound (3) can be produced by reducing a nitro group in the compound (2) in usual manner (hydrogenation process using Pd catalysts and reduction process using metal catalysts such as zinc or iron). And, the process using hydrazine monohydrate and iron (III) chloride described in "Tetrahedron Letter, 36, 2411 (1995)" can be also suitably used. AS a solvent, any solvent which does not affect the reaction can be applied, and an alcoholic solvent such as, methanol, ethanol or isopropanol can be recited. The present reaction can be added with an active carbon, and proceeds suitably at the reaction temperature of 60° C.-100° C.

[Step c]

The compound (4) can be produced by reacting the compound (3), the carboxylic acid (6) and an amidizing reagent, in an appropriate solvent, or without solvent. The present reaction suitably proceeds at −20° C. to 100° C., especially, 0° C. to a room temperature. As a solvent, any solvent which does not affect the reaction can be used, and for example, methylene dichloride, chloroform, THF, DMF or DMAC can be suitably used. As an amidizing reagent, a combination of EDCI, HOBt and triethylamine, or a combination of HATU or DEPC and triethylamine or diisopropylethylamine can be recited.

[Step d]

The compound [Ia] can be produced by treating the compound (4) with an acid in an appropriate solvent. The reaction proceeds suitably at temperatures of 60° C.-150° C. The present reaction proceeds suitably, especially at 80° C.-120° C. As solvents, any solvents which do not affect the reaction can be used, and for example, acetic acid, toluene, xylene or dioxane can be suitably used. As acids, hydrochloric acid, sulfuric acid, p-toluene sulfonic acid and acetic acid can be suitably used. Also, the reaction can be accelerated by irradiating microwave.

Production Method 2 wherein, LG is a leaving group, such as a halogen, and other symbols are the same as described above.

[Step e]

The compound (2) can be produced by reacting the compound (7) and the compound (8) in an appropriate solvent, or without a solvent. The present reaction proceeds suitably by adding an appropriate base, for example, an alkaline metal salt such as potassium carbonate, an alkaline earth metal salt such as cesium carbonate, or an organic base such as triethylamine and pyridine. As a solvent, any solvents which do not affect the reaction can be used, and for example, DMSO, DMF, and THF can be suitably used. And also can be suitably used the N-arylation reaction using a transition metal catalysts such as palladium and copper described in "Angewandte Chem. Int. Ed., 34, 6338 (2008), or Angewandte Chem. Int. Ed., 48, 6954 (2009)".

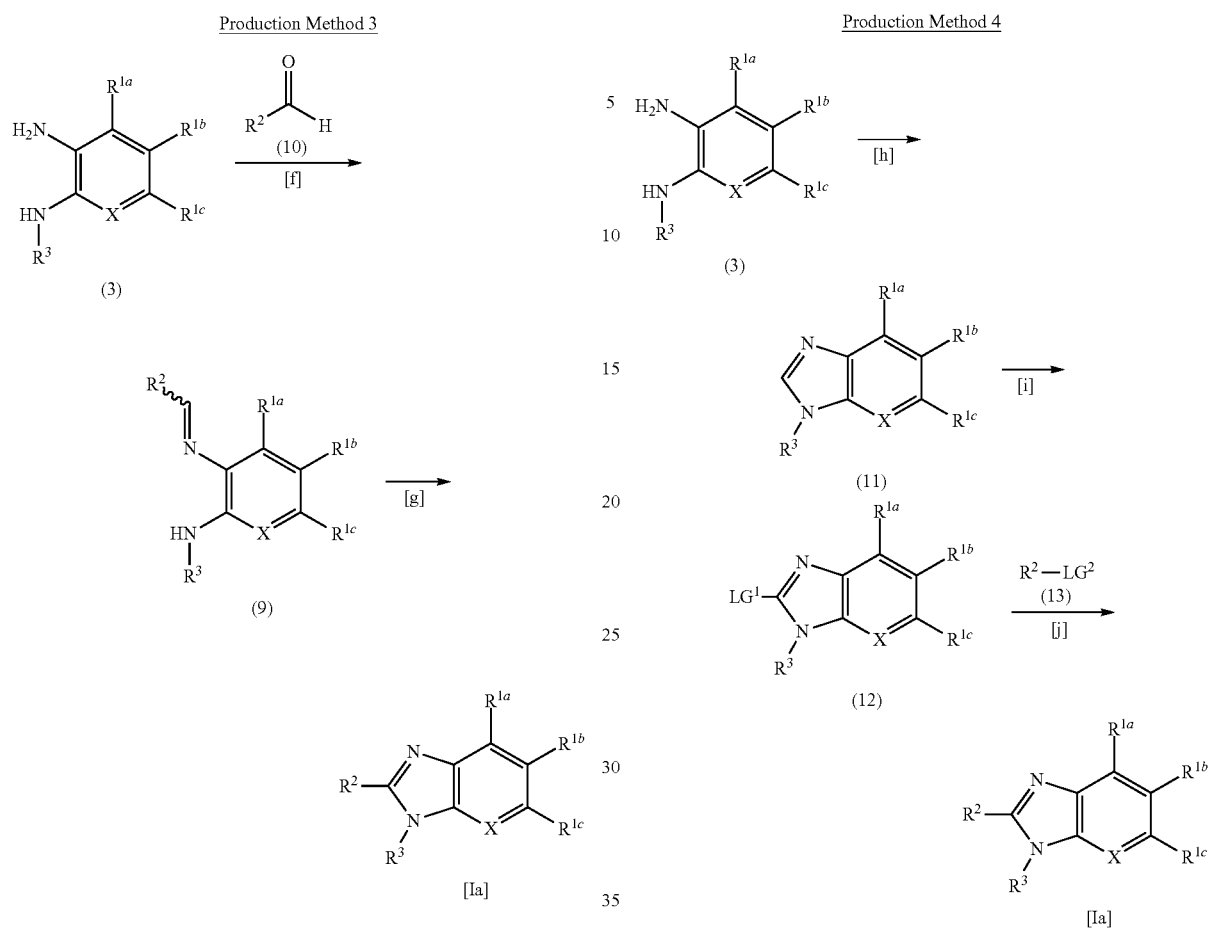

wherein, each symbol is the same as described above.

[Step f]

The compound (9) can be produced by reacting the compound (3) with aldehyde (10) in an appropriate solvent or without solvent. As a solvent, any solvent which does not affect the reaction can be used, and for example, methylene dichloride, toluene and xylene can be suitably used. The present reaction proceeds suitably at 60° C.-150° C. Appropriate acids can be added to the present reaction.

The compound (9) obtained can be used in the next reaction step without further purification.

[Step g]

The compound [Ia] can be produced by reacting the compound (9) in an appropriate solvent, in the co-presence of an acid and an oxidizing agent. As acids, for example, acetic acid, trifluoroacetic acid and p-toluenesulfonic acid are recited, and as an oxidizing agent, for example, sodium hydrosulfite ($Na_2S_2O_4$), iodine and hydrogen peroxide are recited. As solvents, any solvents which do not affect the reaction can be used, and for example, DMF, DMAC and an alcoholic solvent such as ethanol can be suitably used. The present reaction proceeds suitably at 60° C.-150° C.

The present production method can be conducted without isolating the intermediate from the compound (3) as described in "Synthesis., 1, 47 (2005)".

wherein, $LG^1$ is a halogen, $LG^2$ is, —$B(OH)_2$, —$B(OR)_2$, or —$SnR_3$, R is an alkyl, and each other symbol is the same as that described above.

[Step h]

The compound (11) can be produced by reacting the compound (3) and trialkyl orthoformate in an appropriate solvent, or without solvent. As solvents, any solvent which do not affect the reaction can be used, and for example, methylene dichloride, toluene, xylene and acetic acid can be suitably used. The present reaction proceeds suitably also by adding an acid, for example, acetic acid, trifluoroacetic acid or p-toluenesulfonic acid. The present reaction proceeds suitably at 0° C.-100° C.

[Step i]

The compound (12) can be produced by reacting the compound (11) with a halogenizing reagent in the presence or absence of a base, in an appropriate solvent. As the base, for example, organometallic reagent such as n-butyl lithium is recited, and as the halogenizing reagent, for example, carbon tetrabromide and N-bromosuccinimide are recited. When the base is used in the present reaction, any solvents which do not affect the reaction can be used, and for example, THF, hexane and toluene can be suitably used. The reaction proceeds suitably at the reaction temperature of –78° C. to room temperature. And, in the absence of the base, the solvent such as dioxane, THF, DMF or carbon tetrachloride can be suitably used. The reaction proceeds suitably at reaction temperatures from room temperature to 150° C.

[Step j]

The compound [Ia] can be produced by reacting the compound (12) and the compound (13) in an appropriate solvent, in the presence of a Pd catalyst as described in "Journal of Organometallic Chemistry., 576, 147 (1999)".

As the Pd catalyst, zero-valent palladium such as tetrakis-triphenylphosphine palladium (0) or tris(dibenzylidene acetone)dipalladium (0), and bivalent palladium such as acetic acid palladium (II) and chloro-bistriphenylphosphine palladium (II) are recited. Also an appropriate ligand can be added, and 2,2'-bis(diphenylphosphino)-1,1'-binaphthyl, 2-dicyclohexyl-phosphino-2',4',6'-triisopropylbiphenyl, 2-dicyclohexyl-phosphino-2'-(N,N-dimethylamino)biphenyl, etc. are recited. As solvents, any solvents which do not affect the reaction can be used, and in case of $LG^2$ is —$SnR_3$, such solvents as toluene, THF, dioxane are recited, and in case of $LG^2$ is —$B(OH)_2$ or —$B(OR)_2$, such solvents as toluene, THF, dioxane, dimethoxyethane or water, or a mixed solution thereof are recited. In case of $LG^2$ is —$B(OH)_2$ or —$B(OR)_2$, the reaction proceeds suitably by adding a base, and such bases as sodium carbonate, potassium phosphate and sodium t-butoxide are recited. The present reaction proceeds suitably at reaction temperatures of 60° C.-160° C.

wherein, R is an alkyl group such as a methyl group or an ethyl group, and each other symbol is the same as described above, and LGs may be the same or different.

Production Method

[Step a]

The compound (16) can be obtained by the SONOGASHIRA reaction between the compound (14) and the acetylene derivative (15) using the palladium (0) and copper catalyst. As the palladium catalyst, tetrakis-triphenylphosphine palladium (0), dichloro ditriphenylphosphino palladium (0), etc. can be suitably used. The solvent is not limited as far as it does not affect the reaction, and, THF, toluene, benzene, triethylamine, diethylamine, or a mixed solvent thereof can be properly used. The present reaction proceeds suitably by adding an appropriate base, for example, triethylamine, diisopropylethylamine or diethylamine. The reaction proceeds suitably at reaction temperatures from room temperature to 120° C. It is preferable that, among two LGs in the compound (14), the LG which does not connect to the carbon adjacent to X has higher reactivity.

The compound (16) can be also produced by converting an optionally protected hydroxy group into the leaving group by usual manner, after the present step has been conducted by using the compound having an optionally protected hydroxy group as the LG connecting to the carbon adjacent to X.

Production Method 5

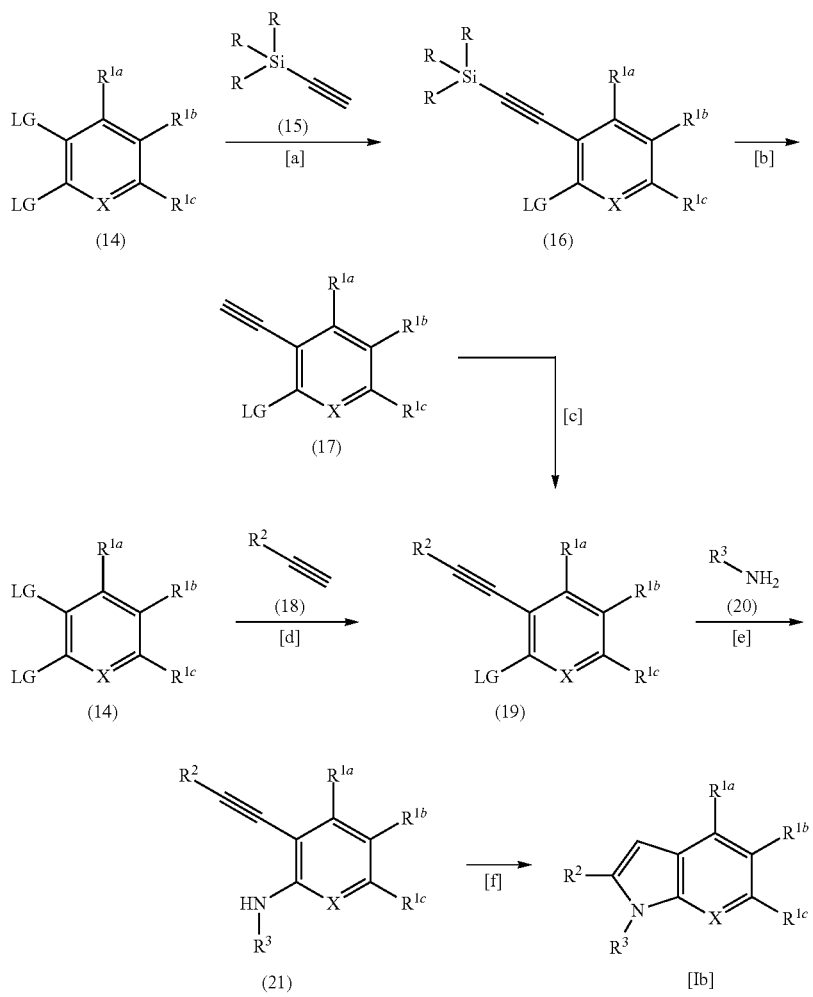

[Step b]

The compound (17) can be obtained from the compound (16) by the desilylation reaction described in "Greene's Protecting Group in Organic Synthesis". Preferably is recited the method of mixing with tetrabutylammonium fluoride, preferably in an appropriate solvent. The reaction proceeds suitably at reaction temperatures from 0° C. to room temperature.

[Steps c and d]

The compound (19) can be obtained by the SONOGASHIRA reaction using the compound (17) or the acetylene derivative (18) and the palladium (0) and copper catalyst. As the palladium catalysts, tetrakis-triphenylphosphine palladium (0), ditriphenylphosphine palladium (II) dichloride, etc. are preferable. The present step proceeds in a solvent, or without solvent, and the solvent is not limited specially, as far as it does not affect the reaction. For example, THF, toluene, benzene, triethylamine, diethylamine, or the mixed solvent thereof can be properly used. The reaction proceeds suitable at the reaction temperatures from room temperature to 120° C.

[Step e]

The compound (21) can be produced by reacting the compound (19) and the amine (20) in an appropriate solvent or without solvent. The present reaction proceeds suitably by adding an appropriate base, for example, an alkali metal salt or an alkaline-earth metal salt such as potassium carbonate and cesium carbonate, or an organic base such as triethylamine or pyridine. Any solvents which do not affect the reaction can be used, and for example, DMSO, DMF and THF are recited. More preferably, the N-arylation reaction catalyzed by the transition metal catalyst such as palladium or cupper can be suitably used as described in "Angewandte Chem. Int. Ed., 34, 6338 (2008)", or "Angewandte Chem. Int. Ed., 48, 6954 (2009)". The compound (21) obtained can be also utilized as it is to the next reaction step without isolation.

[Step f]

The compound (Ib) can be produced by adding an appropriate base such as potassium-t-botoxide or potassium hydride to the compound (21) in an appropriate solvent, or without solvent. Any solvent which does not affect the reaction can be used, and for example, toluene, DMF, THF, acetonitrile and N-methylpyrrolidone are recited. The method using palladium as described in "Tetrahedron Lett., 1988, 29, 1799", or the method using cupper as described in "J. Org. Chem., 1963, 28, 2163" can also be suitably used.

The compound (Ib) can also be produced in an one-pot reaction from the compound (14), the acetylene derivative (18) and the amine (20) by using such a method as described in "Org. Lett., 2005, 7, 439".

Production Method 6

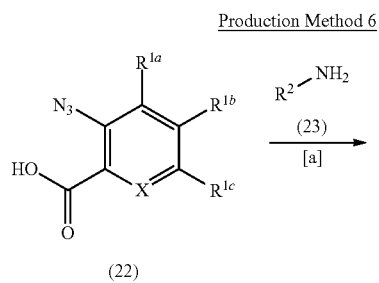

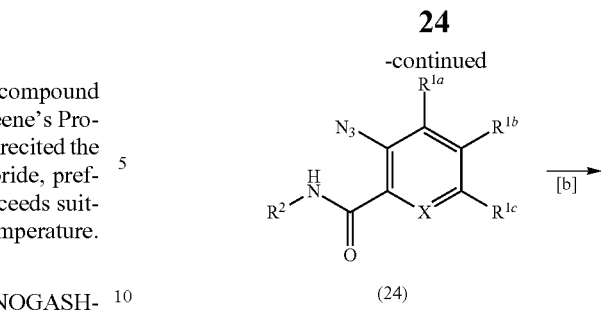

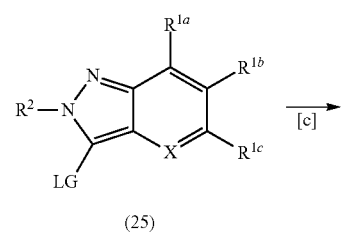

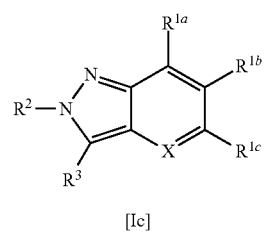

wherein, each symbol is the same meaning as above.

[Step a]

The compound (24) can be produced by reacting the compound (22), the amine (23) and an amidizing reagent, in an appropriate solvent, or without solvent. The present reaction proceeds suitably from −20° C. to 100° C., especially, from 0° C. to room temperature. Any solvent which does not affect the reaction can be used, and for example, methylene dichloride, chloroform, THF, DMF, DMAC, etc. can be suitably used. As an amidizing reagent, a combination of EDCI, HOBt and triethylamine, or a combination of HATU or and triethylamine or diisopropylethylamine may be recited.

[Step b]

The compound (25) can be produced by combining the compound (24) with thionyl chloride, phosphorus oxychloride, phosphorus pentachloride, etc. in an appropriate solvent, or without solvent. The present reaction proceeds suitably at 60° C.-150° C.

[Step c]

The compound (Ic) can be produced by the cross-coupling reaction of the compound (25) with an organic boron compound, an organic zinc compound. Any solvent which does not affect the reaction can be used, and dioxane, 1,2-dimethoxyethane, THF, DMF, toluene, or a mixture thereof can be properly used. The reaction proceeds suitably at 60° C.-120° C. As a metal, the O-valent or 2-valent palladium or nickel compound described in "Palladium Reagent, Catalysts, Innovations in Organic synthesis (New York: wiley, 1995)", etc. can be use in a catalytic amount or a stoichiometric amount. Also the legands described in "Acc. Chem. Res. 2008, 41, 1461." can be suitably used. Also, the present reaction can be accelerated by irradiation of microwave.

Production Method 7

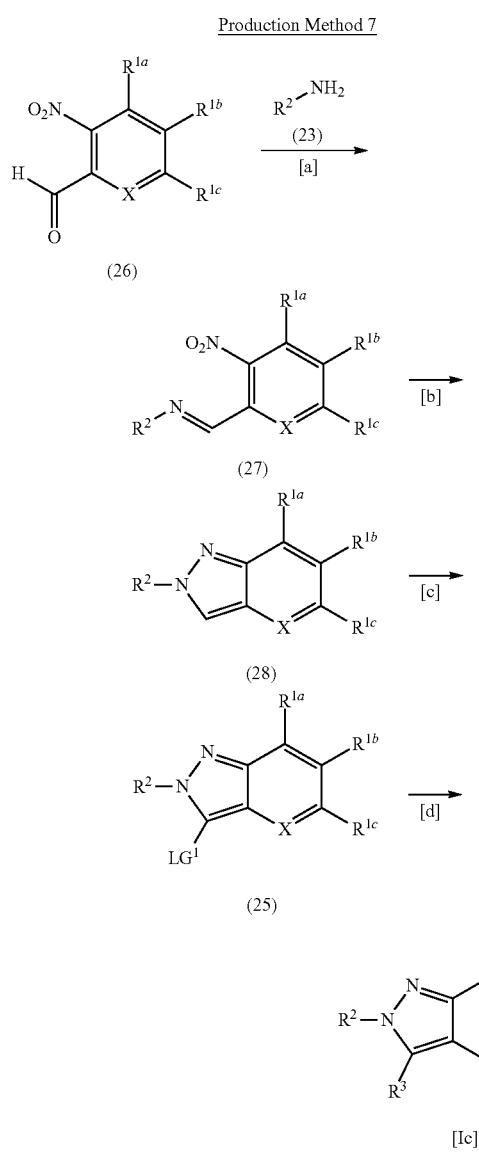

wherein, each symbol is the same meaning as above.

[Step a]

The compound (27) can be produced by reacting the compound (26) and the amine (23) in an appropriate solvent, or without solvent. The present reaction proceeds suitably from room temperature to 150° C. Any solvent which does not affect the reaction can be used, and benzene, toluene, xylene, or a mixture thereof can be properly used. In the present reaction, an appropriate acid may be added, and the compound (27) obtained can be used, as it is, to the next reaction step without isolation.

[Step b]

The compound (28) can be produced by reacting the compound (27) and triethyl phosphite, in an appropriate solvent, or without solvent. The present reaction proceeds suitably, especially at 150° C.

[Step c]

The compound (25) can be obtained by mixing the compound (28) with a usual halogenizing reagent (such as, chlorine, bromine, iodine, N-chlorosuccinimide or N-bromosuccinimide, N-iodosuccinimide or a halonium salt) in a solvent, or without solvent. For example, the solvent such as methylene dichloride, chloroform, ethyl acetate, diethyl ether, THF, 1,4-dioxane, acetonitrile, DMF, or a mixture solvent thereof can be properly used. The reaction temperatures are preferably from 0° C. to 150° C. To the present reaction may be added a suitable acid such acetic acid, trifluoroacetic acid, hydrochloric acid, or a radical initiator such as 2,2'-azobis(2-methylpropionitrile) or benzoyl peroxide.

[Step d]

The compound (Ic) can be synthesized by using a cross-coupling reaction of the compound (25) with an organic boron compound, an organic zinc compound, an organic silicon compound, an organic tin compound. Any solvent which does not affect the reaction can be used, and dioxane, 1,2-dimethoxyethane, THF, DMF, toluene, or a mixture thereof can be properly used. The reaction proceeds suitably at reaction temperatures of 60° C.-120° C. As a metal, zero valent or 2-valent palladium or nickel compounds described in "Palladium Reagent, Catalysts, Innovations in Organic synthesis (New York: wiley, 1995)", etc. can be used in a catalytic amount or in a stoichiometric amount. Also, such ligands as described in "Acc. Chem. Res. 2008, 41, 1461." can be suitably used. The present reaction is also accelerated by irradiation of microwave.

Production Method 8

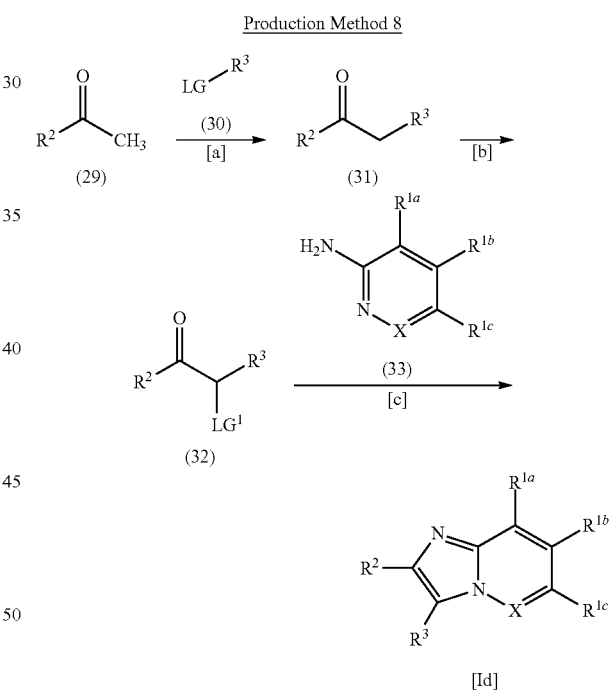

wherein, each symbol is the same as described above.

[Step a]

The compound (31) can be obtained by the coupling reaction of the compound (29) with the compound (30) using a metal catalyst (for example, "J. Am. Chem. Soc. 2002, 124, 12557-12565", "J. Am. Chem. Soc. 2001, 123, 7996-8002", etc.). There is no limitation in a solvent, and any solvent which does not affect the reaction can be properly used, for example, dioxane, 1,2-dimethoxyethane, THF, DMF, toluene, or a mixed solvent thereof. The reaction temperatures at 0° C.-150° C. are desirable. The compound (31) can be also synthesized using the Claisen condensation or the Friedel-Crafts reaction, etc.

[Step b]

The compound (32) can be obtained by mixing the compound (31) with the usual halogenizing reagent (chlorine, bromine, iodine, N-chlorosuccinimide, N-bromosuccinimide or N-iodosuccinimide, a halonium salt, etc.) in a solvent or without solvent. The solvent is not specifically limited unless it affects the reaction, and, for example, methylene dichloride, chloroform, ethyl acetate, diethyl ether, THF, 1,4-dioxane, acetonitrile, DMF, or a mixed solvent thereof can be properly used. The reaction temperatures at 0° C.-120° C. are desirable. To the present reaction, may be added a suitable acid (acetic acid, trifluoroacetic acid, hydrochloric acid, etc.) or a base which does not affect the reaction (sodium hydride, triethylamine, diisopropylethylamine, lithium hexamethyldisilazide, sodium hexamethyldisilazide, an organolithium compound, etc.).

[Step c]

The compound (Id) can be obtained by mixing the compound (32) and the compound (33) in a solvent or without solvent. The solvent is not specifically limited as far as it does not affect the reaction, and, for example, methanol, ethanol, methylene dichloride, chloroform, ethyl acetate, THF, DMF, toluene, pyridine, or a mixed solvent thereof can be properly used. The reaction temperatures at 50° C.-150° C. are desirable. To the present reaction may be added a proper base (sodium hydride, sodium bicarbonate, potassium carbonate, cesium carbonate, triethylamine, pyridine, etc.).

[Step a]

The compound (35) can be obtained by mixing the compound (33) and the compound (34) in a solvent or without solvent. The solvent is not specifically limited as far as it does not affect the reaction, and, for example, methanol, ethanol, methylene dichloride, chloroform, ethyl acetate, THF, DMF, toluene, pyridine, or a mixed solvent thereof can be properly utilized. The reaction temperatures at 0° C.-150° C. are desirable. To the present reaction may be added a suitable base (potassium carbonate, cesium carbonate, triethylamine, pyridine, etc.).

[Step b]

The compound (36) can be obtained by mixing the compound (35) and the usual halogenizing reagent (for example, chlorine, bromine, iodine, N-chlorosuccinimide, N-bromosuccinimide, N-iodosuccinimide or a halonium salt), in a solvent or without solvent. For example, methylene dichloride, chloroform, ethyl acetate, diethyl ether, THF, 1,4-dioxane, acetonitrile, DMF, or a mixed solvent thereof can be properly used. The reaction temperatures at 0° C.-150° C. are desirable. To the present reaction may be added a suitable acid such as acetic acid, trifluoroacetic acid or hydrochloric acid, or a radical initiator such as 2,2'-azobis(2-methylpropionitrile) or benzoyl peroxide.

[Step c]

The compound (Id) can be synthesized by the cross-coupling reaction of the compound (36) with an organic boron compound, an organic zinc compound, an organic silicon compound, or an organic tin compound. The solvent is not specifically limited as far as it does not affect the reaction, and, for example, dioxane, 1,2-dimethoxyethane, THF, DMF, toluene, or a mixed solvent thereof may be properly used. The reaction proceeds suitably at 60° C.-120° C. As a metal, zero valent or 2-valent palladium or nickel compounds described in "Palladium Reagent, Catalysts, Innovations in Organic synthesis (New York: wiley, 1995)", etc. can be used in a catalytic amount or in a stoichiometric amount. Also, such ligands as described in "Acc. Chem. Res. 2008, 41, 1461." can be suitably used. The present reaction is also accelerated by irradiation of microwave.

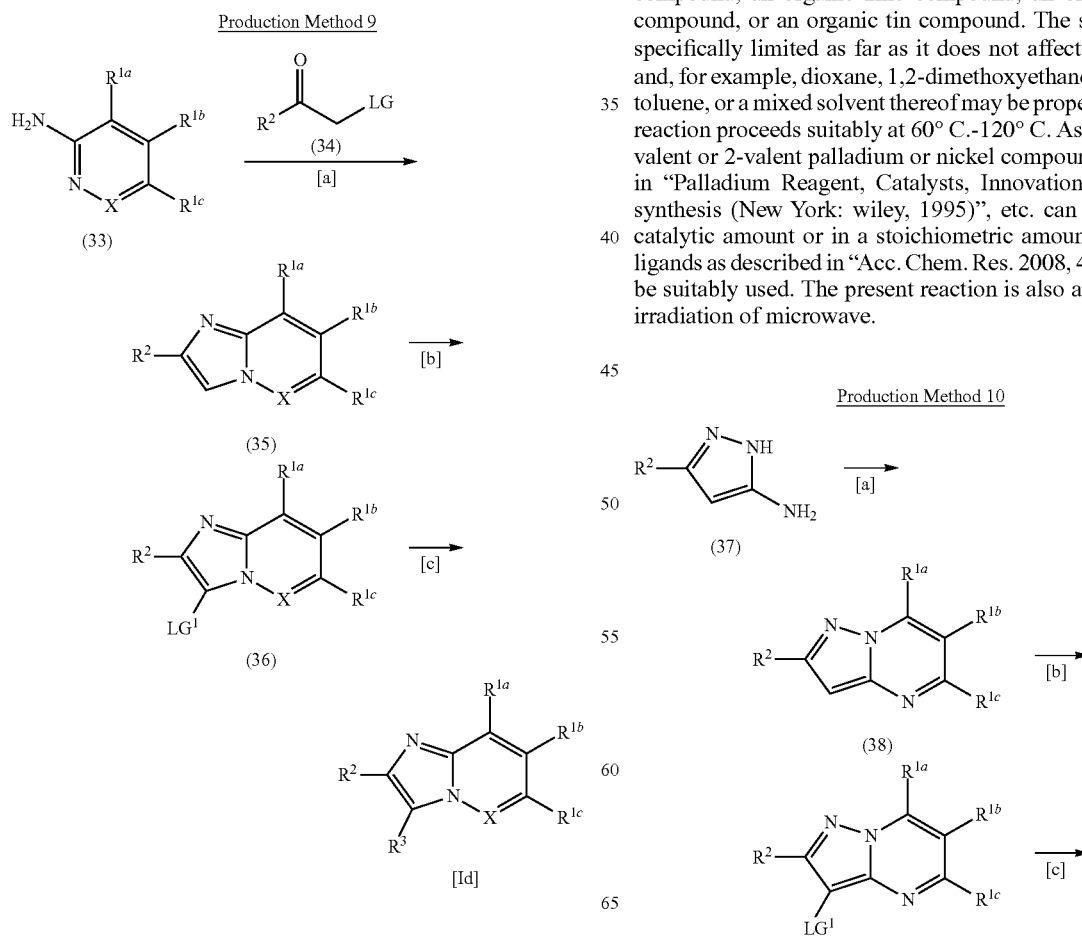

Production Method 9

Production Method 10 wherein, each symbol is the same as described above).

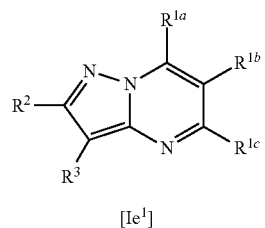

[Ie¹]

wherein, each symbol is the same as described above.

[Step a]

The compound (38) can be obtained by reacting the compound (37) and malondialdehyde or the binamidinium salt described in "J. Org. Chem. 2000, 65, 4571-4574". The solvent is not specifically limited as far as it does not affect the reaction, and, for example, methylene dichloride, chloroform, acetonitrile, diethyl ether, THF, 1,4-dioxane, DMF, toluene, or a mixed solvent thereof can be properly used. The reaction temperatures at 0° C.-80° C. are desirable. To the present reaction, a suitable acid (acetic acid, trifluoroacetic acid, hydrochloric acid, etc.) and a suitable base (sodium methoxide, potassium t-botoxide, triethylamine, etc.) may be added as far as they do not affect the reaction.

[Step b]

The compound (39) can be obtained by mixing the compound (38) with the usual halogenizing reagent (chlorine, bromine, iodine, N-chlorosuccinimide or N-bromosuccinimide, N-iodosuccinimide, or a halonium salt), etc. in a solvent or without solvent. For example, methylene dichloride, chloroform, ethyl acetate, diethyl ether, THF, 1,4-dioxane, acetonitrile, DMF, or a mixed solvent thereof can be properly used. The reaction temperatures at 0° C.-150° C. are desirable. To the present reaction may be added a suitable acid such as acetic acid, trifluoroacetic acid and hydrochloric acid, or a radical initiator such as 2,2'-azobis(2-methylpropionitrile) and benzoyl peroxide.

[Step c]

The compound (I$^{e1}$) can be synthesized by a cross-coupling reaction of the compound (39) with an organic boron compound, an organic zinc compound, an organic silicon compound, an organic tin compound, etc. The solvent is not specifically limited as far as it does not affect the reaction, and, for example, dioxane, 1,2-dimethoxyethane, THF, DMF, toluene, or a mixed solvent thereof can be properly used. The reaction proceeds suitably at temperatures of 60° C.-120° C. As a metal, zero valent or 2-valent palladium or nickel compounds described in "Palladium Reagent, Catalysts, Innovations in Organic synthesis (New York: wiley, 1995)", etc. can be used in a catalytic amount or in a stoichiometric amount. Also, such ligands as described in "Acc. Chem. Res. 2008, 41, 1461." can be suitably used. The present reaction is also accelerated by irradiation of microwave.

Production Method 11

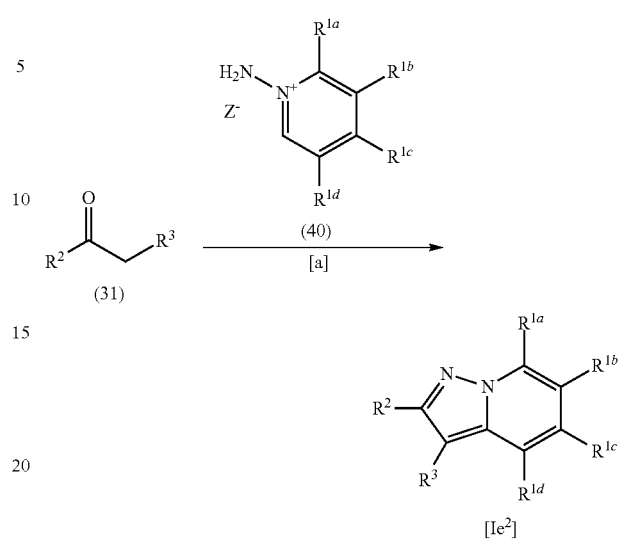

wherein, $Z^-$ represents a counter anion such as halide, and other symbol is the same as described above.

[Step a]

The compound (I$^{e2}$) can be obtained by mixing the compound (31) and the compound (40) in a solvent or without solvent. The solvent is not specifically limited as far as it does not affect the reaction, and, methanol, ethanol, etc. can be properly used. The reaction temperatures of 0° C.-150° C. are desirable. To the present reaction may be added a suitable base (triethylamine, pyridine, 1,8-diazabicyclo[5.4.0]undec-7-ene, etc.).

Production Method 12

The functional groups contained in the compounds of the present invention, their synthetic intermediates, or their starting compounds can be converted by the usual methods described in "Comprehensive Organic Transformations: A guide to Functional Group Preparations, Fiesers' Reagents for Organic Synthesis", etc., for example, by the following methods.

(1) When the compounds of the present invention, their synthetic intermediates, or their starting compounds have functional groups (hydroxyl, amino, carboxy, etc.), the reaction can be conducted by protecting these functional groups with the usual protecting groups as described in "Greene's Protecting Group in Organic Synthesis", then, after reaction, the targeted compound can be obtained by removing said protecting groups. In this case, the protecting groups for the hydroxyl group are exemplified by tetrahydropyranyl, TMS and an aryl, the protecting groups for the amino are exemplified by Boc or benzyloxycarbonyl, the protecting groups for carboxy are exemplified by an alkyl such as methyl, ethyl and benzyl, the protecting groups for the imidazolyl group are exemplified by a trityl group, and the substituents for the pyrolyl group are exemplified by SEM.

(2) When the compounds of the present invention, their synthetic intermediates or their starting compounds have an amino functional group, the amino is optionally protected firstly, then, (i) it is reacted with an alkyl halogenide in the presence of a base (sodium hydride, triethylamine, sodium carbonate, potassium carbonate, etc.), or (ii) alcohol is treated by the MITSUNOBU reaction using an alkylazodicarboxylate and triphenylphosphine, then optionally via deprotection, the compound having the amino optionally mono- or di-substituted by alkyls can be obtained.

(3) When the compounds of the present invention, their synthetic intermediates or their starting compounds have hydroxyl, (i) the hydroxyl is reacted with an alkyl halide in the presence of a base (sodium hydride, triethylamine, sodium carbonate, potassium carbonate, etc.), or (ii) alcohol is treated by the MITSUNOBU reaction using an alkylazodicarboxylate and triphenylphosphine, then, the compounds having an alkoxy group optionally substituted by an alkyl can be obtained.

(4) When the compounds of the present invention, their synthetic intermediates or their starting compounds have amino, they can be converted to the compounds having a corresponding amido group by converting the amino into the corresponding amido by using acyl halide.

(5) When the compounds of the present invention, their synthetic intermediates or their starting compounds have a double bond, they can be converted into the compounds having a corresponding single bond by a catalytic reduction of the double bond by using a transition metal catalyst (platinum, palladium, rhodium, ruthenium, nickel, etc.).

(6) When the compounds of the present invention, their synthetic intermediates or their starting compounds have an ester group, they can be converted into the corresponding carboxy compounds by hydrolyzing the ester group with alkali (sodium hydroxide, potassium hydroxide, etc.).

(7) When the compounds of the present invention, their synthetic intermediates or their starting compounds have a carbamoyl, the corresponding nitrile compounds can be obtained by reacting the carbamoyl with trifluoroacetic acid anhydride.

(8) When the compounds of the present invention, their synthetic intermediates or their starting compounds have hydroxyl, the hydroxy group can be converted to the corresponding halogen by treating it with a halogenizing agent. And, when the compounds of the present invention, their synthetic intermediates or their starting compounds have a halogen, the corresponding compounds having an alkoxy can be obtained by converting the halogen into the corresponding an alkoxy by treating with alcohol.

(9) When the compounds of the present invention, their synthetic intermediates or their starting compounds have ester, they can be converted into the corresponding hydroxy compounds by reducing the ester using a reducing agent (a metal reducing agent such as lithium aluminum hydride, sodium borohydride, lithium borohydride, and diborane).

(10) When the compounds of the present invention, their synthetic intermediates or their starting compounds have hydroxyl, they can be converted into the compounds having aldehyde, ketone or carboxy by oxidizing them by an oxidizing agent.

(11) When the compounds of the present invention, their synthetic intermediates or their starting compounds have carbonyl or aldehyde, they can be converted into the compounds having an optionally mono- or di-substituted aminomethyl by carrying out the reductive amination reaction in the presence of an amine compound and a reducing agent (sodium borohydride, sodium cyanoborohydride, etc.).

(12) When the compounds of the present invention, their synthetic intermediates or their starting compounds have aldehyde, they can be converted into the compounds having a corresponding oxime by reacting them with hydroxylamine or O-alkylhydroxylamine in alcohol (methanol, ethanol, etc.), in the presence of a base (sodium bicarbonate, etc.).

(13) When the compounds of the present invention, their synthetic intermediates or their starting compounds have a halogen, they can be converted into the compounds having a corresponding cyano group by treating them with a cyanizing agent.

(14) When the compounds of the present invention, their synthetic intermediates or their starting compounds have a halogen, they can be converted into the compounds having hydroxyl, amino, an amino optionally substituted by 1 or 2 alkyl, an alkyl, an alkenyl or an aryl group by the reaction using a transition metal catalyst such as Pd. The halogen can be converted into hydroxyl by a similar method, for example, as described in "J. Am. Chem. Soc., 128, 10694 (2006)", into an amino optionally substituted with 1 or 2 alkyl by a similar method as described in "Tetrahedron, 58, 2041 (2002)", into an alkenyl group by a similar method as described in "J. Org. Chem., 71, 9681 (2006)", and into an aryl group by a similar method as described in "Journal of Organometallic Chemistry., 576, 147 (1999)".

(15) When the compounds of the present invention, their synthetic intermediates or their starting compounds have a cyano group, they can be converted into the compounds having an aldehyde group by using a reducing agent (diisobutylaluminum hydride, etc.).

(16) When the compounds of the present invention, their synthetic intermediates or their starting compounds have a vinyl group, they can be converted into the compounds having a formyl group by the ozone oxidation or the osmium oxidation and successively by the iodic acid oxidation.

(17) When the compounds of the present invention, their synthetic intermediates or their starting compounds have 2-halogenopyridine, 2-halogenopyrazine, 2-halogenopyridazine or 2-halogenopyrimidine, they can be converted into the compounds having an alkoxy, an alkylthio, amino or an amino optionally substituted by 1 or 2 alkyl, cyano or a fluoro group by reacting them with a nucleophile.

(18) When the compounds of the present invention, their synthetic intermediates or their starting compounds have a phenolic hydroxy group, the compounds having difluoroalkoxy can be obtained by reacting them with chlorodifluoro methane or sodium chlorodifluoroacetic acid, and also the compounds having a trifluoromethoxy group can be obtained by using methods described in "Bull. Chem. Soc. Jpn. 2000, 73, 471-484" and "J. Org. Chem., 1979, 44, 2907".

The compounds of the present invention and each of their synthetic intermediates thus obtained can be purified using the usual chemical processes such as extraction, crystallization, re-crystallization, and various chromatography.

The compounds of the present invention can be converted into the pharmaceutically acceptable salts thereof by using the usual methods, and these salts can be purified by the usual chemical processes such as re-crystallization.

The compounds of the present invention include a mixture of stereo-isomers, or a pure or substantially pure form of each stereoisomer. For example, when the compounds of the present invention have one or more asymmetric centers on either of carbon, the compounds of the present invention may exist in an enantiomer or a diastereomer, or a mixture thereof. The compounds of the present invention include their isomers, or the mixtures thereof. And, when the compounds of the present invention include a double bond, stereo-isomers (cis- and trans-isomers) can exist, and when the compounds of the present invention include an unsaturated bonding such as carbonyl, tautomers can exist.

EXAMPLES

The present invention is further explained by the following Examples, but the scope of the present invention is not limited by these Examples.

Example 1

1-(6-methoxypyridazin-3-yl)-2-pyridin-2-yl-5-(trifluoromethyl)-1H-benzimidazole

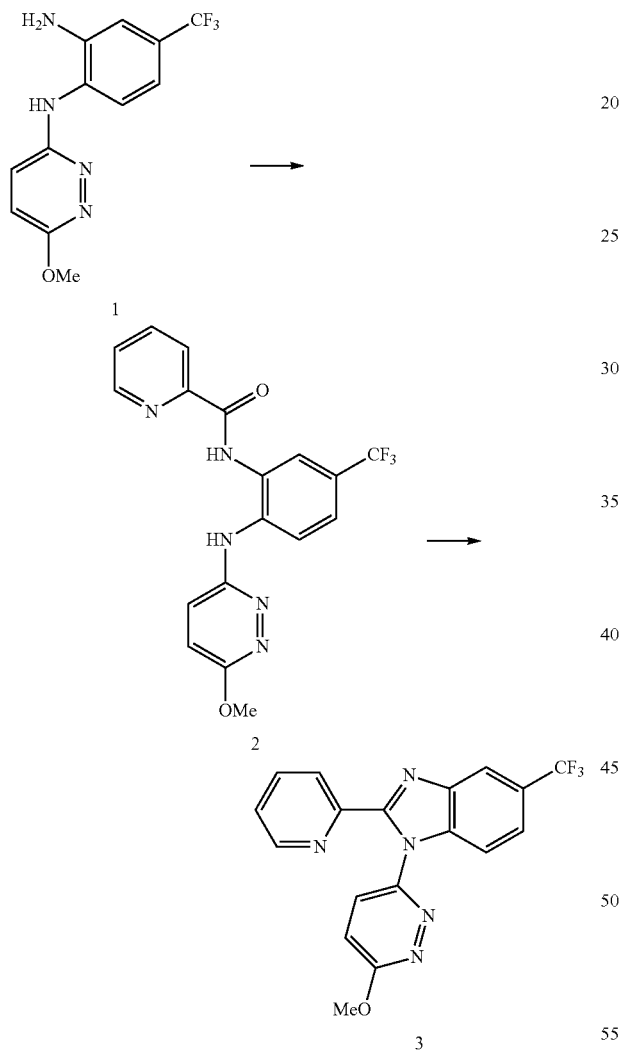

To a pyridine (27.5 ml) solution of the compound 1 (2.75 g) (the same compound as that described in Reference Example 2) was added picolinic acid chloride hydrochloride (4.67 g) at 0° C., and the mixture was stirred for 1 h at room temperature. After the reaction mixture was concentrated, the concentrated residue was purified by a silica gel column chromatography affording a crude compound 2 (4.08 g). The obtained crude compound 2 (4.08 g) was diluted in acetic acid (40 ml), and the solution was stirred at 80° C. for 20 h. The solution was kept standing to cool to room temperature, then after being concentrated, chloroform was added to the concentrate, and the resulting solution was washed with a saturated sodium bicarbonate solution. The organic phase was concentrated, and then purified by the silica gel column chromatography. To the obtained residue was added a solution of ethyl acetate/n-heptane (1:5), and the resulting deposit was obtained by filtration. To the obtained crude product was added ethyl acetate, and the resulting deposit was filtrated to produce the compound 3 (1.65 g).

MS m/z 372 [M+H]+, APCI(+)

Example 2

2-(6-fluoropyridin-2-yl)-1-(6-methoxypyridazin-3-yl)-5-(trifluoromethyl)-1H-benzimidazole

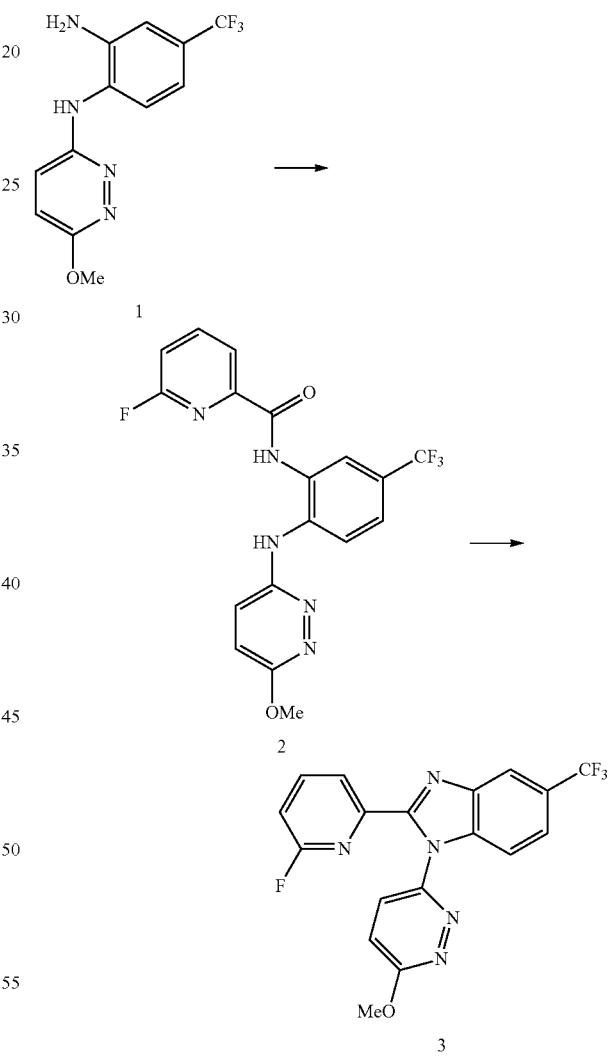

The compound 1 (the same compound as that described in Reference Example 2) (300 mg) was dissolved in methylene dichloride (5.3 ml), and thereto were added 6-fluoro-2-pyridine carboxylic acid (156 mg), EDCI-HCl (304 mg) and HOBt-H₂O (267 mg). After stirring the solution all day and all night, water and potassium carbonate were added thereto, and insoluble materials were filtrated. The organic layer was washed with water, followed by evaporation of the solvent in vacuo, and the residue was purified by the silica gel column chromatography affording the compound 2 (289 mg).

MS m/z 408 [M+H]+, APCI(+)

The compound 2 (100 mg) was dissolved in a mixed solvent of xylene/acetic acid (4:1, 2 ml), and heated to 170° C. by irradiation of microwave. After the reaction solution was stirred for 1 h and kept standing to cool to room temperature, the solvent was evaporated in vacuo. The residue was purified by the silica gel column chromatography affording the compound 3 (78.9 mg).

MS m/z 390 [M+H]+, APCI(+)

Example 3

1-(6-methoxypyridazin-3-yl)-2-pyridin-2-yl-5-(trifluoromethoxy)-1H-benzimidazole

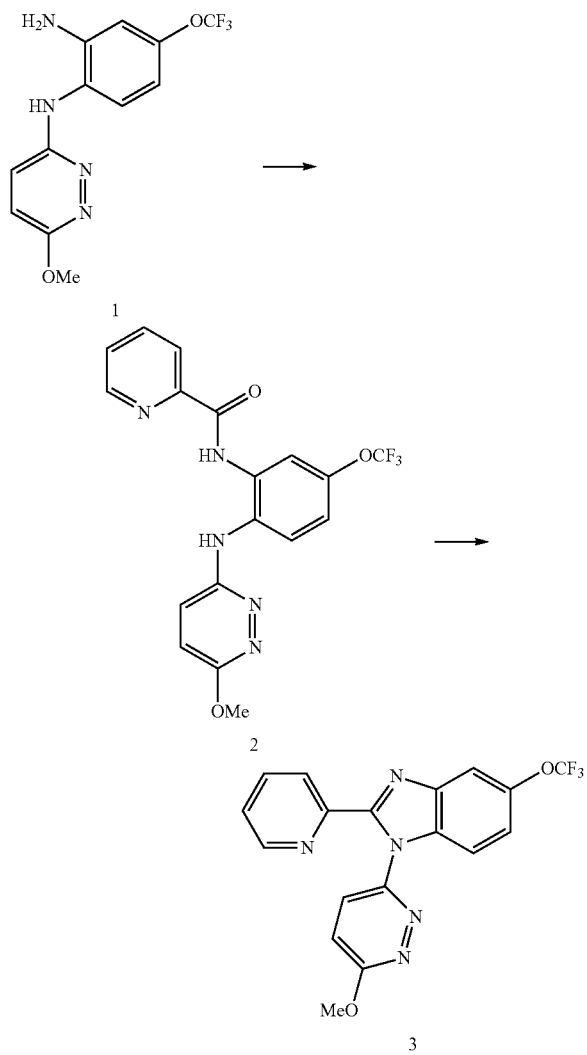

The compound 1 (the same compound as that described in Reference Example 3) (0.82 g) was dissolved in DMF (15 ml), and to the solution were added picolinic acid (505 mg), HATU (2.08 g) and diisopropylethylamine (951 µl). After stirring the solution all day and all night, water was added thereto, and the solution was extracted with ethyl acetate. The organic layer was washed with a saturated aqueous solution of sodium chloride (or saturated saline), and the organic layer was dried with anhydrous sodium sulfate. After filtration and evaporation, the evaporated residue was purified by the silica gel column chromatography affording a crude compound 2. To the crude compound 2 was added ethyl acetate/n-hexane (1/2), and the precipitate was filtrated affording the compound 2 (0.11 g).

MS m/z 406[M+H]+, APCI(+)

The compound 2 (14.0 mg) was dissolved in acetic acid (1 ml), and the solution was heated to 100° C. After the solution was stirred for 2 days and kept standing to cool to room temperature, the solvent was evaporated in vacuo. The evaporated residue was purified by the silica gel column chromatography affording the compound 3 (15.0 mg).

MS m/z 388 [M+H]+, APCI(+)

Example 4

2-(5-fluoropyridin-2-yl)-3-(6-methoxypyridin-3-yl)-6-(trifluoromethyl)-3H-imidazo[4,5-b]pyridine

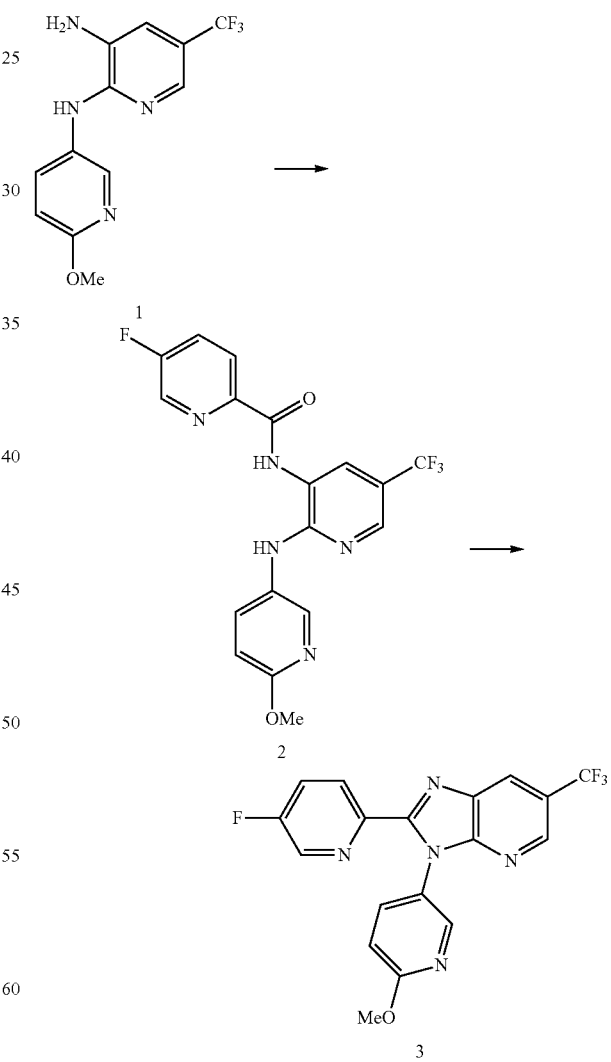

5-Fluoro-2-pyridine carboxylic acid (169 mg) was suspended in methylene dichloride (3 ml), and thereto were added oxalyl chloride (131 µl) and DMF (5 µl) at 0° C. After stirring the solution at room temperature for 2 h, the solvent was evaporated in vacuo. To the evaporated residue was added ethyl acetate (3 ml), and thereto at 0° C. were added an ethyl acetate solution (3 ml) of the compound 1 (the same as the compound of Reference Example 4) (284 mg) and an aqueous 10%-potassium carbonate solution (3 ml). After the solution was stirred at room temperature for 2 h, the organic layer was separated, washed with an aqueous solution saturated with sodium chloride (or saline solution) and dried with anhydrous sodium sulfate. After the solution was filtrated and concentrated, the concentrated residue was purified by the silica gel column chromatography, and the compound 2 (356 mg) was obtained.

MS m/z 408 [M+H]+, APCI(+)

The acetic acid (6 ml) solution of the compound 2 (0.55 g) was heated to 100° C. After the solution was stirred for 2 days, it was cooled to room temperature, and the solvent was evaporated in vacuo. To the evaporated residue was added ethyl acetate, and the organic layer was washed with an aqueous solution saturated with sodium bicarbonate. After the organic layer was filtrated and evaporated, the residue was purified by the silica gel column chromatography, and the compound 3 (0.39 g) was obtained.

MS m/z 390 [M+H]+, APCI(+)

Example 5

N-methyl-5-[2-pyridin-2-yl-6-(trifluoromethyl)-3H-imidazo[4,5-b]pyridin-3-yl]pyridin-2-amine

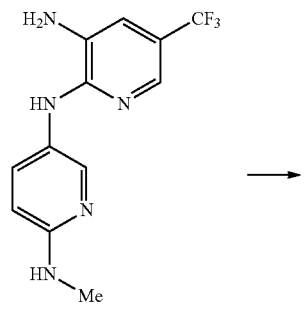

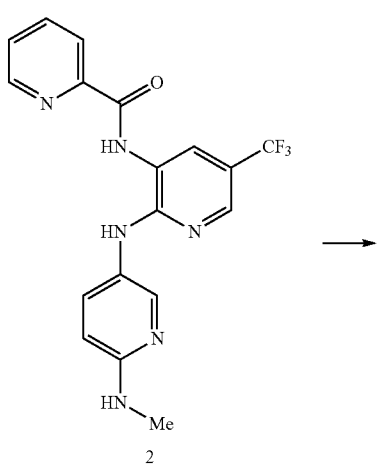

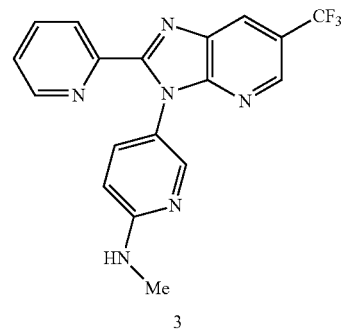

The compound 1 (the same as the compound described in Reference Example 6) (173 mg) was diluted in methylene dichloride (6.1 ml), and picolinic acid (79 mg), EDCI-HCl (176 mg), HOBt-H$_2$O (155 mg) were added thereto. After the solution was stirred for 2 days, methylene dichloride, water and potassium carbonate were added thereto, and the organic layer was separated. After the organic layer was concentrated, the concentrated residue was purified by the silica gel column chromatography, and the compound 2 (126 mg) was obtained.

MS m/z 389[M+H]+, APCI(+)

The compound 2 (126 mg) was diluted in acetic acid (3.2 ml), and the solution was heated to 100° C. After the solution was stirred all day and all night, chloroform, water and potassium carbonate were added, and the organic layer was separated. After the organic layer was concentrated, the concentrated residue was purified by the silica gel column chromatography, and the compound 3 (59 mg) was obtained.

MS m/z 371[M+H]+, APCI(+)

Example 6

N,N-dimethyl-5-[2-pyridin-2-yl-6-(trifluoromethyl)-3H-imidazo[4,5-b]pyridin-3-yl]pyridin-2-amine

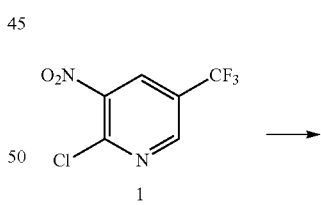

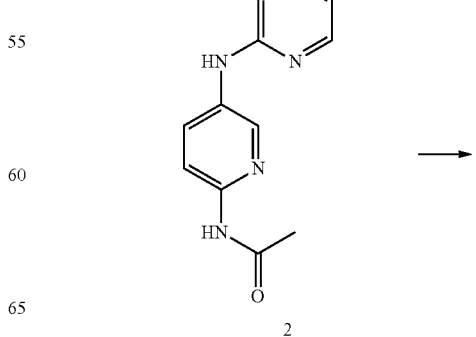

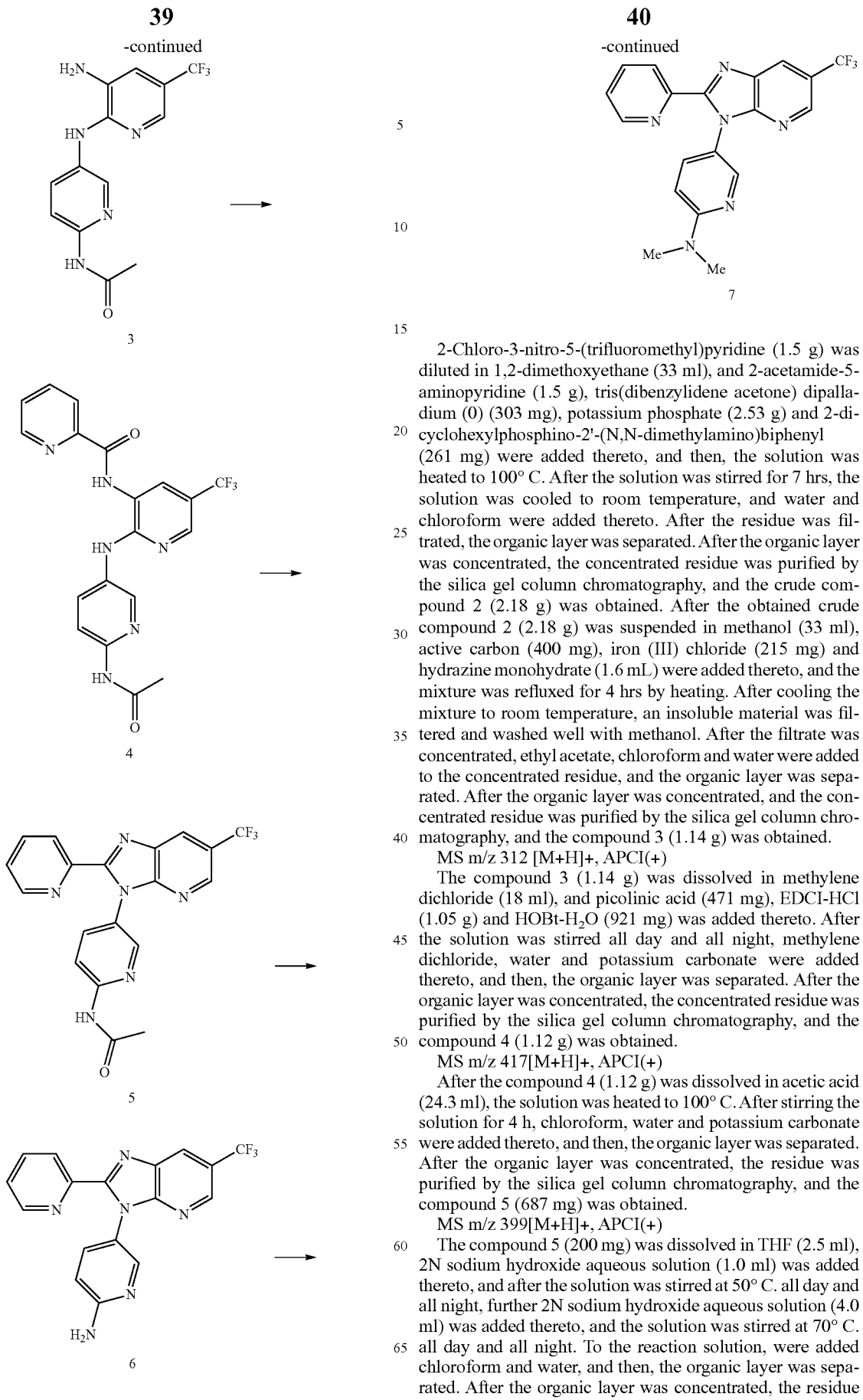

2-Chloro-3-nitro-5-(trifluoromethyl)pyridine (1.5 g) was diluted in 1,2-dimethoxyethane (33 ml), and 2-acetamide-5-aminopyridine (1.5 g), tris(dibenzylidene acetone) dipalladium (0) (303 mg), potassium phosphate (2.53 g) and 2-dicyclohexylphosphino-2'-(N,N-dimethylamino)biphenyl (261 mg) were added thereto, and then, the solution was heated to 100° C. After the solution was stirred for 7 hrs, the solution was cooled to room temperature, and water and chloroform were added thereto. After the residue was filtrated, the organic layer was separated. After the organic layer was concentrated, the concentrated residue was purified by the silica gel column chromatography, and the crude compound 2 (2.18 g) was obtained. After the obtained crude compound 2 (2.18 g) was suspended in methanol (33 ml), active carbon (400 mg), iron (III) chloride (215 mg) and hydrazine monohydrate (1.6 mL) were added thereto, and the mixture was refluxed for 4 hrs by heating. After cooling the mixture to room temperature, an insoluble material was filtered and washed well with methanol. After the filtrate was concentrated, ethyl acetate, chloroform and water were added to the concentrated residue, and the organic layer was separated. After the organic layer was concentrated, and the concentrated residue was purified by the silica gel column chromatography, and the compound 3 (1.14 g) was obtained.

MS m/z 312 [M+H]+, APCI(+)

The compound 3 (1.14 g) was dissolved in methylene dichloride (18 ml), and picolinic acid (471 mg), EDCI-HCl (1.05 g) and HOBt-H$_2$O (921 mg) was added thereto. After the solution was stirred all day and all night, methylene dichloride, water and potassium carbonate were added thereto, and then, the organic layer was separated. After the organic layer was concentrated, the concentrated residue was purified by the silica gel column chromatography, and the compound 4 (1.12 g) was obtained.

MS m/z 417[M+H]+, APCI(+)

After the compound 4 (1.12 g) was dissolved in acetic acid (24.3 ml), the solution was heated to 100° C. After stirring the solution for 4 h, chloroform, water and potassium carbonate were added thereto, and then, the organic layer was separated. After the organic layer was concentrated, the residue was purified by the silica gel column chromatography, and the compound 5 (687 mg) was obtained.

MS m/z 399[M+H]+, APCI(+)

The compound 5 (200 mg) was dissolved in THF (2.5 ml), 2N sodium hydroxide aqueous solution (1.0 ml) was added thereto, and after the solution was stirred at 50° C. all day and all night, further 2N sodium hydroxide aqueous solution (4.0 ml) was added thereto, and the solution was stirred at 70° C. all day and all night. To the reaction solution, were added chloroform and water, and then, the organic layer was separated. After the organic layer was concentrated, the residue was purified by the silica gel column chromatography, and the compound 6 (148 mg) was obtained.

MS m/z 357[M+H]+, APCI(+)

After the compound 6 (123 mg) was dissolved in acetonitrile (3 ml), an aqueous 37% formaldehyde solution (3.5 ml), cyano sodium borohydride (71.3 mg) and acetic acid (60 mg) were added thereto. After the solution was stirred for 3 h, chloroform, water and potassium carbonate were added thereto, and then, the organic layer was separated. After the organic layer was concentrated, the residue was purified by the silica gel column chromatography, and the compound 7 (31 mg) was obtained.

MS m/z 385[M+H]+, APCI(+)

Example 7

6-[1-(6-methoxypyridazin-3-yl)-5-(trifluoromethyl)-1H-benzimidazole-2-yl]nicotinonitrile

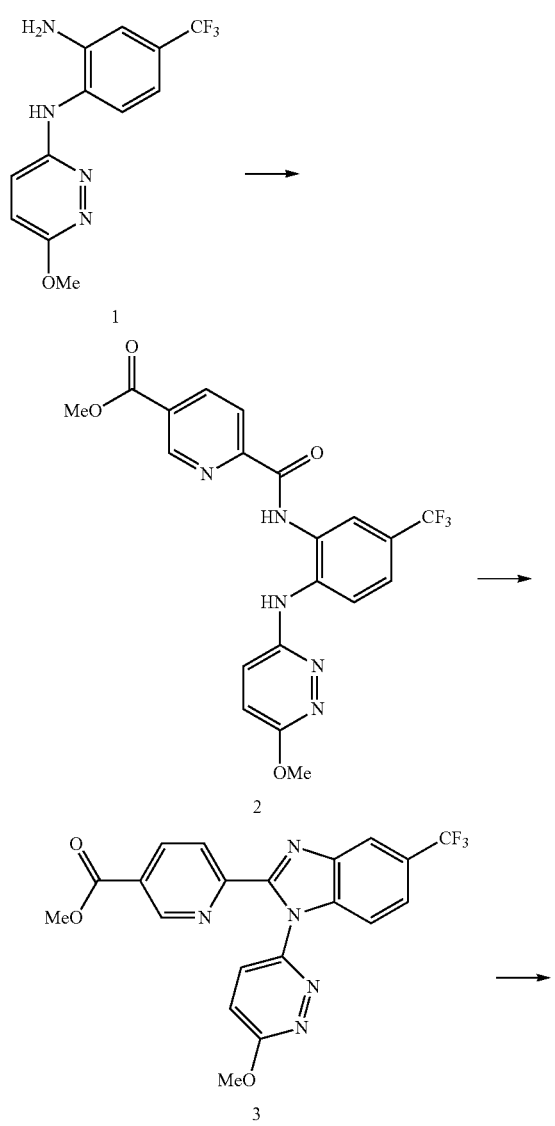

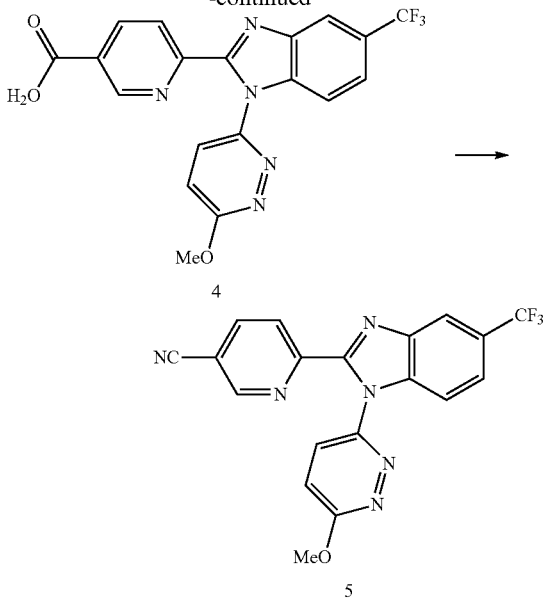

To a DMF (50 ml) solution of the compound 1 (the same as the compound described in Reference Example 2) (3.00 g) were added 5-(methoxycarbonyl)pyridine-2-carboxylic acid (2.10 g), HATU (4.41 g) and diisopropylethylamine (2.76 ml). After the mixed solution was stirred at room temperature for 18 h, an aqueous solution saturated with sodium bicarbonate was added thereto, and the mixture was extracted with ethyl acetate. The organic layer was washed with water and a saturated saline, and then dried with anhydrous sodium sulfate. After the organic layer was concentrated, the residue was purified by the silica gel column chromatography, and the compound 2 (3.04 g) was obtained.

MS m/z 448 [M+H]+, APCI(+)

The compound 2 (5.50 g) was dissolved in acetic acid (50 ml), and was heated to 105° C. After the solution was stirred for 1 day and kept standing to cool to room temperature, the solvent was evaporated in vacuo. To the residue was added ethyl acetate, and after the solution was washed with an aqueous solution saturated with sodium bicarbonate and a saturated saline, the solution was dried with anhydrous sodium sulfate. After the solution was filtrated and concentrated, the residue was purified by the silica gel column chromatography, and the crude product 3 was obtained. To the obtained crude product 3 was added diethyl ether, and the precipitated product was filtrated affording the compound 3 (1.76 g).

MS m/z 430 [M+H]+, APCI(+)

The compound 3 (429 mg) was suspended in a 7N ammonia-methanol solution (5 ml), and the solution was heated to 80° C. After the solution was stirred for 3 days and kept standing to cool to room temperature, the solvent was evaporated in vacuo. The residue was purified by the silica gel column chromatography, and the compound 4 (285 mg) was obtained.

MS m/z 415 [M+H]+, APCI(+)

The compound 4 (20.2 mg) was dissolved in THF (1 ml), and at 0° C., pyridine (12 μl) and trifluoroacetic acid anhydride (17 μl) were added thereto. After the mixture was stirred at 0° C. for 1 h, water was added thereto, and then, the mixture was extracted with ethyl acetate. The organic layer was washed with a 1N-hydrochloric acid aqueous solution and then with a saturated saline, followed by drying with anhydrous sodium sulfate. After the solution was filtrated and concentrated, the residue was purified by the silica gel column chromatography, and the compound 5 (17.4 mg) was obtained.

MS m/z 397 [M+H]+, APCI(+)

Example 8

5-[3-(6-methoxypyridin-3-yl)-6-(trifluoromethyl)-3H-imidazo[4,5-b]pyridin-2-yl]pyrazine-2-carbonitrile

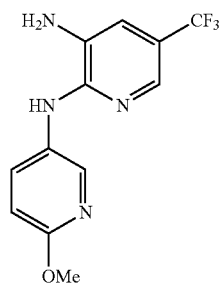

1

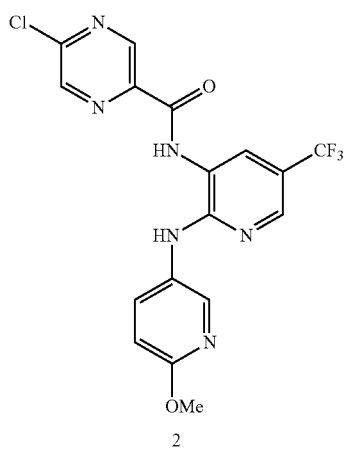

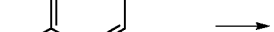

2

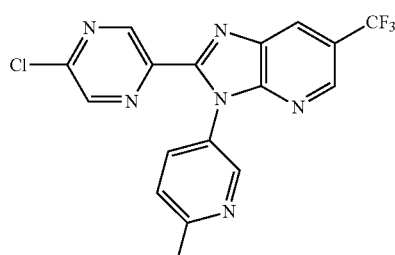

3

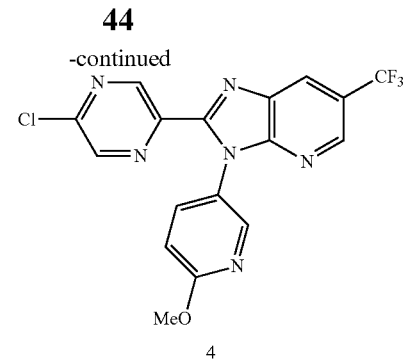

4

The compound 1 (the same as the compound described in Reference Example 4) (500 mg) was dissolved in methylene dichloride (9 ml), and was followed by addition of 5-chloropyrazine-2-carboxylic acid (293 mg) and EDCI-HCl (506 mg) thereto. After the mixture was stirred for 5 h, methylene dichloride, water and potassium carbonate were added thereto, and then, the organic layer was separated. After the organic layer was concentrated, the residue was purified by the silica gel column chromatography, and the compound 2 (548 mg) was obtained.

MS m/z 425/427 [M+H]+, APCI(+)

The compound 2 (548 mg) was dissolved in acetic acid (13 ml), and the solution was heated to 100° C. After the solution was stirred for 4 h, chloroform, water and potassium carbonate were added thereto, and then, the organic layer was separated. After the organic layer was concentrated, the residue was purified by the silica gel column chromatography, and the compound 3 (427 mg) was obtained.

MS m/z 407/409 [M+H]+, APCI(+)

After the compound 3 (150 mg) was dissolved in DMAC (3.7 ml), zinc cyanide (52 mg) and tetrakis(triphenylphosphine) palladium (0) (85 mg) were added thereto, and then, the reaction temperature was raised to 170° C. by irradiation of microwave. After the solution was stirred for 20 min and kept standing to cool to room temperature, water was added thereto and the mixture was extracted with ethyl acetate. The organic layer was washed with a saturated saline and dried with magnesium sulfate. After the organic layer was filtrated and concentrated, the residue was purified by the silica gel column chromatography, and the compound 5 (71 mg) was obtained.

MS m/z 398 [M+H]+, APCI(+)

Example 9

2-(6-methoxypyridazin-3-yl)-1-(6-methoxypyridin-3-yl)-5-(trifluoromethyl)-1H-benzimidazole

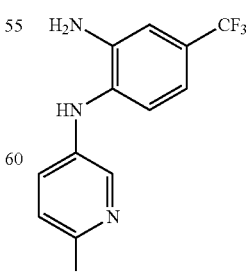

1

-continued

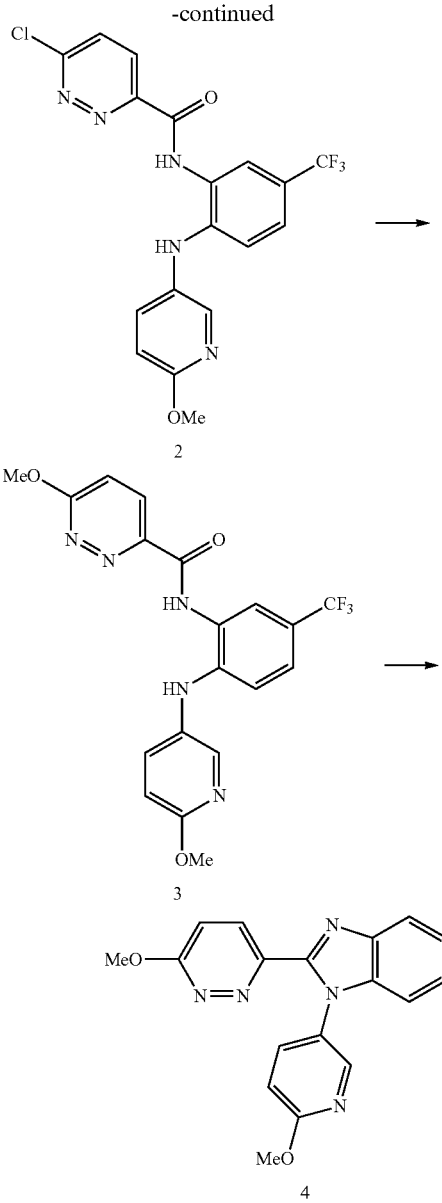

The compound 1 (the same as the compound described in Reference Example 1) (283 mg) was dissolved in DMF (3 ml), and 6-chloro-pyridazin-3-carboxylic acid (238 mg), HATU (760 mg) and diisopropylethylamine (348 μl) were added thereto. After the mixture was stirred all day and all night, water was added thereto, and then, the mixture was extracted with ethyl acetate. After the organic layer was washed sequentially with an aqueous 1N-sodium hydroxide solution, water and a saturated saline, the organic layer was dried with anhydrous sodium sulfate. After the organic layer was filtrated and concentrated, the residue was purified by the silica gel column chromatography, and the compound 2 (39.9 mg) was obtained.

MS m/z 424/426 [M+H]+, APCI(+)

After the compound 2 (24 mg) was dissolved in methanol (0.6 ml), a sodium methoxide methanol solution (0.2 ml) was added thereto, and the mixture was stirred at room temperature. After the mixture was stirred for 2 h, water was added thereto, and the mixture was extracted with ethyl acetate. The organic layer was washed with a saturated saline, and was dried with anhydrous sodium sulfate. After the organic layer was filtrated and concentrated, the residue was purified by the silica gel column chromatography, and the compound 3 (7.2 mg) was obtained.

MS m/z 420 [M+H]+, APCI(+)

The compound 3 (50.1 mg) was dissolved in acetic acid (1 ml), and heated at 100°. After the solution was stirred all day and all night, the solvent was evaporated in vacuo, and to the residue were added a saturated aqueous sodium bicarbonate solution and ethyl acetate. After the organic layer was separated, it was washed sequentially with water and a saturated saline, and was dried with anhydrous sodium sulfate. After the organic layer was filtrated and concentrated, the residue was purified by the silica gel column chromatography, and the compound 4 (44.4 mg) was obtained.

MS m/z 402 [M+H]+, APCI(+)

Example 10

3-(6-methoxypyridin-3-yl)-2-(1H-pyrrol-2-yl)-6-(trifluoromethyl)-3H-imidazo[4,5-b]pyridine

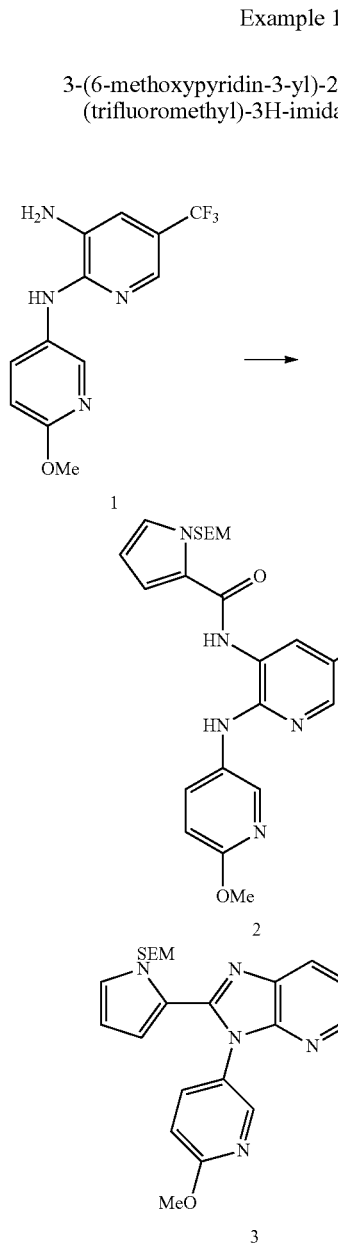

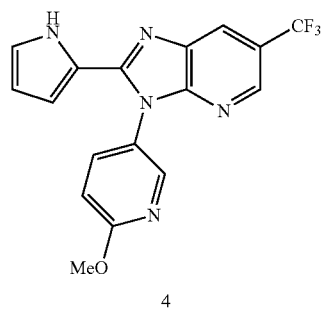

4

1-{[2-(Trimethylsilyl)ethoxy]methyl}-1H-pyrrol-2-carboxylic acid (362 mg) was dissolved in thionyl chloride (5 ml), and the mixture was refluxed for 30 min under heating. After the mixture was standing to cool to room temperature, the solvent was evaporated in vacuo. The residue was suspended in methylene dichloride (2 ml), and the suspended solution was added to a pyridine solution (5 ml) of the compound 1 (the same as the compound described in Reference Example 4) (284 mg). After the solution was stirred for 5 h, the solvent was evaporated in vacuo, and to the residue was added 1N-hydrochloric acid and ethyl acetate. The organic layer was washed sequentially with water and a saturated saline, and was dried with anhydrous sodium sulfate. After the organic layer was filtrated and concentrated, the residue was purified by the silica gel column chromatography, and the compound 2 (271 mg) was obtained.

MS m/z 508 [M+H]+, APCI(+)

The compound 2 (265 mg) was dissolved in acetic acid (2.7 ml), and the solution was heated to 100° C. After the solution was stirred all day and all night, the solvent was evaporated in vacuo, and the residue was purified by the silica gel column chromatography, and the compound 3 (236 mg) was obtained.

MS m/z 490[M+H]+, APCI(+)

After the compound 3 (235 mg) was dissolved in THF (5 ml), tetra-N-butylammonium fluoride (1 mol/L, 720 µl) was added thereto, and the solution was refluxed for 2 days under heating. After the solution was kept standing to cool to room temperature, an aqueous solution of saturated sodium bicarbonate was added thereto, and the mixture was extracted with ethyl acetate. After the organic layer was washed sequentially with water and a saturated saline, the organic layer was dried with anhydrous sodium sulfate. After the organic layer was filtrated and concentrated, the residue was purified by the silica gel column chromatography, and the compound 4 (121 mg) was obtained.

MS m/z 360[M+H]+, APCI(+)

Example 11

2-(1H-Imidazol-4-yl)-3-(6-methoxypyridin-3-yl)-6-(trifluoromethyl)-3H-imidazo[4,5-b]pyridine

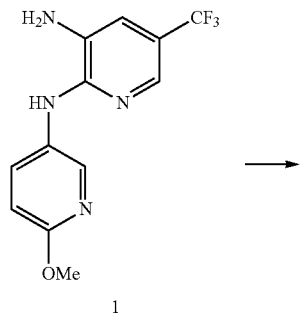

1

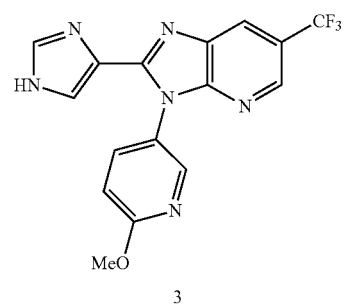

2

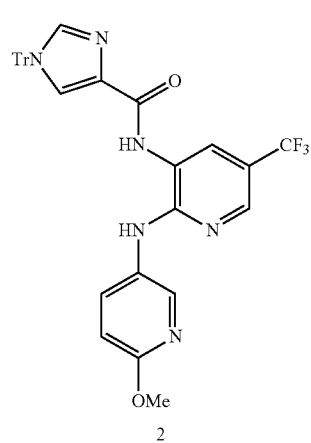

3

After the compound 1 (the same as the compound described in Reference Example 4) (199 mg) was dissolved in DMF (3 ml), 1-trityl-1H-imidazol-4-carboxylic acid (298 mg), EDCI-HCl (174 mg), HOBt-H₂O (139 mg) and diisopropylethylamine (146 µl) were added thereto, and the mixture was heated to 60° C. After the mixture was stirred for 3 days, water was added thereto, and the mixture was extracted with ethyl acetate. The organic layer was washed sequentially with an aqueous 1N-sodium hydroxide solution, water and a saturated saline, and was then dried with anhydrous sodium sulfate. After the organic layer was filtrated and concentrated, the residue was purified by the silica gel column chromatography, and the compound 2 (318 mg) was obtained.

MS m/z 621 [M+H]+, ESI

The compound 2 (315 mg) was dissolved in acetic acid (4.5 ml), and the solution was heated to 100° C. After the solution was stirred for 2 days and kept standing to cool to room temperature, the solvent was evaporated in vacuo. The evaporated residue was dissolved in methylene dichloride (1 ml), and at 0° C., trifluoroacetic acid (1 ml) was added thereto. After the solution was stirred at room temperature for 8 h, the solvent was evaporated in vacuo. The residue was purified by the silica gel column chromatography, and the compound 3 (175 mg) was obtained.

MS m/z 361[M+H]+, APCI(+)

Example 12

1,2-Dipyridin-2-yl-5-(trifluoromethyl)-1H-benzimidazole

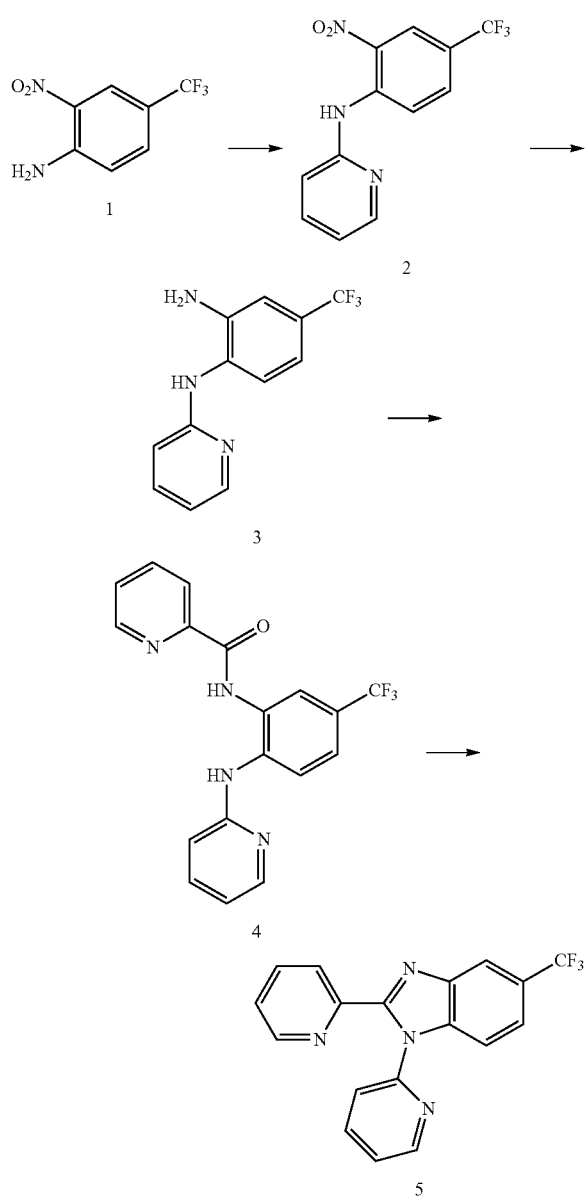

After 4-amino-3-nitrobenzenetrifluoride (2.06 g) was dissolved in 1,2-dimethoxyethane (20 ml), 2-bromopyridine (1.58 g), tris(dibenzylidene acetone)dipalladium (0) (458 mg), 2-dicyclohexylphosphino-2',4',6'-triisopropylbiphenyl (394 mg) and potassium phosphate (3.18 g) were added thereto, and the mixture solution was heated to 100°. After the solution was stirred all day and all night and was kept standing to cool to room temperature, the insoluble material was filtrated. To the filtrate was added water, and was extracted with ethyl acetate. The organic layer was washed with a saturated saline, and was dried with anhydrous sodium sulfate. After the organic layer was filtrated and concentrated, the concentrated residue was purified by the silica gel column chromatography, and the compound 2 (1.23 g) was obtained.

MS m/z 284 [M+H]+, APCI(+)

The compound 2 (1.22 g) was dissolved in methanol (12 ml), and iron (III) chloride (69.9 mg), hydrazine monohydrate (1.08 g) and active carbon (120 mg) were added thereto, and then, the mixture was refluxed for 2 h under heating. After the mixture was kept standing to cool to room temperature, the insoluble material was filtrated. After the filtrate was concentrated, to the concentrated residue was added chloroform and the obtained solution was dried with anhydrous sodium sulfate. After the solution was filtrated and concentrated, the concentrated residue was purified by the silica gel column chromatography, and the compound 3 (0.89 g) was obtained.

MS m/z 254 [M+H]+, APCI(+)

The compound 3 (120 mg) was dissolved in DMF (1.2 ml), and picolinic acid (61.8 mg), HATU (255 mg) and diisopropylethylamine (117 μl) were added thereto. After the solution was stirred for 2 days, water was added thereto and extracted with ethyl acetate. The organic layer was washed sequentially with an aqueous solution saturated with sodium bicarbonate, water and saturated saline, and then, the organic layer was dried with anhydrous sodium sulfate. After the organic layer was filtrated and concentrated, the concentrated residue was purified by the silica gel column chromatography, and the compound 4 (165 mg) was obtained.

MS m/z 359 [M+H]+, APCI(+)

The compound 4 (160 mg) was dissolved in acetic acid (1.5 ml) and heated to 100° C. After the solution was stirred for 10 h and was kept standing to cool to room temperature, and the solvent was evaporated in vacuo. The evaporated residue was dissolved in ethyl acetate, and after the organic layer was washed sequentially with an aqueous sodium bicarbonate solution and a saturated saline, the organic layer was dried with anhydrous sodium sulfate. After the organic layer was filtrated and concentrated, the concentrated residue was purified by the silica gel column chromatography, and the compound 5 (104 mg) was obtained.

MS m/z 341[M+H]+, APCI(+)

Example 13

3-(6-methoxypyridin-3-yl)-2-pyridin-2-yl-6-(trifluoromethyl)-3H-imidazo[4,5-b]pyridine

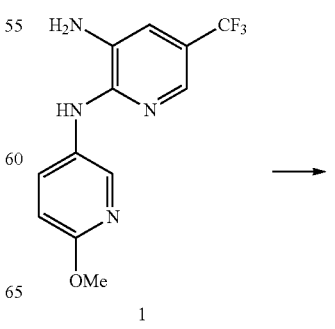

1

-continued

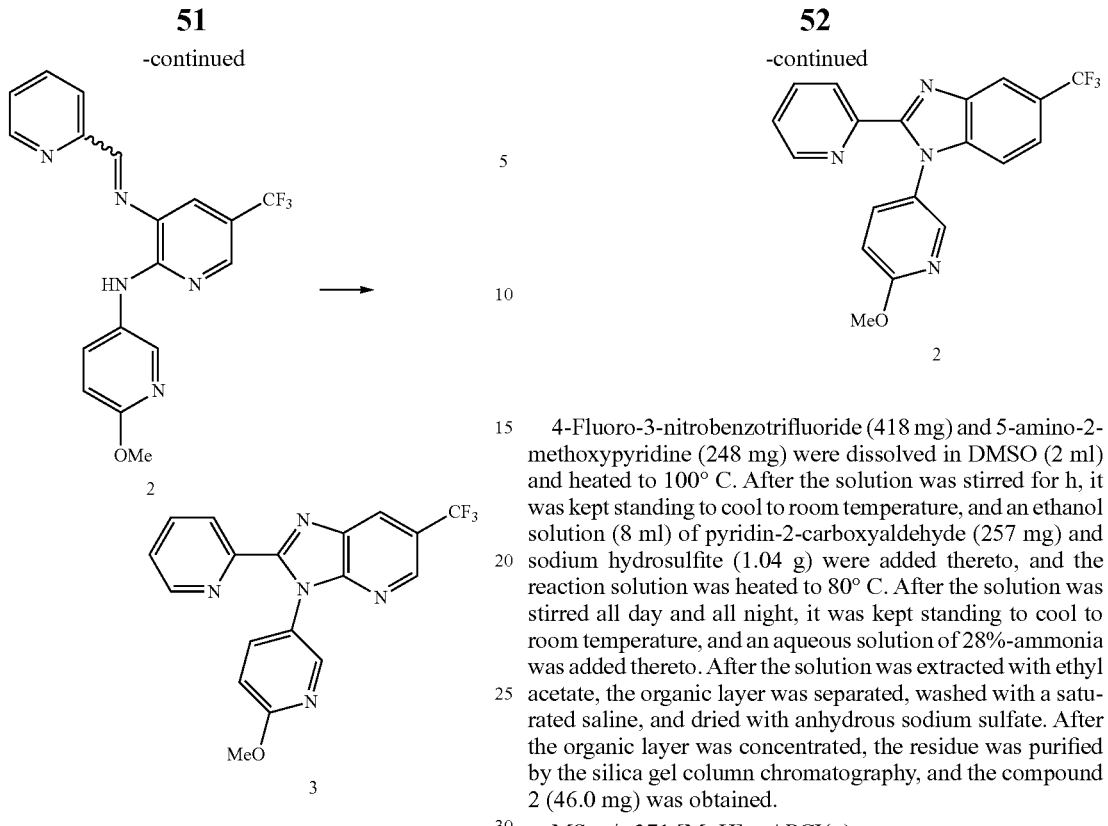

The compound 1 (the same as the compound of Reference Example 4) (64.0 mg) was dissolved in ethanol (3 ml), and 2-pyridinecarboxyaldehyde (29.0 mg) was added thereto, and then, the solution was heated to 80° C. The solution was stirred for 20 h and allowed to cool to room temperature. After the solvent was evaporated in vacuo, the compound 2 (61.1 mg) was obtained.

MS m/z 374 [M+H]+, APCI(+)

After the compound 2 (57.0 mg) was dissolved in DMF (1.5 ml), and was added acetic acid (0.2 ml) thereto, the solution was heated to 80° C. After the solution was stirred for 4 h and allowed to cool to room temperature, the solvent was evaporated in vacuo. To the evaporated residue was added an aqueous solution saturated with sodium bicarbonate, and the solution was extracted with ethyl acetate. After the organic layer was concentrated, the residue was purified by the silica gel column chromatography, and the compound 3 (38.0 mg) was obtained.

MS m/z 372 [M+H]+, APCI(+)

Example 14

1-(6-methoxypyridin-3-yl)-2-pyridin-2-yl-5-(trifluoromethyl)-1H-benzimidazole

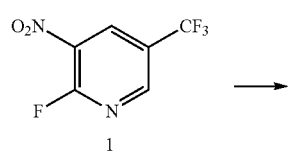

-continued

4-Fluoro-3-nitrobenzotrifluoride (418 mg) and 5-amino-2-methoxypyridine (248 mg) were dissolved in DMSO (2 ml) and heated to 100° C. After the solution was stirred for h, it was kept standing to cool to room temperature, and an ethanol solution (8 ml) of pyridin-2-carboxyaldehyde (257 mg) and sodium hydrosulfite (1.04 g) were added thereto, and the reaction solution was heated to 80° C. After the solution was stirred all day and all night, it was kept standing to cool to room temperature, and an aqueous solution of 28%-ammonia was added thereto. After the solution was extracted with ethyl acetate, the organic layer was separated, washed with a saturated saline, and dried with anhydrous sodium sulfate. After the organic layer was concentrated, the residue was purified by the silica gel column chromatography, and the compound 2 (46.0 mg) was obtained.

MS m/z 371 [M+H]+, APCI(+)

Example 15

1-(6-methoxypyridazin-3-yl)-2-(1-methyl-1H-pyrazol-4-yl)-5-(trifluoromethyl)-1H-benzimidazole

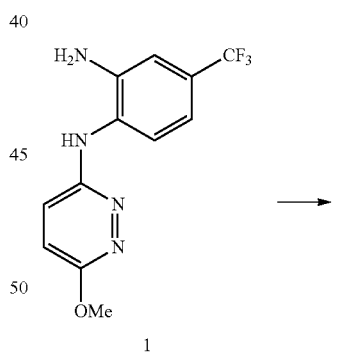

53

-continued

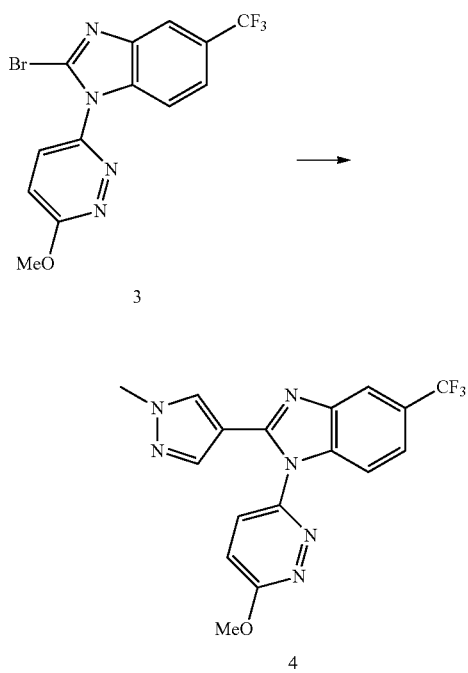

To the compound 1 (3.5 g) were added triethyl orthoformate (20.5 ml) and trifluoroacetic acid (0.1 ml), and the mixture solution was stirred at room temperature for 3 h. To the solution was added ethyl acetate, and the organic layer was washed sequentially with an aqueous solution saturated with sodium bicarbonate and a saturated saline, and dried with anhydrous sodium sulfate. After the organic layer was filtrated and concentrated, diethyl ether was added to the concentrated residue, and the compound 2 (3.37 g) was obtained as a precipitate after filtration.

MS m/z 295 [M+H]+, APCI(+)

The compound 2 (500 mg) was dissolved in dioxane (10 ml), and N-bromosuccinimide (696 mg) was added thereto, and the solution was heated to 100° C. After the solution was stirred for 30 min, the solvent was evaporated in vacuo. The evaporated residue was purified by the silica gel column chromatography, and the compound 3 (223 mg) was obtained.

MS m/z 373/375 [M+H]+, APCI(+)

Under an argon atmosphere, to a DMF (4 ml) solution of the compound 3 (200 mg) were added 1-methyl-4-(4,4,5,5-tetramethyl-1,3,2-dioxaboran-2-yl)-1H-pyrazole (185 mg), potassium phosphate (142 mg) and tetrakis (triphenylphosphine) palladium (0) (51.3 mg), and then, the mixture solution was heated to 100° C. After the solution was stirred for 7 h and kept standing to cool to room temperature, an insoluble material was filtrated. To the filtrate was added a saturated saline, and the solution was extracted with ethyl acetate. After the organic layer was concentrated, the residue was purified by the silica gel column chromatography, and the compound 4 (135 mg) was obtained.

MS m/z 375 [M+H]+, APCI(+)

54

Example 16

5-bromo-1-(6-methoxypyridin-3-yl)-2-pyridin-2-yl-1H-benzimidazole

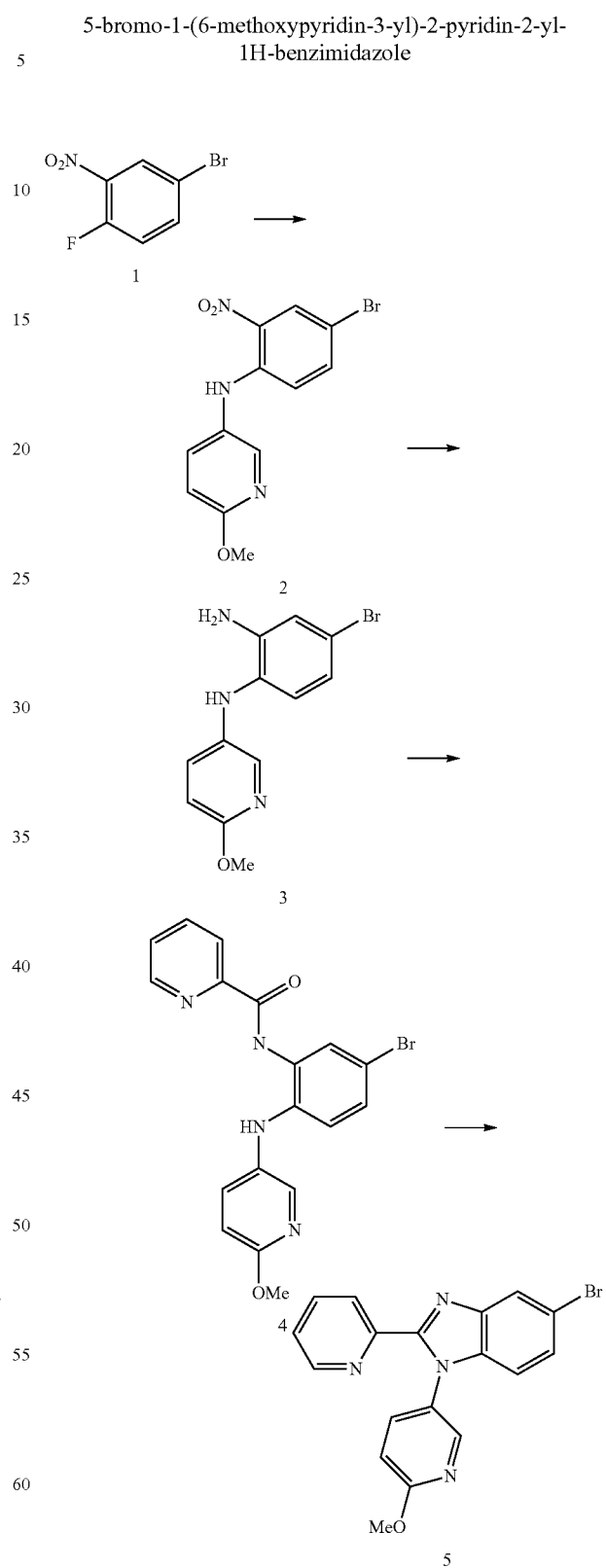

To a DMSO (40 ml) solution of 4-bromo-1-fluoro-2-nitrobenzene (5 g) was added 5-amino-2-methoxypyridine (6.33 g), and the solution was heated to 100° C. After the solution was stirred for 20 h, it was kept standing to cool to room temperature, and water (120 ml) and an aqueous solution saturated with sodium bicarbonate (40 ml) were added thereto. The compound 2 (7.03 g) was obtained as a precipitate by filtration.

MS m/z 324/326 [M+H]+, APCI(+)

To a methanol (15 ml) solution of the compound 2 (1 g), were added active carbon (121 mg), iron (III) chloride (24.3 mg) and hydrazine monohydrate (0.75 ml), and the mixture was refluxed under heating for 2 h. After the mixture was kept standing to cool to room temperature, an insoluble material was filtrated. After the filtrate was concentrated, n-heptane was added to the residue, and the crude product (0.93 g) of the compound 3 was obtained as a precipitate by filtration. To a pyridine (16 ml) solution of the obtained crude product (0.93 g) of the compound 3, picolinic acid chloride-hydrochloride (1.13 g) was added and stirred at room temperature for 2 h. After the solvent was distilled off in vacuo, to the residue was added an aqueous solution saturated with sodium bicarbonate, and the solution was extracted with chloroform. The organic layer was washed with a saturated saline and dried with anhydrous sodium sulfate. After the organic layer was filtrated and concentrated, the residue was purified by the silica gel column chromatography, and the compound 4 (0.88 g) was obtained. The compound 4 (0.88 g) was dissolved in acetic acid (10 ml) and was heated to 80° C. After the solution was stirred all day and all night, it was kept standing to cool to room temperature, and then, the solvent was distilled off in vacuo. Chloroform was added to the residue, and the solution was dried with an aqueous solution saturated with sodium bicarbonate. After the organic layer was filtrated and concentrated, the residue was purified by the silica gel column chromatography, and the compound 5 (0.82 g) was obtained.

MS m/z 381/383 [M+H]+, APCI(+)

Example 17

5-ethyl-1-(6-methoxypyridin-3-yl)-2-pyridin-2-yl-1H-benzimidazole

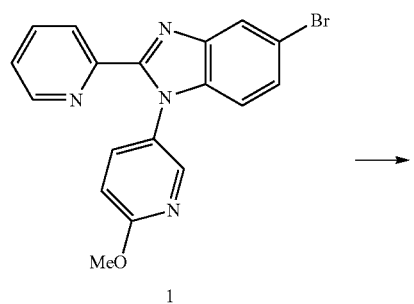

1

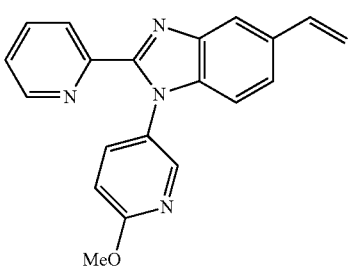

2

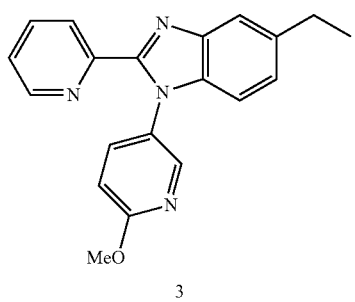

3 compound 1 (the same compound as described in Example 16) (100 mg) ⑦ To a 1,2-dimethoxyethane/water (2.86 ml, 10/1) solution were added potassium vinyltrifluoroborate (69.1 mg), tetrakis-triphenylphosphine palladium (0) (30 mg) and cesium carbonate (126.8 mg), and the mixture was heated to 100° C. After the mixture was stirred for 18 h, it was kept standing to cool to room temperature, and then, an insoluble material was filtrated. After the filtrate was concentrated, the residue was purified by the silica gel column chromatography, and the compound 2 (54.5 mg) was obtained.

MS m/z 329 [M+H]+, APCI(+)

To a THF (2 ml) solution of the compound 2 (32.5 mg), a 10% palladium-carbon (3 mg) was added, and under a hydrogen atmosphere, the solution was stirred at room temperature for 3 h. After an insoluble material was filtrated, the filtrate was concentrated, and the residue was purified by the silica gel column chromatography, and the compound 3 (31.4 mg) was obtained.

MS m/z 331 [M+H]+, APCI(+)

The following compounds were produced according to the Production Methods 1-5 and the above Examples.

TABLE 1

| Example 18 | | MS: 370 [M + H]+ APCI |
|---|---|---|
| 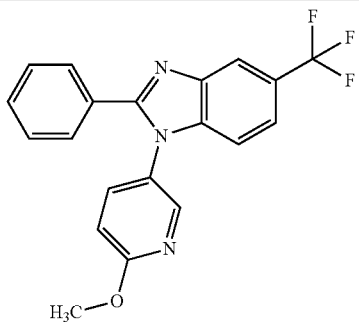 [SMILES: COc1ccc(-n2c(-c3ccccc3)nc3cc(C(F)(F)F)ccc32)cn1] | | |

TABLE 1-continued
| | | |
|---|---|---|
| Example 19 | 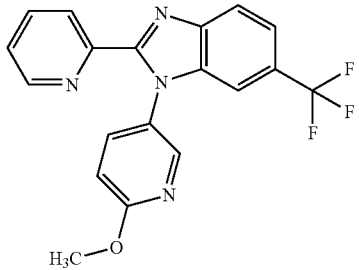 [SMILES: COc1ccc(-n2c(-c3ccccn3)nc3ccc(C(F)(F)F)cc32)cn1] | MS: 371 [M + H]+ APCI |
| Example 20 | 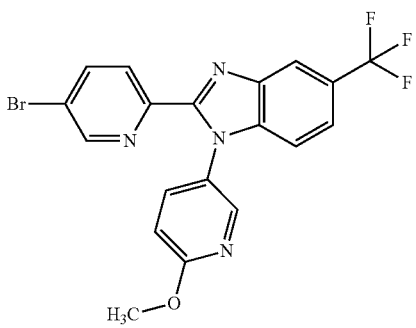 [SMILES: COc1ccc(-n2c(-c3ccc(Br)cn3)nc3cc(C(F)(F)F)ccc32)cn1] | MS: 449/451 [M + H]+ APCI |
| Example 21 | 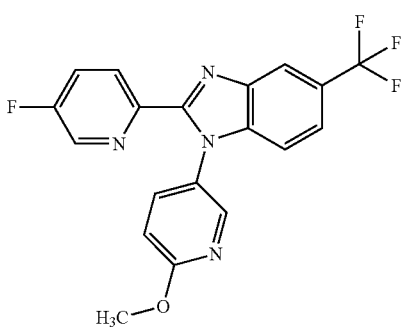 | MS: 389 [M + H]+ APCI |
| Example 22 | 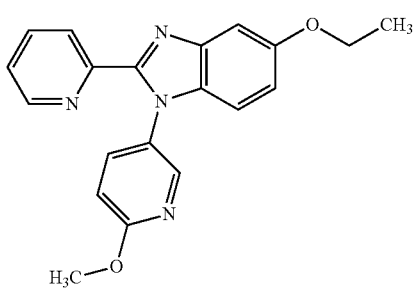 [SMILES: CCOc1ccc2c(c1)nc(-c1ccccn1)n2-c1ccc(OC)nc1] | MS: 347 [M + H]+ APCI |
| Example 23 | 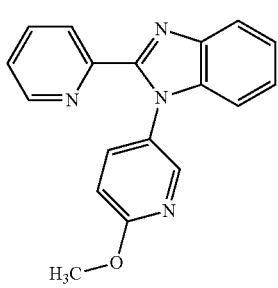 [SMILES: COc1ccc(-n2c(-c3ccccn3)nc3ccccc32)cn1] | MS: 303 [M + H]+ APCI |

TABLE 1-continued
| | | |
|---|---|---|
| Example 24 | 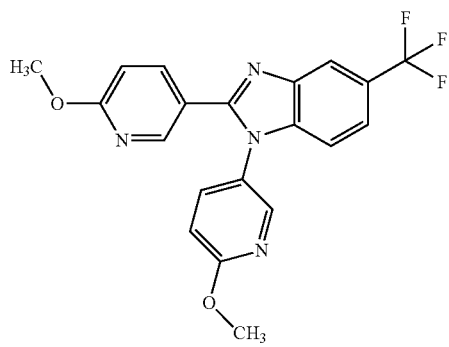 [SMILES: COc1ccc(-c2nc3cc(C(F)(F)F)ccc3n2-c2ccc(OC)nc2)cn1] | MS: 401 [M + H]+ APCI |
| Example 25 | 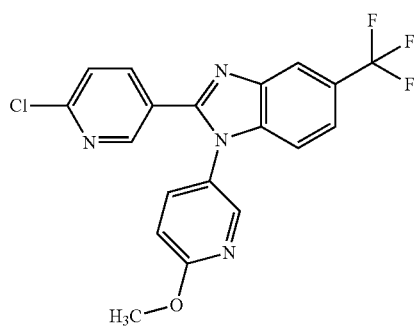 [SMILES: COc1ccc(-n2c(-c3ccc(Cl)nc3)nc3cc(C(F)(F)F)ccc32)cn1] | MS: 405/407 [M + H]+ APCI |
| Example 26 | 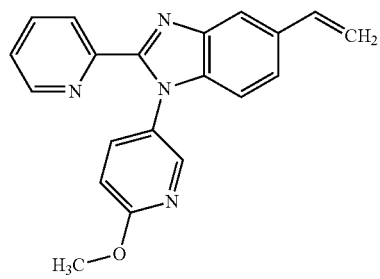 [SMILES: C=Cc1ccc2c(c1)nc(-c1ccccn1)n2-c1ccc(OC)nc1] | MS: 329 [M + H]+ APCI |
| Example 27 | 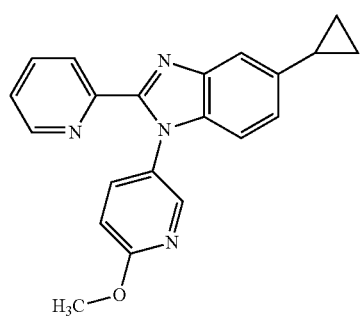 [SMILES: COc1ccc(-n2c(-c3ccccn3)nc3cc(C4CC4)ccc32)cn1] | MS: 343 [M + H]+ APCI |
| Example 28 | 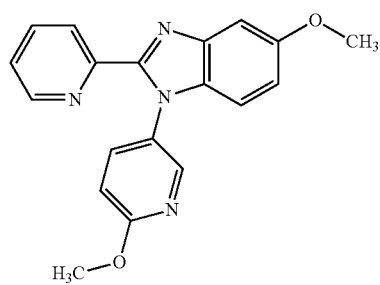 [SMILES: COc1ccc2c(c1)nc(-c1ccccn1)n2-c1ccc(OC)nc1] | MS: 333 [M + H]+ APCI |

TABLE 1-continued
| | | |
|---|---|---|
| Example 29 | 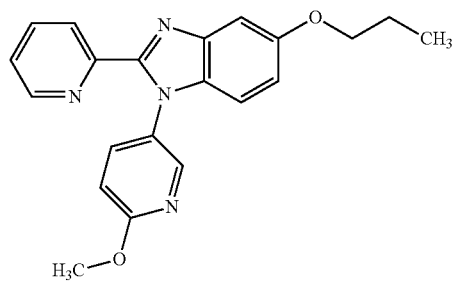 [SMILES: CCCOc1ccc2c(c1)nc(-c1ccccn1)n2-c1ccc(OC)nc1] | MS: 361 [M + H]+ APCI |
| Example 30 | 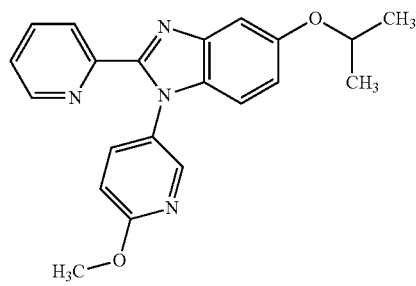 [SMILES: COc1ccc(-n2c(-c3ccccn3)nc3cc(OC(C)C)ccc32)cn1] | MS: 361 [M + H]+ APCI |
| Example 31 | 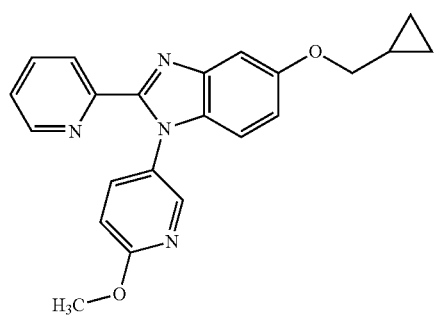 [SMILES: COc1ccc(-n2c(-c3ccccn3)nc3cc(OCC4CC4)ccc32)cn1] | MS: 373 [M + H]+ APCI |
| Example 32 | 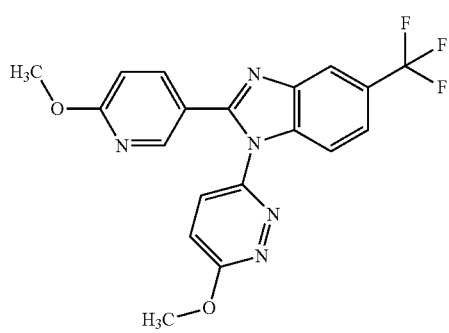 | MS: 402 [M + H]+ APCI |
| Example 33 | 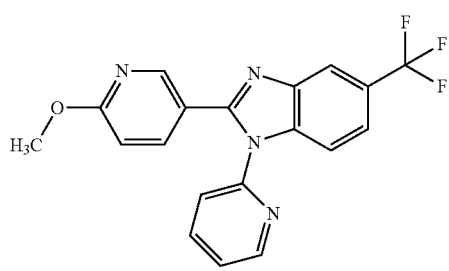 [SMILES: COc1ccc(-c2nc3cc(C(F)(F)F)ccc3n2-c2ccccn2)cn1] | MS: 371 [M + H]+ APCI |

TABLE 1-continued
| Example 34 | 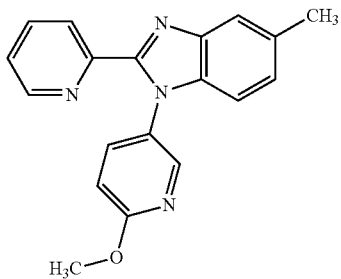 [SMILES: COc1ccc(-n2c(-c3ccccn3)nc3cc(C)ccc32)cn1] | MS: 317 [M + H]+ APCI |
| Example 35 | 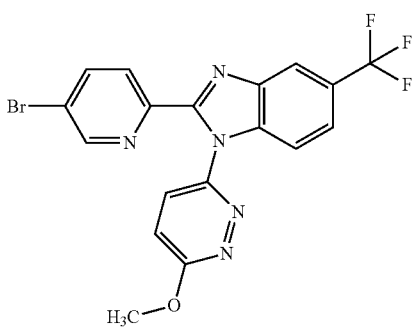 | MS: 450/452 [M + H]+ APCI |
| Example 36 | 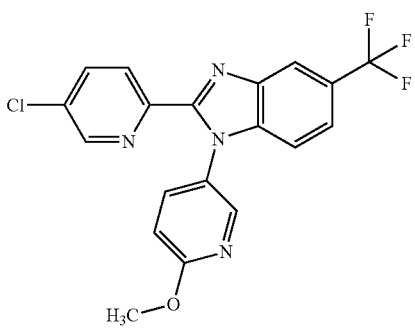 [SMILES: COc1ccc(-n2c(-c3ccc(Cl)cn3)nc3cc(C(F)(F)F)ccc32)cn1] | MS: 405/407 [M + H]+ APCI |
| Example 37 | 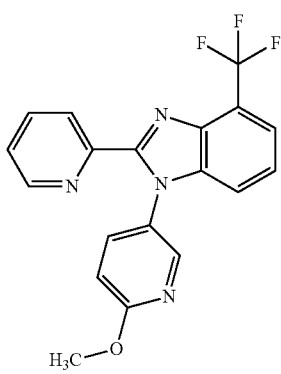 [SMILES: COc1ccc(-n2c(-c3ccccn3)nc3c(C(F)(F)F)cccc32)cn1] | MS: 371 [M + H]+ APCI |
| Example 38 | 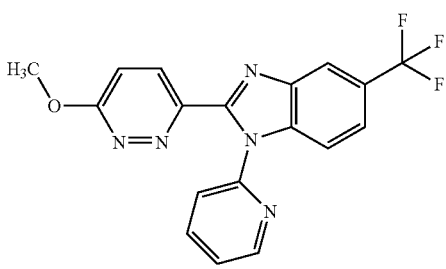 [SMILES: COc1ccc(-c2nc3cc(C(F)(F)F)ccc3n2-c2ccccn2)nn1] | MS: 372 [M + H]+ APCI |

TABLE 1-continued
| Example 39 | 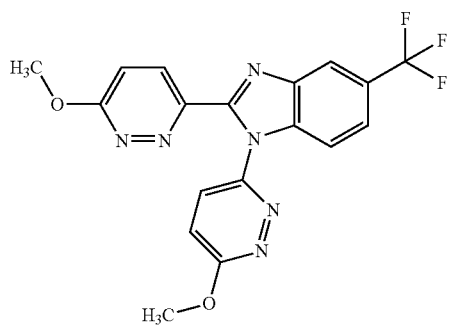 | MS: 403 [M + H]+ APCI |
| Example 40 | 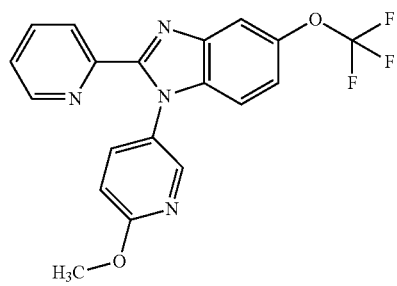 | MS: 387 [M + H]+ APCI |
| Example 41 | 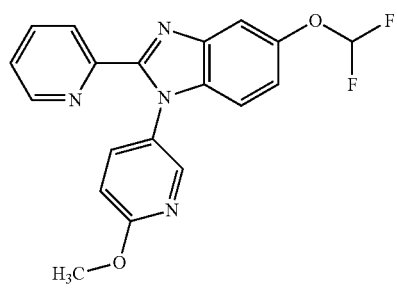 [SMILES: COc1ccc(-n2c(-c3ccccn3)nc3cc(OC(F)F)ccc32)cn1] | MS: 369 [M + H]+ APCI |
| Example 42 | 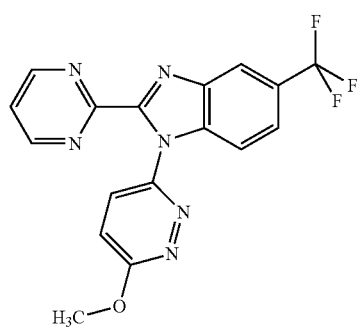 [SMILES: COc1ccc(-n2c(-c3ncccn3)nc3cc(C(F)(F)F)ccc32)nn1] | MS: 373 [M + H]+ APCI |
| Example 43 | 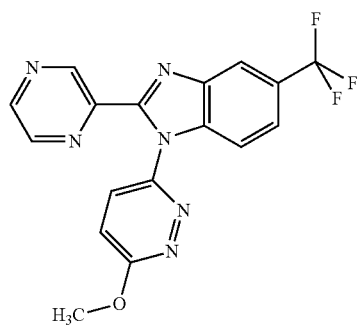 [SMILES: COc1ccc(-n2c(-c3cnccn3)nc3cc(C(F)(F)F)ccc32)nn1] | MS: 373 [M + H]+ APCI |

TABLE 1-continued
| | | |
|---|---|---|
| Example 44 | 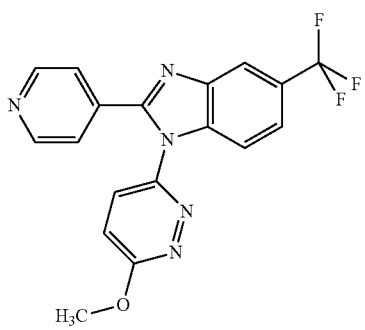 [SMILES: COc1ccc(-n2c(-c3ccncc3)nc3cc(C(F)(F)F)ccc32)nn1] | MS: 372 [M + H]+ APCI |
| Example 45 | 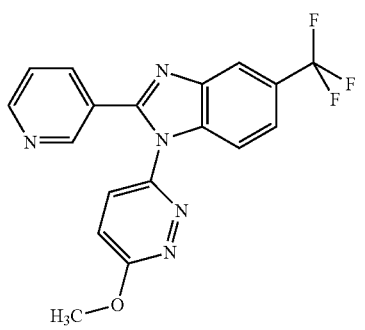 | MS: 372 [M + H]+ APCI |
| Example 46 | 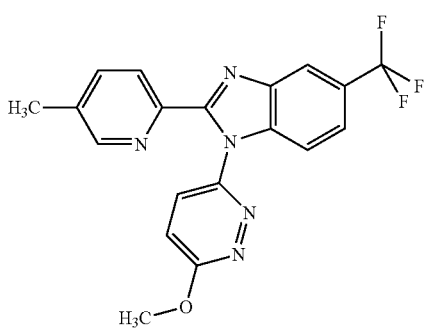 [SMILES: COc1ccc(-n2c(-c3ccc(C)cn3)nc3cc(C(F)(F)F)ccc32)nn1] | MS: 386 [M + H]+ APCI |
| Example 47 | 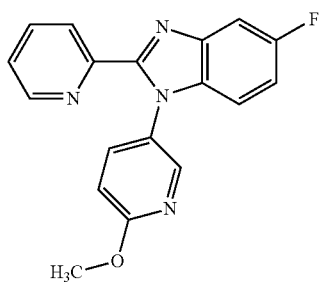 [SMILES: COc1ccc(-n2c(-c3ccccn3)nc3cc(F)ccc32)cn1] | MS: 321 [M + H]+ APCI |
| Example 48 | 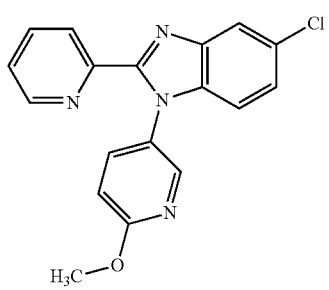 [SMILES: COc1ccc(-n2c(-c3ccccn3)nc3cc(Cl)ccc32)cn1] | MS: 337/339 [M + H]+ APCI |

TABLE 1-continued
| Example 49 | 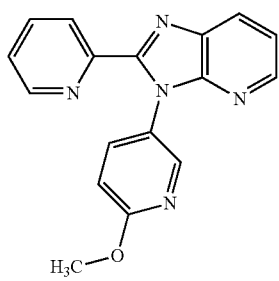 [SMILES: COc1ccc(-n2c(-c3ccccn3)nc3cccnc32)cn1] | MS: 304 [M + H]+ APCI |
| Example 50 | 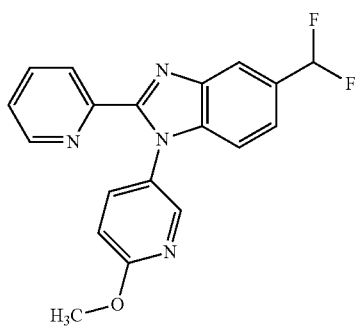 [SMILES: COc1ccc(-n2c(-c3ccccn3)nc3cc(C(F)F)ccc32)cn1] | MS: 353 [M + H]+ APCI |
| Example 51 | 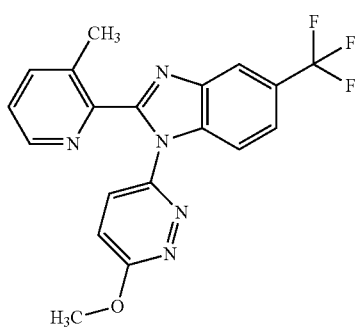 [SMILES: COc1ccc(-n2c(-c3ncccc3C)nc3cc(C(F)(F)F)ccc32)nn1] | MS: 386 [M + H]+ APCI |
| Example 52 | 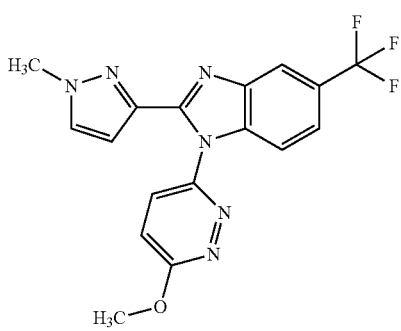 [SMILES: COc1ccc(-n2c(-c3ccn(C)n3)nc3cc(C(F)(F)F)ccc32)nn1] | MS: 375 [M + H]+ APCI |
| Example 53 | 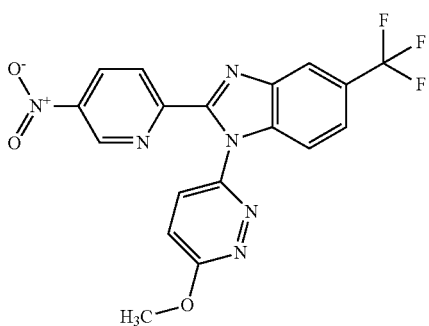 [SMILES: COc1ccc(-n2c(-c3ccc([N+](=O)[O-])cn3)nc3cc(C(F)(F)F)ccc32)nn1] | MS: 417 [M + H]+ APCI |

TABLE 1-continued
| | | |
|---|---|---|
| Example 54 | 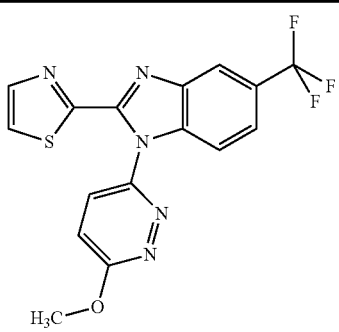 | MS: 378 [M + H]+ APCI |
| Example 55 | 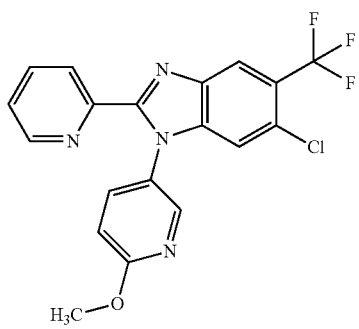 [SMILES: COc1ccc(-n2c(-c3ccccn3)nc3cc(C(F)(F)F)c(Cl)cc32)cn1] | MS: 405/407 [M + H]+ APCI |
| Example 56 | 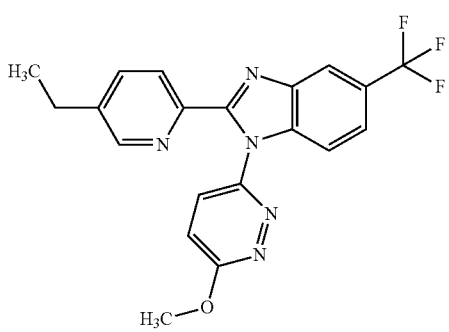 | MS: 400 [M + H]+ APCI |
| Example 57 | 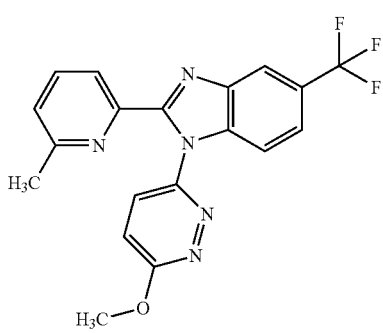 [SMILES: COc1ccc(-n2c(-c3cccc(C)n3)nc3cc(C(F)(F)F)ccc32)nn1] | MS: 386 [M + H]+ APCI |
| Example 58 | 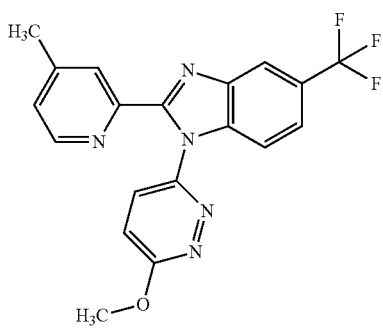 [SMILES: COc1ccc(-n2c(-c3cc(C)ccn3)nc3cc(C(F)(F)F)ccc32)nn1] | MS: 386 [M + H]+ APCI |

TABLE 1-continued
Example 59
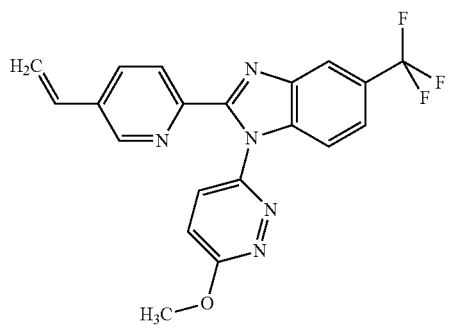 [SMILES: C=Cc1ccc(-c2nc3cc(C(F)(F)F)ccc3n2-c2ccc(OC)nn2)nc1]
MS: 398 [M + H]+ APCI
Example 60
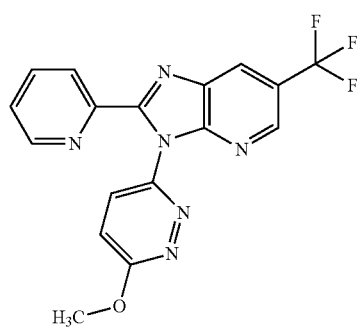 [SMILES: COc1ccc(-n2c(-c3ccccn3)nc3cc(C(F)(F)F)cnc32)nn1]
MS: 373 [M + H]+ APCI
Example 61
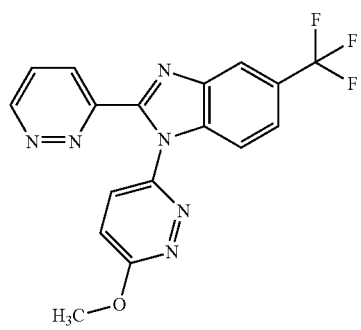 [SMILES: COc1ccc(-n2c(-c3cccnn3)nc3cc(C(F)(F)F)ccc32)nn1]
MS: 373 [M + H]+ APCI
Example 62
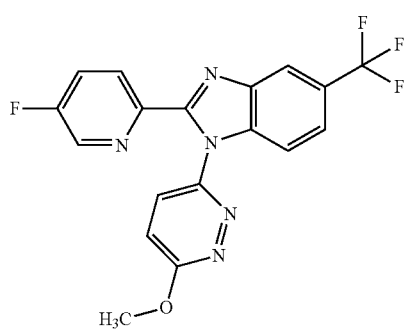
MS: 390 [M + H]+ APCI
Example 63
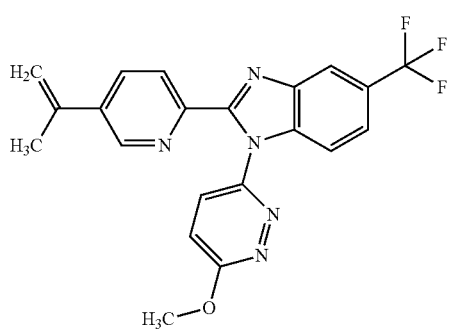 [SMILES: C=C(C)c1ccc(-c2nc3cc(C(F)(F)F)ccc3n2-c2ccc(OC)nn2)nc1]
MS: 412 [M + H]+ APCI TABLE 1-continued
Example 64 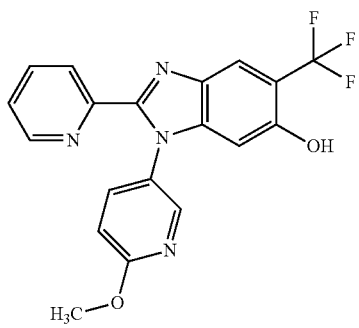 [SMILES: COc1ccc(-n2c(-c3ccccn3)nc3cc(C(F)(F)F)c(O)cc32)cn1]
MS: 387 [M + H]+ APCI
Example 65 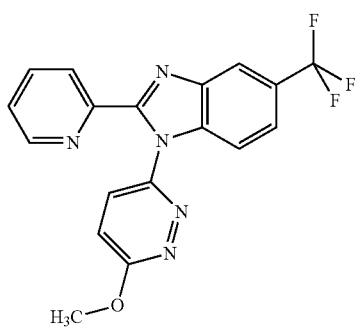 [SMILES: COc1ccc(-n2c(-c3ccccn3)nc3cc(C(F)(F)F)ccc32)nn1]
MS: 356 [M + H]+ APCI
Example 66 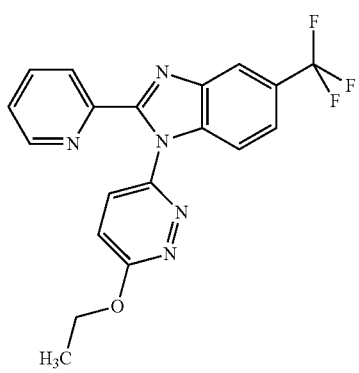 [SMILES: CCOc1ccc(-n2c(-c3ccccn3)nc3cc(C(F)(F)F)ccc32)nn1]
MS: 386 [M + H]+ APCI
Example 67 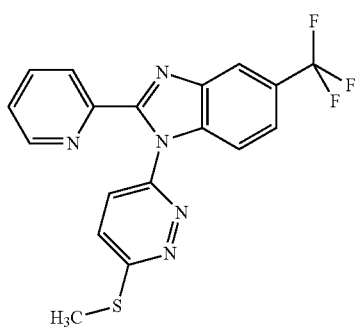
MS: 388 [M + H]+ APCI TABLE 1-continued
| | | |
|---|---|---|
| Example 68 | 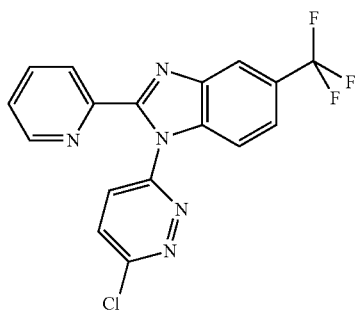 [SMILES: FC(F)(F)c1ccc2c(c1)nc(-c1ccccn1)n2-c1ccc(Cl)nn1] | MS: 376/378 [M + H]+ APCI |
| Example 69 | 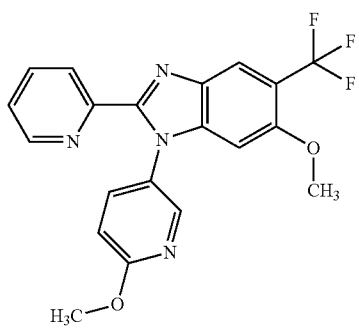 [SMILES: COc1ccc(-n2c(-c3ccccn3)nc3cc(C(F)(F)F)c(OC)cc32)cn1] | MS: 401 [M + H]+ APCI |
| Example 70 | 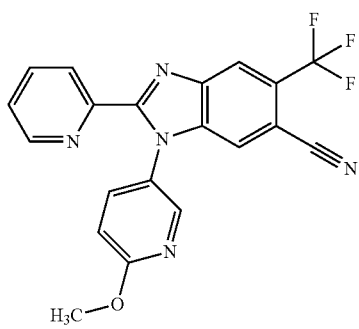 [SMILES: COc1ccc(-n2c(-c3ccccn3)nc3cc(C(F)(F)F)c(C#N)cc32)cn1] | MS: 396 [M + H]+ APCI |
| Example 71 | 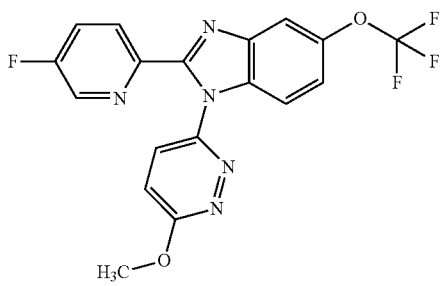 [SMILES: COc1ccc(-n2c(-c3ccc(F)cn3)nc3cc(OC(F)(F)F)ccc32)nn1] | MS: 406 [M + H]+ APCI |
| Example 72 | 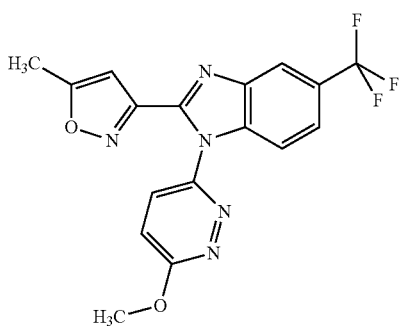 [SMILES: COc1ccc(-n2c(-c3cc(C)on3)nc3cc(C(F)(F)F)ccc32)nn1] | MS: 376 [M + H]+ APCI |

TABLE 1-continued
Example 73 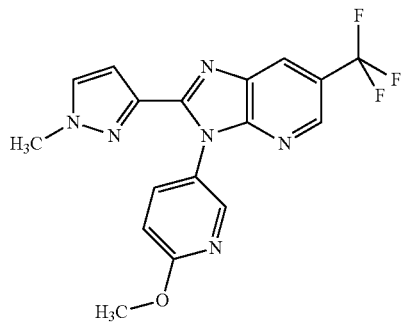 [SMILES: COc1ccc(-n2c(-c3ccn(C)n3)nc3cc(C(F)(F)F)cnc32)cn1]
MS: 375 [M + H]+ APCI
Example 74 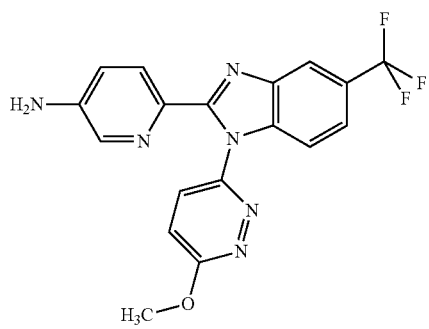
MS: 387 [M + H]+ APCI
Example 75 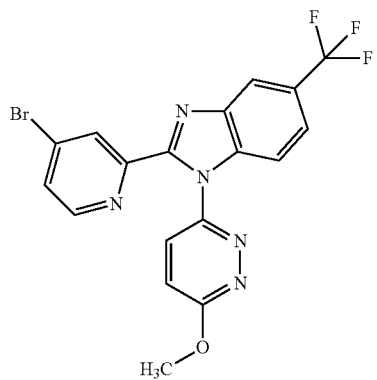 [SMILES: COc1ccc(-n2c(-c3cc(Br)ccn3)nc3cc(C(F)(F)F)ccc32)nn1]
MS: 450/452 [M + H]+ APCI
Example 76 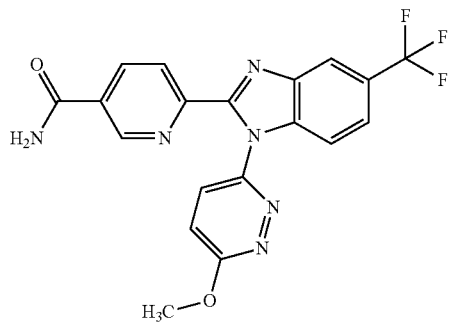 [SMILES: COc1ccc(-n2c(-c3ccc(C(N)=O)cn3)nc3cc(C(F)(F)F)ccc32)nn1]
MS: 415 [M + H]+ APCI TABLE 1-continued
Example 77
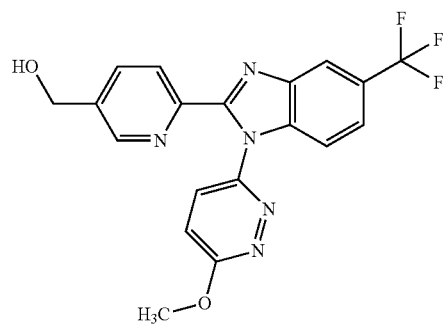 [SMILES: COc1ccc(-n2c(-c3ccc(CO)cn3)nc3cc(C(F)(F)F)ccc32)nn1]
MS: 402 [M + H]+ APCI
Example 78
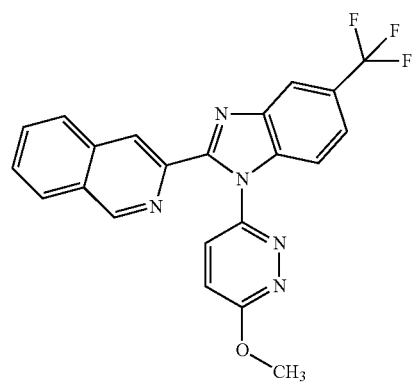 [SMILES: COc1ccc(-n2c(-c3cc4ccccc4cn3)nc3cc(C(F)(F)F)ccc32)nn1]
MS: 422 [M + H]+ APCI
Example 79
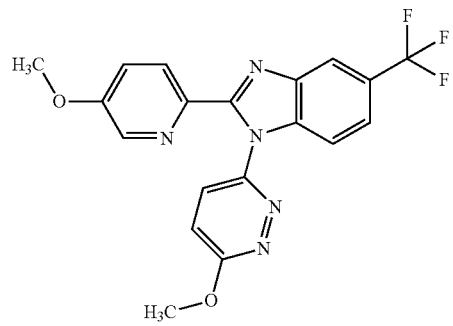 [SMILES: COc1ccc(-c2nc3cc(C(F)(F)F)ccc3n2-c2ccc(OC)nn2)nc1]
MS: 402 [M + H]+ APCI
Example 80
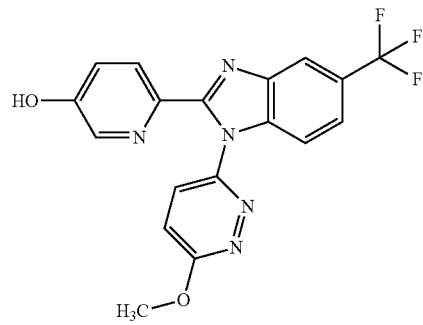 [SMILES: COc1ccc(-n2c(-c3ccc(O)cn3)nc3cc(C(F)(F)F)ccc32)nn1]
MS: 388 [M + H]+ APCI TABLE 1-continued
| Example 81 | 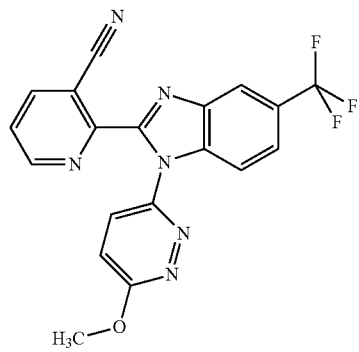 [SMILES: COc1ccc(-n2c(-c3ncccc3C#N)nc3cc(C(F)(F)F)ccc32)nn1] | MS: 397 [M + H]+ APCI |
| Example 82 | 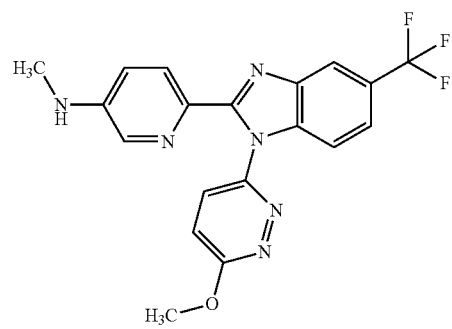 | MS: 401 [M + H]+ APCI |
| Example 83 | 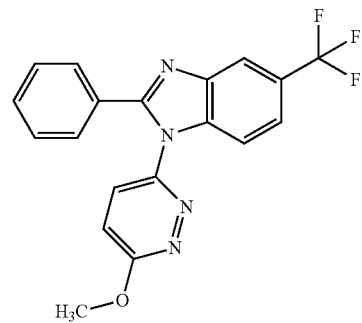 [SMILES: COc1ccc(-n2c(-c3ccccc3)nc3cc(C(F)(F)F)ccc32)nn1] | MS: 371 [M + H]+ APCI |
| Example 84 | 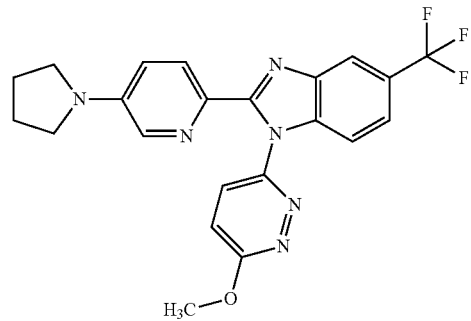 [SMILES: COc1ccc(-n2c(-c3ccc(N4CCCC4)cn3)nc3cc(C(F)(F)F)ccc32)nn1] | MS: 441 [M + H]+ APCI |

TABLE 1-continued
| Example 85 | 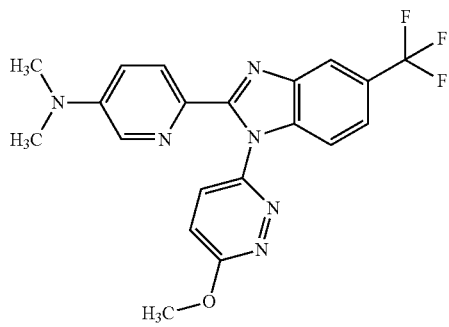 | MS: 415 [M + H]+ APCI |
| Example 86 | 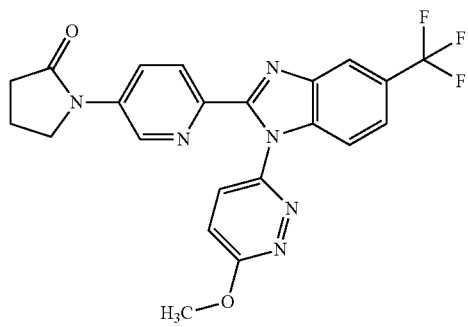 [SMILES: COc1ccc(-n2c(-c3ccc(N4CCCC4=O)cn3)nc3cc(C(F)(F)F)ccc32)nn1] | MS: 455 [M + H]+ APCI |
| Example 87 | 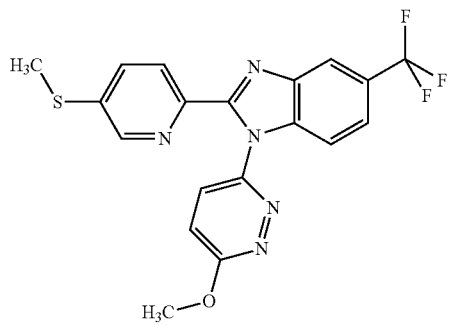 [SMILES: COc1ccc(-n2c(-c3ccc(SC)cn3)nc3cc(C(F)(F)F)ccc32)nn1] | MS: 418 [M + H]+ APCI |
| Example 88 | 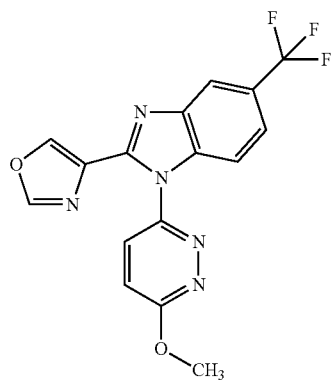 [SMILES: COc1ccc(-n2c(-c3cocn3)nc3cc(C(F)(F)F)ccc32)nn1] | MS: 362 [M + H]+ APCI |

TABLE 1-continued
| | | |
|---|---|---|
| Example 89 | 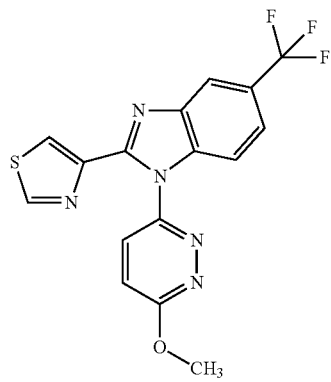 [SMILES: COc1ccc(-n2c(-c3cscn3)nc3cc(C(F)(F)F)ccc32)nn1] | MS: 378 [M + H]+ APCI |
| Example 90 | 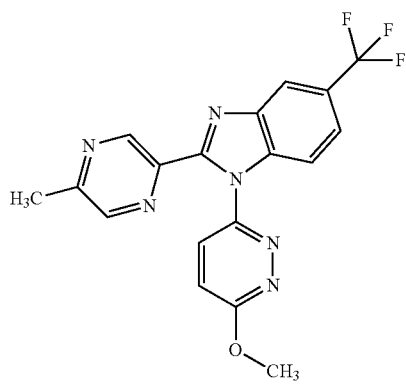 [SMILES: COc1ccc(-n2c(-c3cnc(C)cn3)nc3cc(C(F)(F)F)ccc32)nn1] | MS: 387 [M + H]+ APCI |
| Example 91 | 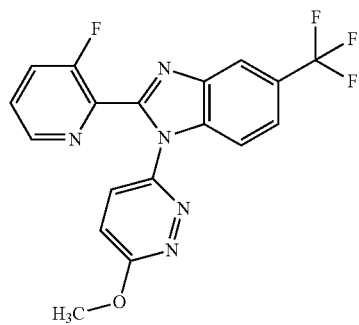 [SMILES: COc1ccc(-n2c(-c3ncccc3F)nc3cc(C(F)(F)F)ccc32)nn1] | MS: 390 [M + H]+ APCI |
| Example 92 | 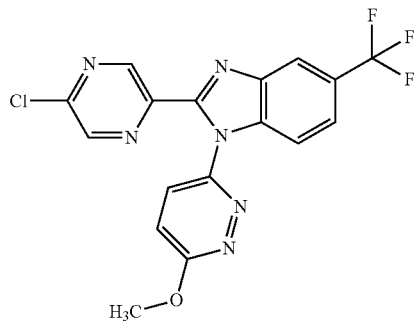 [SMILES: COc1ccc(-n2c(-c3cnc(Cl)cn3)nc3cc(C(F)(F)F)ccc32)nn1] | MS: 407/409 [M + H]+ APCI |

TABLE 1-continued
| Example 93 | 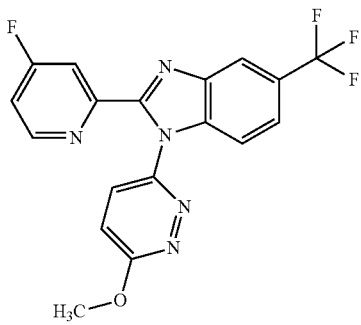 [SMILES: COc1ccc(-n2c(-c3cc(F)ccn3)nc3cc(C(F)(F)F)ccc32)nn1] | MS: 390 [M + H]+ APCI |
| Example 94 | 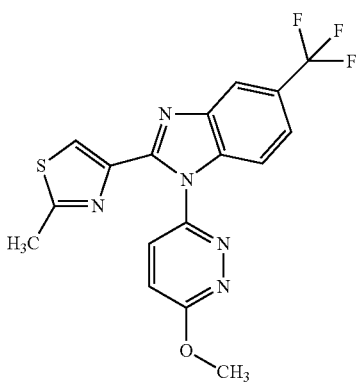 [SMILES: COc1ccc(-n2c(-c3csc(C)n3)nc3cc(C(F)(F)F)ccc32)nn1] | MS: 392 [M + H]+ APCI |
| Example 95 | 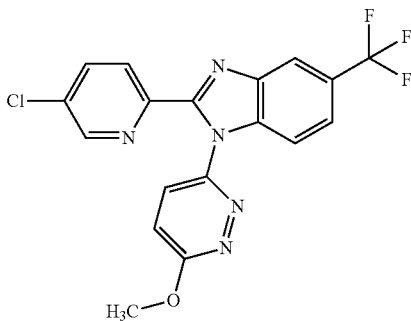 [SMILES: COc1ccc(-n2c(-c3ccc(Cl)cn3)nc3cc(C(F)(F)F)ccc32)nn1] | MS: 406/408 [M + H]+ APCI |
| Example 96 | 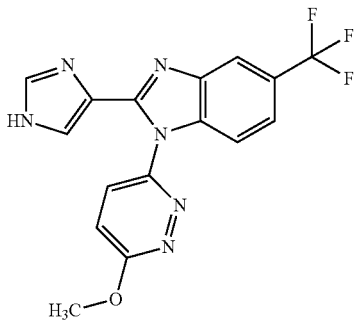 [SMILES: COc1ccc(-n2c(-c3c[nH]cn3)nc3cc(C(F)(F)F)ccc32)nn1] | MS: 361 [M + H]+ APCI |

TABLE 1-continued
| | | |
|---|---|---|
| Example 97 | 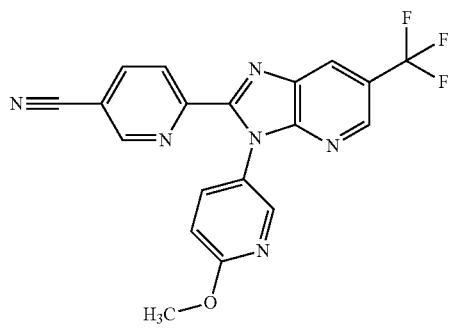 [SMILES: COc1ccc(-n2c(-c3ccc(C#N)cn3)nc3cc(C(F)(F)F)cnc32)cn1] | MS: 397 [M + H]+ APCI |
| Example 98 | 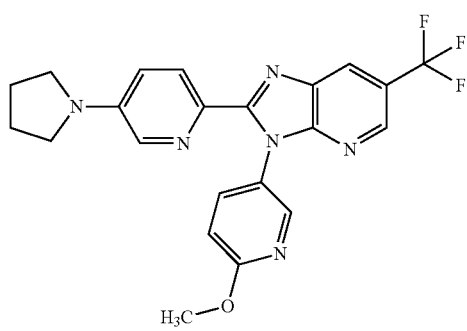 [SMILES: COc1ccc(-n2c(-c3ccc(N4CCCC4)cn3)nc3cc(C(F)(F)F)cnc32)cn1] | MS: 441 [M + H]+ APCI |
| Example 99 | 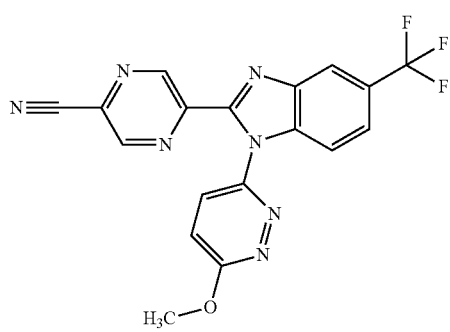 [SMILES: COc1ccc(-n2c(-c3cnc(C#N)cn3)nc3cc(C(F)(F)F)ccc32)nn1] | MS: 398 [M + H]+ APCI |
| Example 100 | 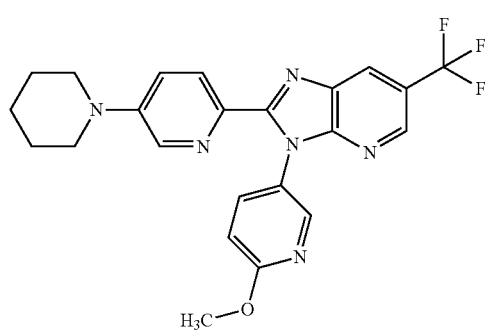 [SMILES: COc1ccc(-n2c(-c3ccc(N4CCCCC4)cn3)nc3cc(C(F)(F)F)cnc32)cn1] | MS: 455 [M + H]+ APCI |
| Example 101 | 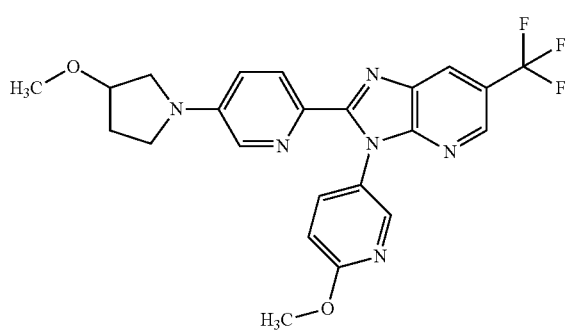 [SMILES: COc1ccc(-n2c(-c3ccc(N4CCC(OC)C4)cn3)nc3cc(C(F)(F)F)cnc32)cn1] | MS: 471 [M + H]+ APCI |

TABLE 1-continued
Example 102　　　　　　　　　　　　　　　　　　　　　　　　　　MS: 457 [M + H]+ APCI
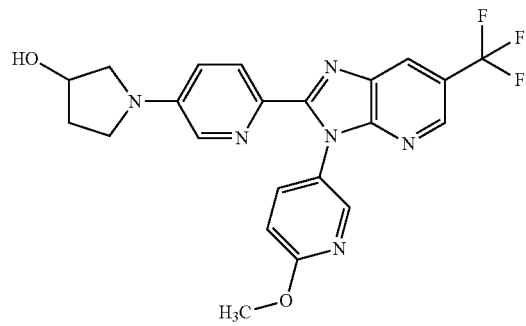 [SMILES: COc1ccc(-n2c(-c3ccc(N4CCC(O)C4)cn3)nc3cc(C(F)(F)F)cnc32)cn1]
Example 103　　　　　　　　　　　　　　　　　　　　　　　　　　MS: 484 [M + H]+ APCI
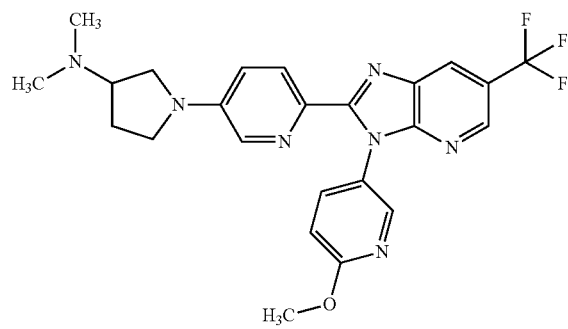 [SMILES: COc1ccc(-n2c(-c3ccc(N4CCC(N(C)C)C4)cn3)nc3cc(C(F)(F)F)cnc32)cn1]
Example 104　　　　　　　　　　　　　　　　　　　　　　　　　　MS: 457 [M + H]+ APCI
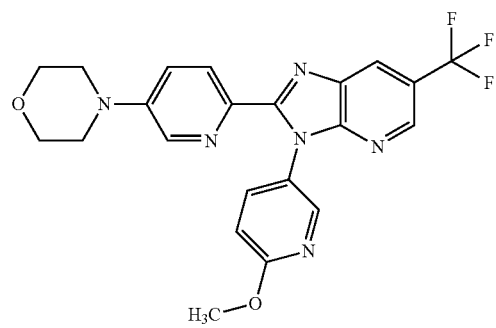 [SMILES: COc1ccc(-n2c(-c3ccc(N4CCOCC4)cn3)nc3cc(C(F)(F)F)cnc32)cn1]
Example 105　　　　　　　　　　　　　　　　　　　　　　　　　　MS: 470 [M + H]+ APCI
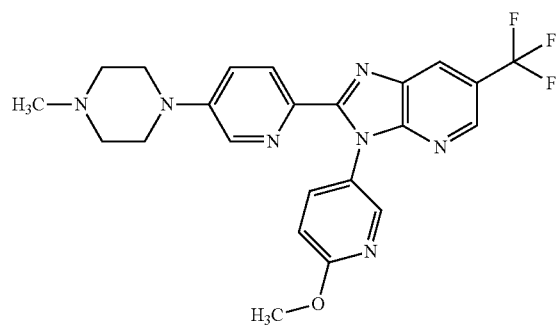 [SMILES: COc1ccc(-n2c(-c3ccc(N4CCN(C)CC4)cn3)nc3cc(C(F)(F)F)cnc32)cn1]

TABLE 1-continued
| Example 106 | 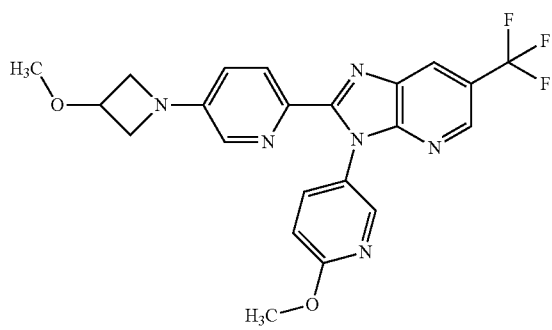 [SMILES: COc1ccc(-n2c(-c3ccc(N4CC(OC)C4)cn3)nc3cc(C(F)(F)F)cnc32)cn1] | MS: 457 [M + H]+ APCI |
| Example 107 | 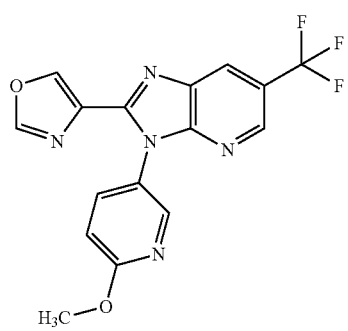 [SMILES: COc1ccc(-n2c(-c3cocn3)nc3cc(C(F)(F)F)cnc32)cn1] | MS: 362 [M + H]+ APCI |
| Example 108 | 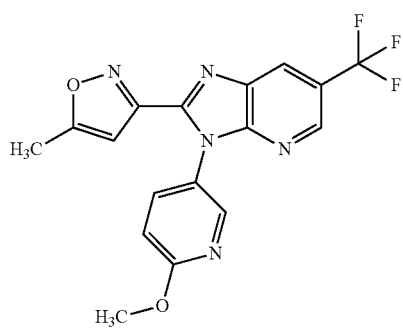 | MS: 376 [M + H]+ APCI |
| Example 109 | 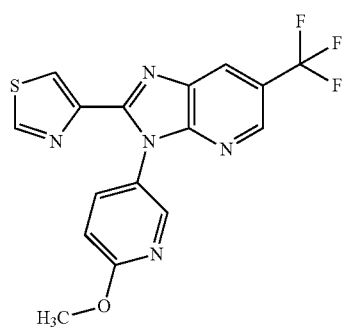 [SMILES: COc1ccc(-n2c(-c3cscn3)nc3cc(C(F)(F)F)cnc32)cn1] | MS: 378 [M + H]+ APCI |
| Example 110 | 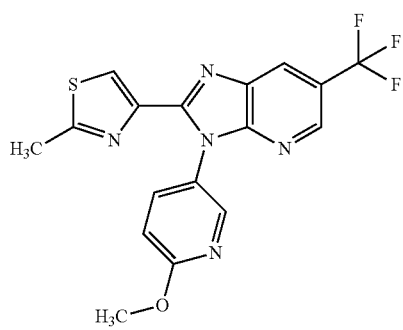 [SMILES: COc1ccc(-n2c(-c3csc(C)n3)nc3cc(C(F)(F)F)cnc32)cn1] | MS: 392 [M + H]+ APCI |

TABLE 1-continued
Example 111 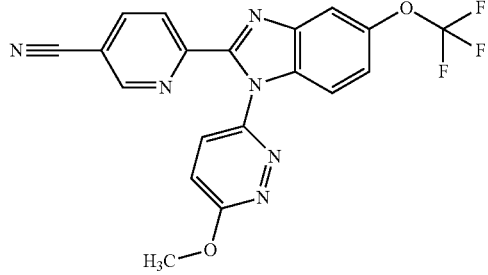 [SMILES: COc1ccc(-n2c(-c3ccc(C#N)cn3)nc3cc(OC(F)(F)F)ccc32)nn1] MS: 413 [M + H]+ APCI
Example 112 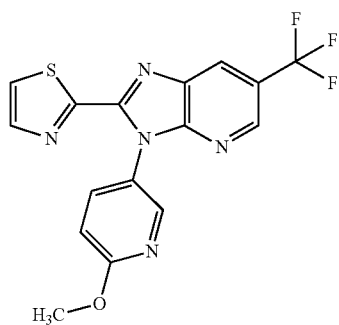 [SMILES: COc1ccc(-n2c(-c3nccs3)nc3cc(C(F)(F)F)cnc32)cn1] MS: 378 [M + H]+ APCI
Example 113 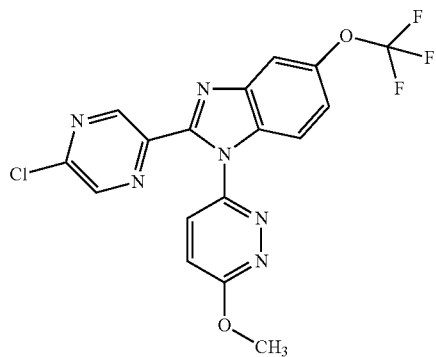 [SMILES: COc1ccc(-n2c(-c3cnc(Cl)cn3)nc3cc(OC(F)(F)F)ccc32)nn1] MS: 423/425 [M + H]+ APCI
Example 114 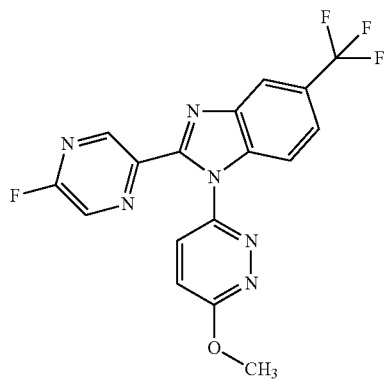 [SMILES: COc1ccc(-n2c(-c3cnc(F)cn3)nc3cc(C(F)(F)F)ccc32)nn1] MS: 391 [M + H]+ APCI TABLE 1-continued
Example 115 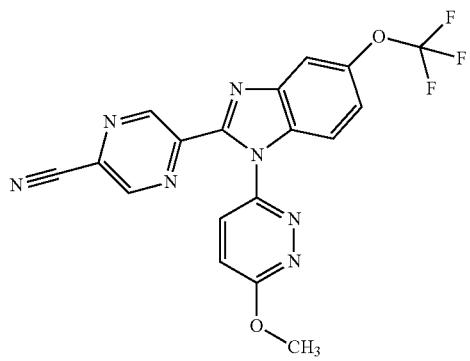 [SMILES: COc1ccc(-n2c(-c3cnc(C#N)cn3)nc3cc(OC(F)(F)F)ccc32)nn1] MS: 414 [M + H]+ APCI
Example 116 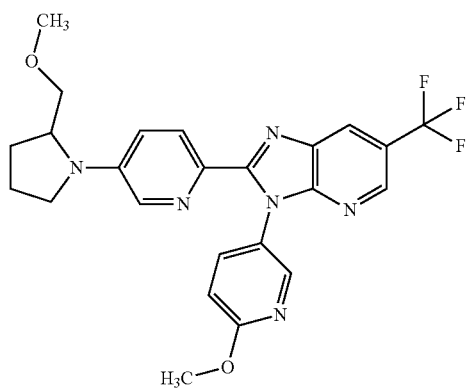 [SMILES: COCC1CCCN1c1ccc(-c2nc3cc(C(F)(F)F)cnc3n2-c2ccc(OC)nc2)nc1] MS: 485 [M + H]+ APCI
Example 117 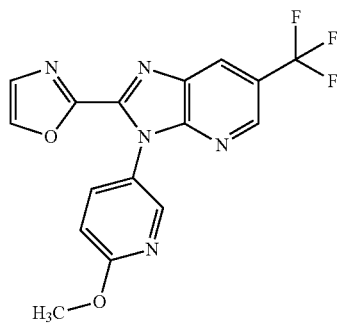 MS: 362 [M + H]+ APCI
Example 118 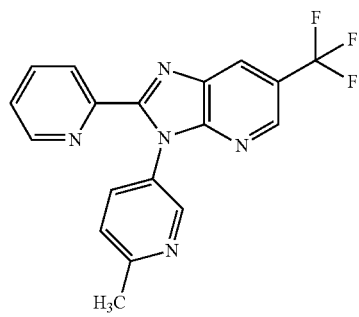 [SMILES: Cc1ccc(-n2c(-c3ccccn3)nc3cc(C(F)(F)F)cnc32)cn1] MS: 356 [M + H]+ APCI TABLE 1-continued
| Example 119 | 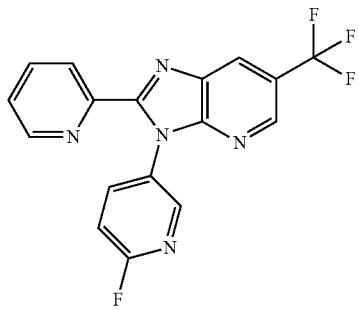 [SMILES: Fc1ccc(-n2c(-c3ccccn3)nc3cc(C(F)(F)F)cnc32)cn1] | MS: 360 [M + H]+ APCI |
| Example 120 | 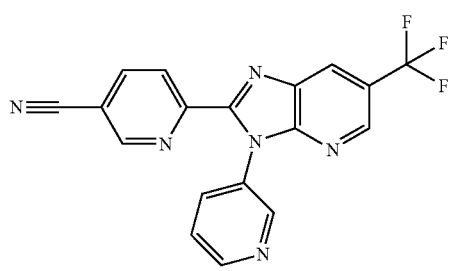 [SMILES: N#Cc1ccc(-c2nc3cc(C(F)(F)F)cnc3n2-c2cccnc2)nc1] | MS: 367 [M + H]+ APCI |
| Example 121 | 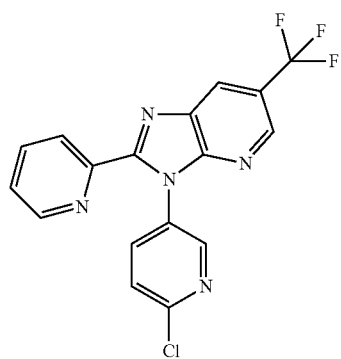 [SMILES: FC(F)(F)c1cnc2c(c1)nc(-c1ccccn1)n2-c1ccc(Cl)nc1] | MS: 376/378 [M + H]+ APCI |
| Example 122 | 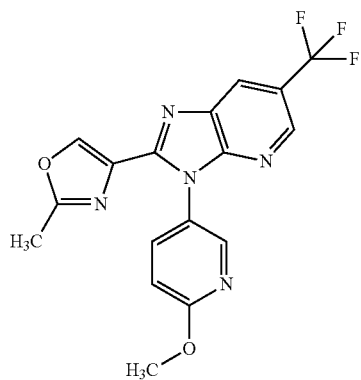 [SMILES: COc1ccc(-n2c(-c3coc(C)n3)nc3cc(C(F)(F)F)cnc32)cn1] | MS: 376 [M + H]+ APCI |

TABLE 1-continued
Example 123 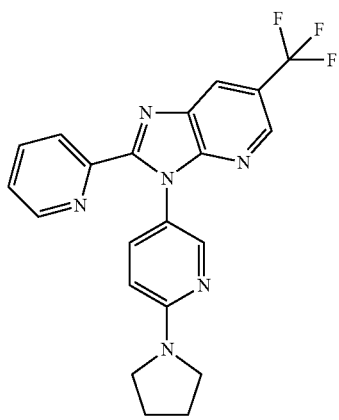 [SMILES: FC(F)(F)c1cnc2c(c1)nc(-c1ccccn1)n2-c1ccc(N2CCCC2)nc1] MS: 411 [M + H]+ APCI
Example 124 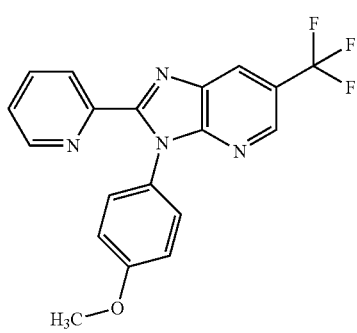 [SMILES: COc1ccc(-n2c(-c3ccccn3)nc3cc(C(F)(F)F)cnc32)cc1] MS: 371 [M + H]+ APCI
Example 125 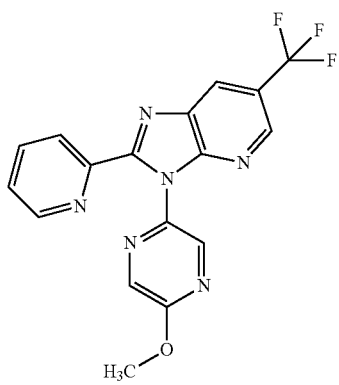 [SMILES: COc1cnc(-n2c(-c3ccccn3)nc3cc(C(F)(F)F)cnc32)cn1] MS: 373 [M + H]+ APCI
Example 126 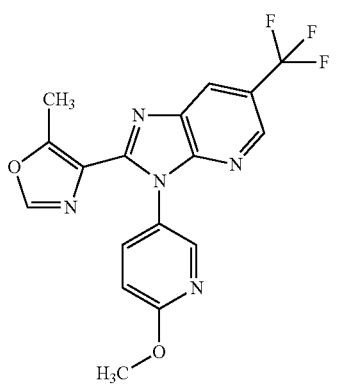 [SMILES: COc1ccc(-n2c(-c3ncoc3C)nc3cc(C(F)(F)F)cnc32)cn1] MS: 376 [M + H]+ APCI

TABLE 1-continued
| Example 127 | MS: 390 [M + H]+ APCI |
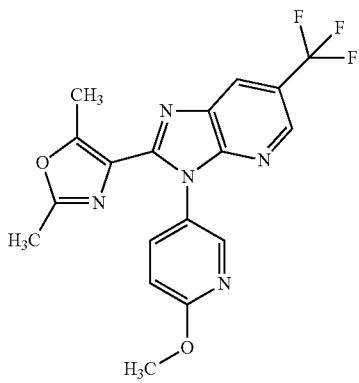 [SMILES: COc1ccc(-n2c(-c3nc(C)oc3C)nc3cc(C(F)(F)F)cnc32)cn1]
| Example 128 | MS: 374 [M + H]+ APCI |
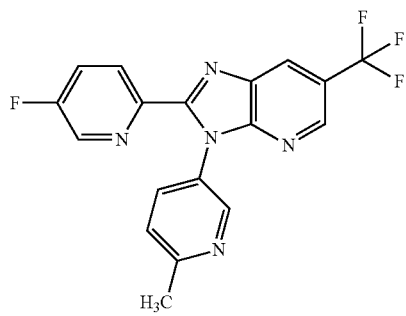 [SMILES: Cc1ccc(-n2c(-c3ccc(F)cn3)nc3cc(C(F)(F)F)cnc32)cn1]
| Example 129 | MS: 346 [M + H]+ APCI |
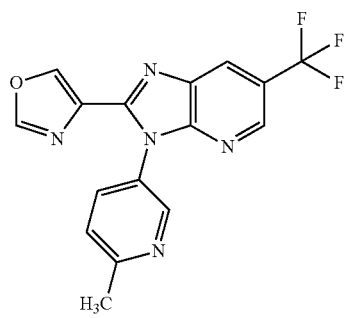 [SMILES: Cc1ccc(-n2c(-c3cocn3)nc3cc(C(F)(F)F)cnc32)cn1]
| Example 130 | MS: 381 [M + H]+ APCI |
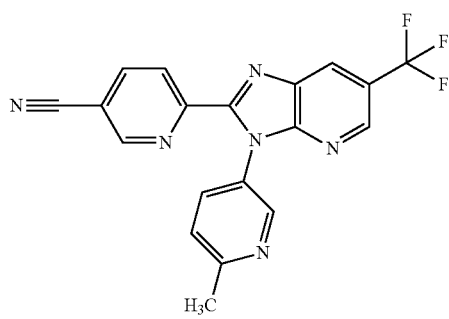 [SMILES: Cc1ccc(-n2c(-c3ccc(C#N)cn3)nc3cc(C(F)(F)F)cnc32)cn1]

TABLE 1-continued
| Example 131 | 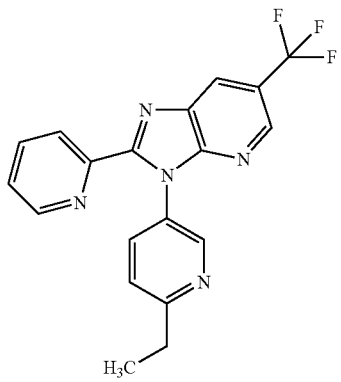 [SMILES: CCc1ccc(-n2c(-c3ccccn3)nc3cc(C(F)(F)F)cnc32)cn1] | MS: 370 [M + H]+ APCI |
| Example 132 | 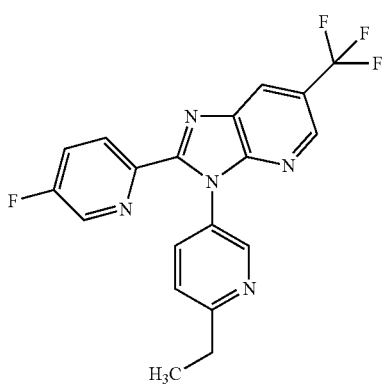 [SMILES: CCc1ccc(-n2c(-c3ccc(F)cn3)nc3cc(C(F)(F)F)cnc32)cn1] | MS: 388 [M + H]+ APCI |
| Example 133 | 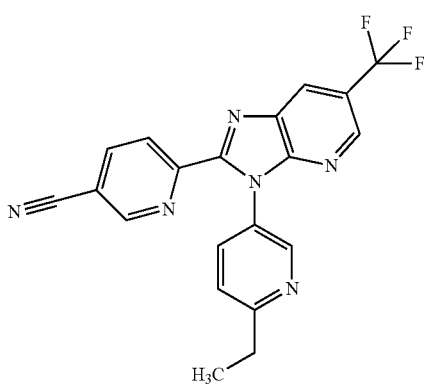 [SMILES: CCc1ccc(-n2c(-c3ccc(C#N)cn3)nc3cc(C(F)(F)F)cnc32)cn1] | MS: 395 [M + H]+ APCI |
| Example 134 | 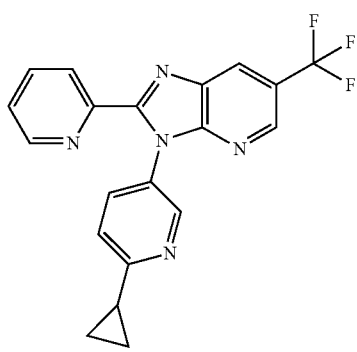 [SMILES: FC(F)(F)c1cnc2c(c1)nc(-c1ccccn1)n2-c1ccc(C2CC2)nc1] | MS: 382 [M + H]+ APCI |

TABLE 1-continued
Example 135
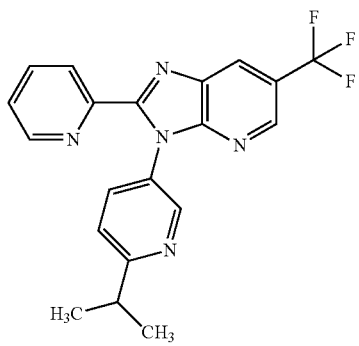 [SMILES: CC(C)c1ccc(-n2c(-c3ccccn3)nc3cc(C(F)(F)F)cnc32)cn1]
MS: 384 [M + H]+ APCI
Example 136
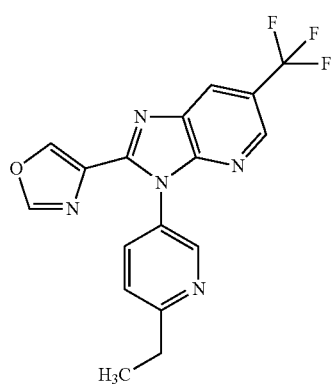 [SMILES: CCc1ccc(-n2c(-c3cocn3)nc3cc(C(F)(F)F)cnc32)cn1]
MS: 360 [M + H]+ APCI
Example 137
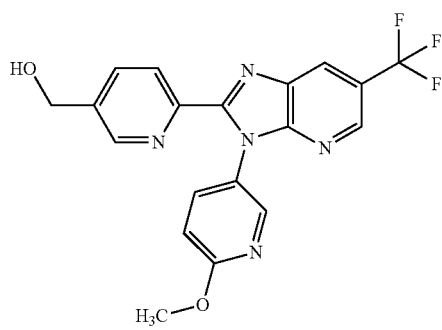 [SMILES: COc1ccc(-n2c(-c3ccc(CO)cn3)nc3cc(C(F)(F)F)cnc32)cn1]
MS: 402 [M + H]+ APCI
Example 138
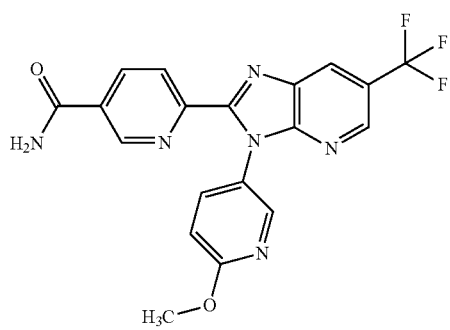 [SMILES: COc1ccc(-n2c(-c3ccc(C(N)=O)cn3)nc3cc(C(F)(F)F)cnc32)cn1]
MS: 415 [M + H]+ APCI TABLE 1-continued
Example 139
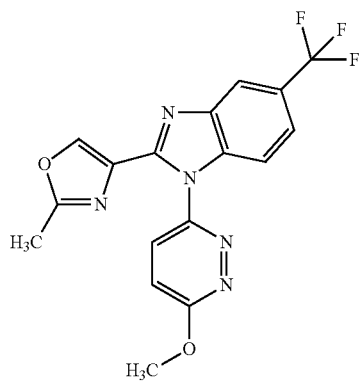 [SMILES: COc1ccc(-n2c(-c3coc(C)n3)nc3cc(C(F)(F)F)ccc32)nn1]
MS: 376 [M + H]+ APCI
Example 140
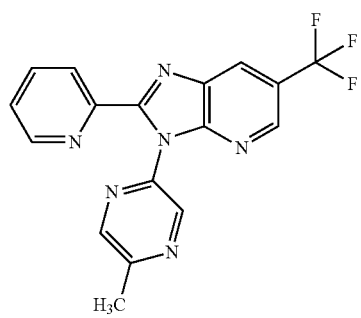
MS: 357 [M + H]+ APCI
Example 141
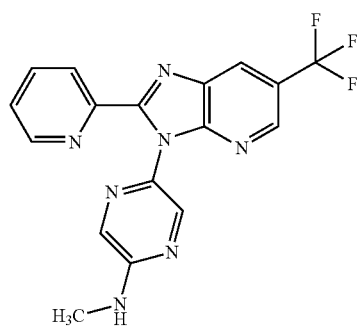 [SMILES: CNc1cnc(-n2c(-c3ccccn3)nc3cc(C(F)(F)F)cnc32)cn1]
MS: 372 [M + H]+ APCI
Example 142
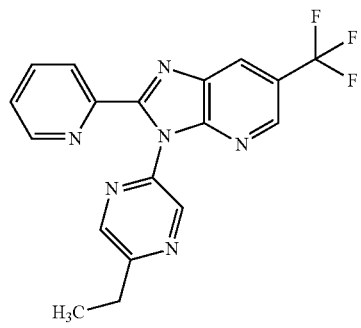 [SMILES: CCc1cnc(-n2c(-c3ccccn3)nc3cc(C(F)(F)F)cnc32)cn1]
MS: 371 [M + H]+ APCI TABLE 1-continued Example 143

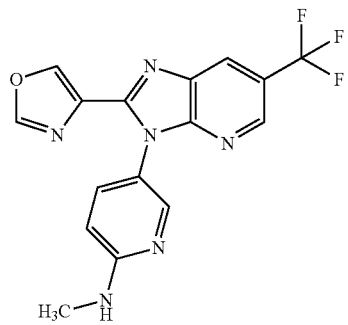

MS: 361 [M + H]+ APCI

Example 144

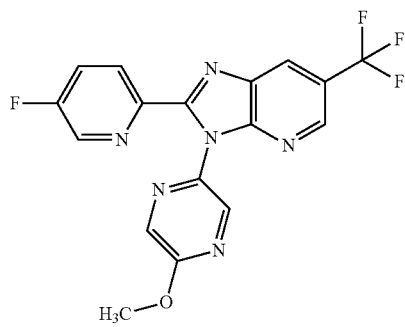 [SMILES: COc1cnc(-n2c(-c3ccc(F)cn3)nc3cc(C(F)(F)F)cnc32)cn1]

MS: 391 [M + H]+ APCI

Example 145

6-isopropoxy-3-(6-methoxypyridin-3-yl)-2-pyridin-2-yl-3H-imidazo[4,5-b]pyridine

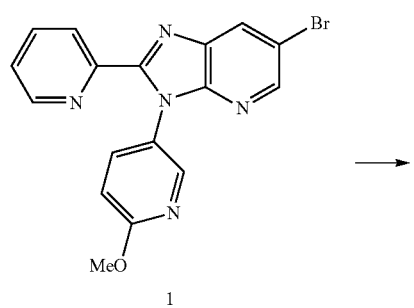

-continued

To the compound 1 (1.0 g) were added tris(dibenzylidene acetone)dipalladium (0) (0.239 g), 2-di-tert-butylphosphino-3,4,5,6-tetramethyl-2',4',6'-triisopropyl-1,1'-biphenyl (0.251 g), an aqueous solution of 0.8N-potassium hydroxide (13 ml) and dioxane (52 ml), and the mixture solution was heated to 100° C. After the mixed solution was stirred for 3 h, it was kept standing to cool to room temperature, and an insoluble material was filtrated with Celite. To the filtrate was added water, and the aqueous solution was extracted with ethyl acetate. After the organic layer was washed with a saturated saline, the organic layer was dried with anhydrous sodium sulfate. After the organic layer was filtrated and concentrated, the concentrated residue was purified by the silica gel column chromatography, and the compound 2 (0.424 g) was obtained.

MS m/z 320[M+H]+, APCI(+)

After the compound 2 (40 mg) was dissolved in DMF (2 ml), sodium hydride (10 mg) was added thereto at 0° C., and the mixture solution was stirred for 30 min. 2-Bromopropane (0.023 ml) was added thereto at 0° C., and the reaction temperature was raised to room temperature. After the reaction mixture was stirred for 3 days, water was added thereto, and Example 146

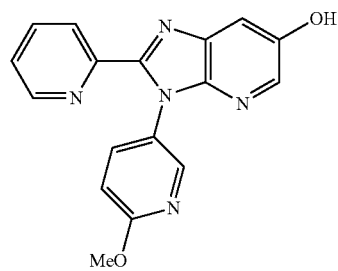

1

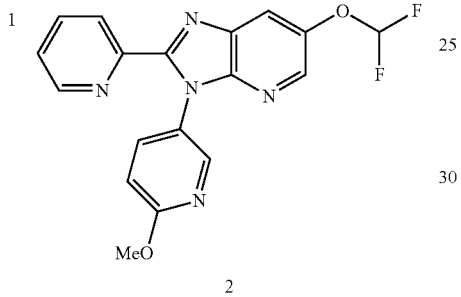

2

The compound 1 (50.0 mg) was dissolved in DMF (2 ml) and H$_2$O (0.2 ml), and sodium chlorodifluoroacetate (47.7 mg) and potassium carbonate (26.0 mg) were added thereto, and the mixture was heated to 100° C. After the mixture was stirred for 5 h, sodium chlorodifluoroacetate (95.4 mg) and potassium carbonate (26.0 mg) were added thereto, and the mixture was stirred at 100° C. for 5 h. After the mixture was kept standing to cool to room temperature, water and ethyl acetate were added thereto. After the organic layer was separated, it was washed with a saturated saline and dried with anhydrous sodium sulfate. After the organic layer was filtrated and concentrated, the residue was purified by the silica gel column chromatography, and the compound 2 (14.1 mg) was obtained.

MS m/z 370 [M+H]+, APCI(+)

Example 147

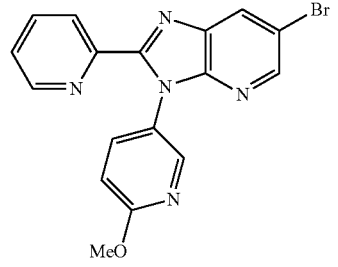

1

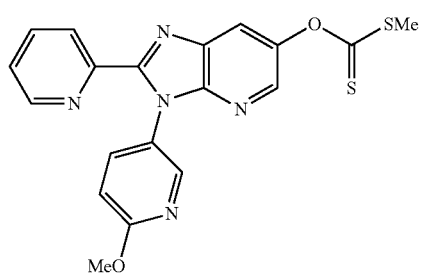

2

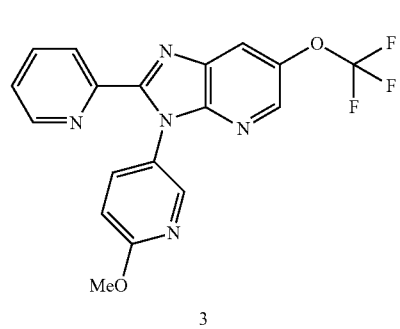

3

To a DMF (1 ml) solution of the compound 1 (55 mg), sodium hydride (60% oil suspension: 14 mg) was added at 0° C., and the mixture was stirred at room temperature for 1 h. To the mixture was added carbon disulfide (104 µl) at 0° C., and the solution was stirred at room temperature for 8 h. To the solution at 0° C. was added methyl iodide (43 µl). After the reaction solution was stirred for 2 days, an aqueous solution of saturated ammonium chloride was added to stop the reaction, and was extracted with ethyl acetate. The organic layer was washed sequentially with water and with a saturated saline. After the organic layer was dried with anhydrous sodium sulfate, the organic layer was filtrated. After the filtrate was concentrated, the residue was purified by the silica gel column chromatography, and the compound 2 (55 mg) was obtained.

MS m/z 410 [M+H]+, APCI(+)

To a methylene dichloride (0.5 ml) solution of 1,3-dibromo-5,5-dimethylhydantoin (148 mg) was added hydrogen fluoride-pyridine complex (a 65% solution: 386 µl) at −78° C., and the mixture was stirred vigorously. After 5 min, a methylene dichloride (0.5 ml) solution of the compound 2 (55 mg) was added thereto, and the mixture was stirred at 0° C. for 2 h. After the mixture was diluted with chloroform, an aqueous solution saturated with sodium bicarbonate was added thereto for stopping the reaction. After the organic layer was dried with anhydrous sodium sulfate, the organic layer was filtrated. After the filtrate was concentrated, the residue was purified by the silica gel column chromatography, and the compound 3 (16 mg) was obtained.

MS m/z 388 [M+H]+, APCI(+)

TABLE 2
| | |
|---|---|
| Example 148 | MS: 379 [M + H]+ APCI |
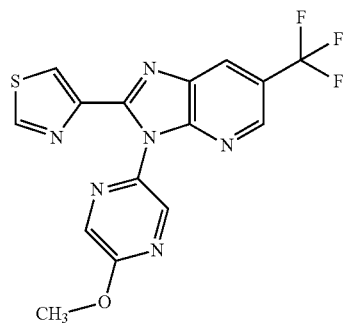 [SMILES: COc1cnc(-n2c(-c3cscn3)nc3cc(C(F)(F)F)cnc32)cn1]
| | |
|---|---|
| Example 149 | MS: 389 [M + H]+ ESI |
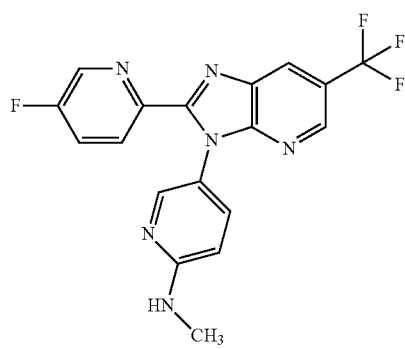 [SMILES: CNc1ccc(-n2c(-c3ccc(F)cn3)nc3cc(C(F)(F)F)cnc32)cn1]
| | |
|---|---|
| Example 150 | MS: 396 [M + H]+ ESI |
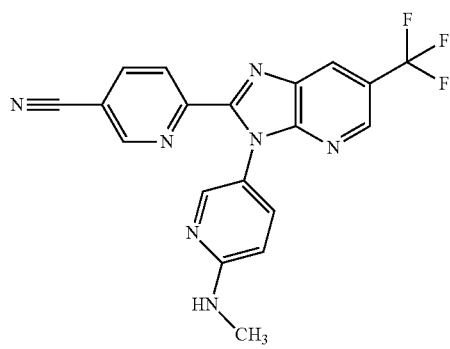 [SMILES: CNc1ccc(-n2c(-c3ccc(C#N)cn3)nc3cc(C(F)(F)F)cnc32)cn1]
| | |
|---|---|
| Example 151 | MS: 363 [M + H]+ ESI |
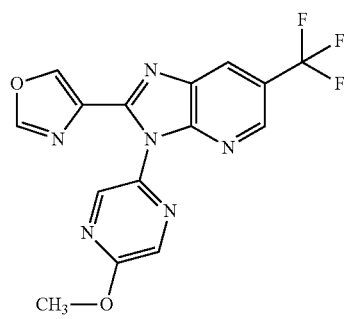 [SMILES: COc1cnc(-n2c(-c3cocn3)nc3cc(C(F)(F)F)cnc32)cn1]

TABLE 2-continued

| | | |
|---|---|---|
| Example 152 | [structure] | MS: 377 [M + H]+ ESI |
| Example 153 | [structure] | MS: 376 [M + H]+ ESI |
| Example 154 | [structure] | MS: 377 [M + H]+ ESI |
| Example 155 | [structure] | MS: 378 [M + H]+ ESI |
| Example 156 | [structure] | MS: 391 [M + H]+ ESI |

TABLE 2-continued
Example 157 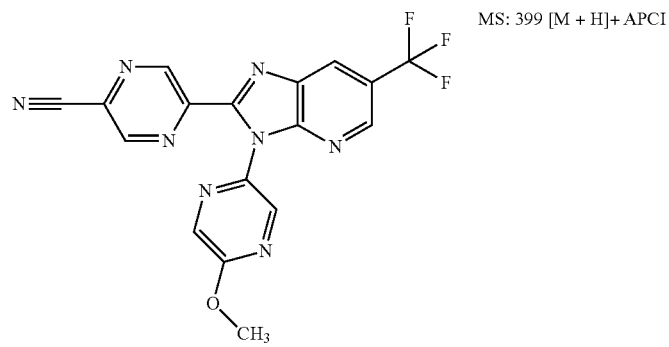 MS: 399 [M + H]+ APCI
Example 158 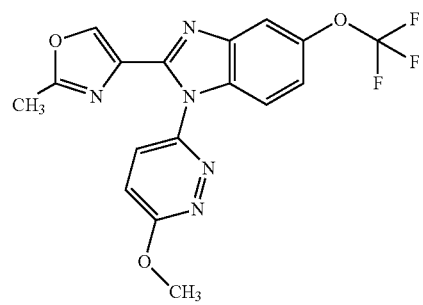 [SMILES: COc1ccc(-n2c(-c3coc(C)n3)nc3cc(OC(F)(F)F)ccc32)nn1] MS: 392 [M + H]+ APCI
Example 159 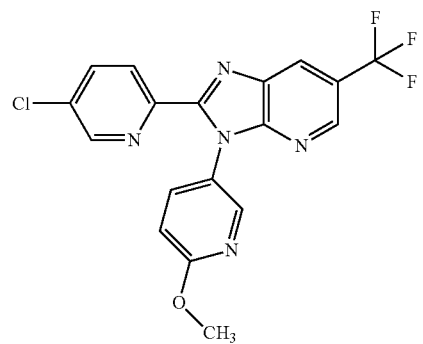 [SMILES: COc1ccc(-n2c(-c3ccc(Cl)cn3)nc3cc(C(F)(F)F)cnc32)cn1] MS: 406/408 [M + H]+ APCI
Example 160 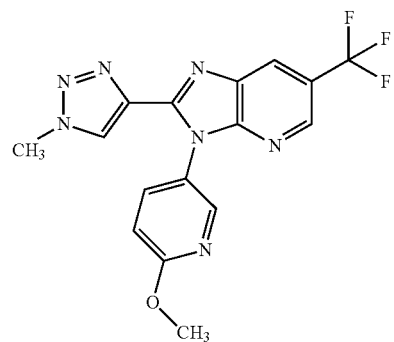 [SMILES: COc1ccc(-n2c(-c3cn(C)nn3)nc3cc(C(F)(F)F)cnc32)cn1] MS: 376 [M + H]+ APCI TABLE 2-continued
Example 161 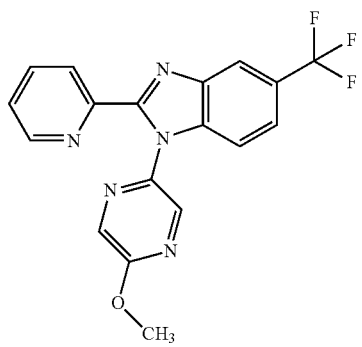 [SMILES: COc1cnc(-n2c(-c3ccccn3)nc3cc(C(F)(F)F)ccc32)cn1] MS: 372 [M + H]+ APCI
Example 162 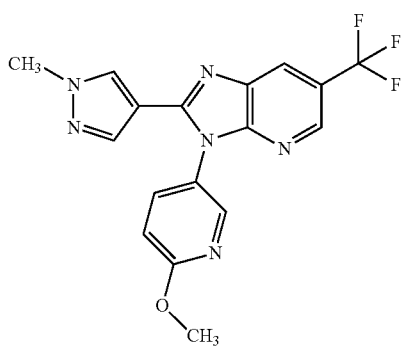 [SMILES: COc1ccc(-n2c(-c3cnn(C)c3)nc3cc(C(F)(F)F)cnc32)cn1] MS: 375 [M + H]+ APCI
Example 163 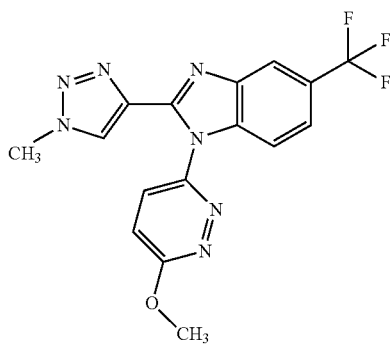 [SMILES: COc1ccc(-n2c(-c3cn(C)nn3)nc3cc(C(F)(F)F)ccc32)nn1] MS: 376 [M + H]+ APCI
Example 164 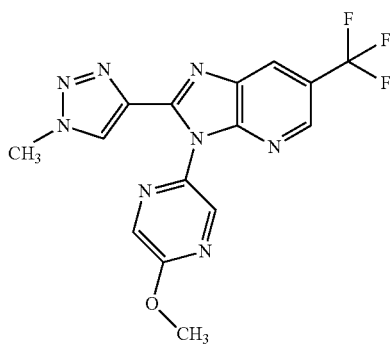 [SMILES: COc1cnc(-n2c(-c3cn(C)nn3)nc3cc(C(F)(F)F)cnc32)cn1] MS: 377 [M + H]+ APCI TABLE 2-continued
| Example 165 | 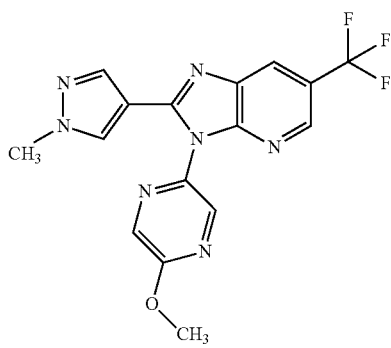 [SMILES: COc1cnc(-n2c(-c3cnn(C)c3)nc3cc(C(F)(F)F)cnc32)cn1] | MS: 376 [M + H]+ APCI |
| Example 166 | 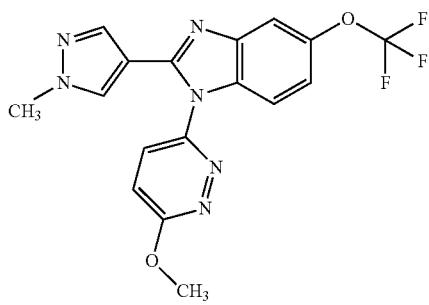 [SMILES: COc1ccc(-n2c(-c3cnn(C)c3)nc3cc(OC(F)(F)F)ccc32)nn1] | MS: 391 [M + H]+ APCI |
| Example 167 | 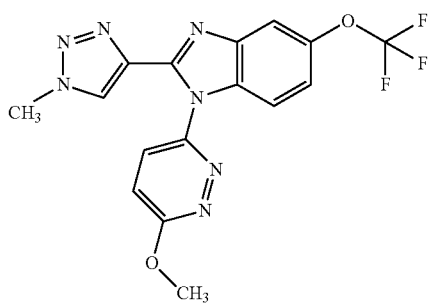 [SMILES: COc1ccc(-n2c(-c3cn(C)nn3)nc3cc(OC(F)(F)F)ccc32)nn1] | MS: 392 [M + H]+ APCI |
| Example 168 | 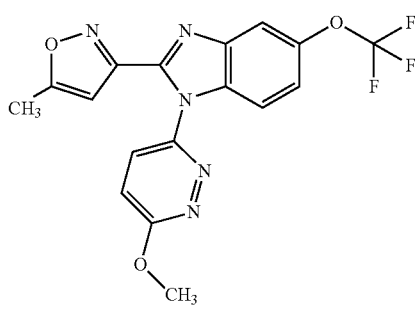 | MS: 392 [M + H]+ APCI |
| Example 169 | 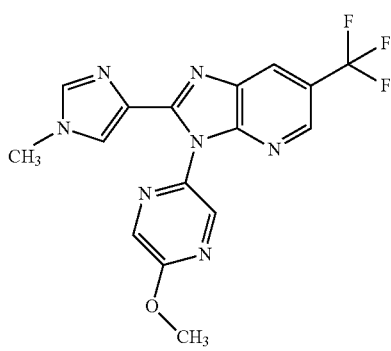 [SMILES: COc1cnc(-n2c(-c3cn(C)cn3)nc3cc(C(F)(F)F)cnc32)cn1] | MS: 376 [M + H]+ APCI |

TABLE 2-continued
| Example 170 | 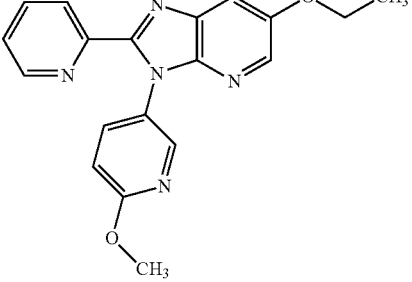 | MS: 348 [M + H]+ APCI |
| Example 171 | 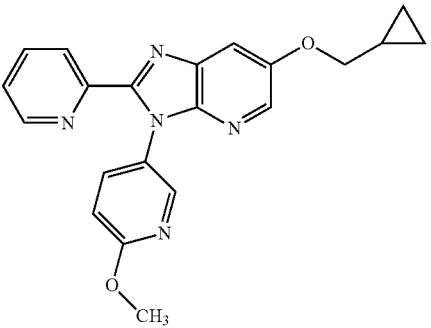 [SMILES: COc1ccc(-n2c(-c3ccccn3)nc3cc(OCC4CC4)cnc32)cn1] | MS: 374 [M + H]+ APCI |
| Example 172 | 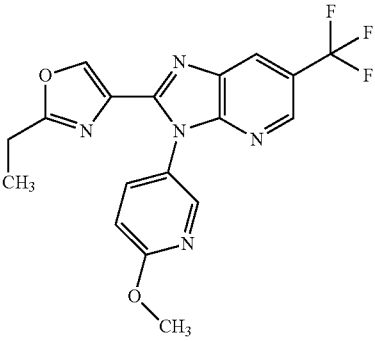 [SMILES: CCc1nc(-c2nc3cc(C(F)(F)F)cnc3n2-c2ccc(OC)nc2)co1] | MS: 390 [M + H]+ APCI |
| Example 173 | 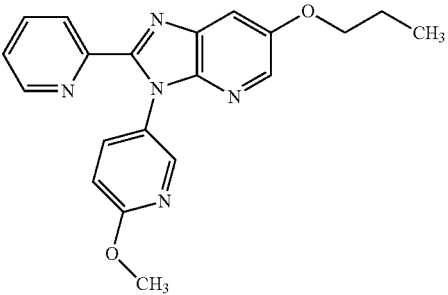 [SMILES: CCCOc1cnc2c(c1)nc(-c1ccccn1)n2-c1ccc(OC)nc1] | MS: 362 [M + H]+ APCI |
| Example 174 | 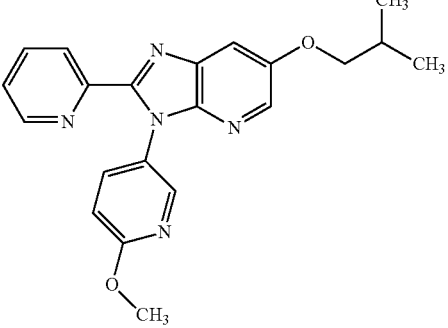 | MS: 376 [M + H]+ APCI |

TABLE 2-continued
Example 175  MS: 402 [M + H]+ APCI
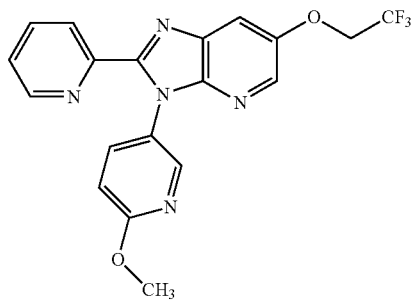 [SMILES: COc1ccc(-n2c(-c3ccccn3)nc3cc(OCC(F)(F)F)cnc32)cn1]
Example 176  MS: 416 [M + H]+ APCI
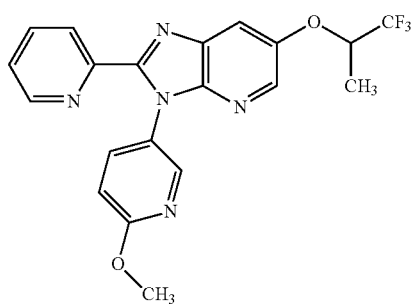 [SMILES: COc1ccc(-n2c(-c3ccccn3)nc3cc(OC(C)C(F)(F)F)cnc32)cn1]
Example 177  MS: 406 [M + H]+ APCI
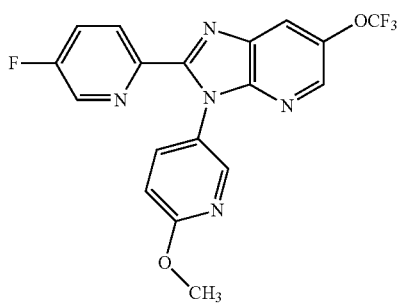 [SMILES: COc1ccc(-n2c(-c3ccc(F)cn3)nc3cc(OC(F)(F)F)cnc32)cn1]
Example 178  MS: 388 [M + H]+ APCI
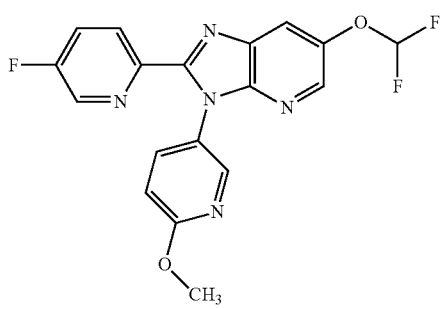 [SMILES: COc1ccc(-n2c(-c3ccc(F)cn3)nc3cc(OC(F)F)cnc32)cn1]

Example 179

3-(6-methoxypyridin-3-yl)-2-pyridin-2-yl-7-(trifluoromethyl)imidazo[1,2-b]pyridazine

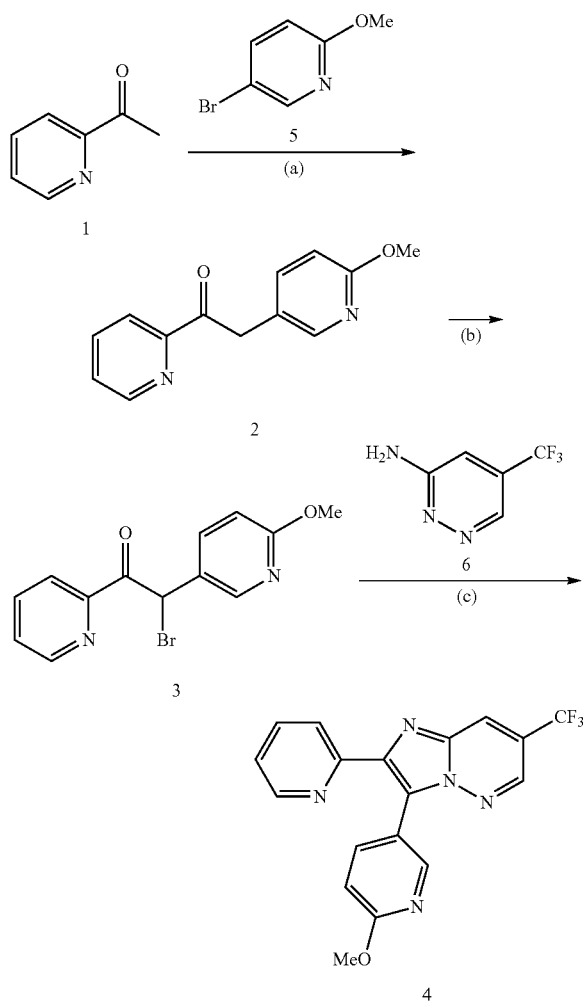

Under an argon atmosphere, a 1,4-dioxane solution (40 ml) of 2-acetylpyridine (6.44 g) was added by drops into a THF solution (1M, 106.4 ml) of lithiumhexamethyldisilazide at 0° C. for 30 min. Tridibenzylidene acetone dipalladium (1.22 g) and a 1,4-dioxane (30 ml) solution of tri-t-butylphosphine (0.50 ml) were added thereto, and at room temperature, a 1,4-dioxane (30 ml) solution of 5-bromo-2-methoxypyridine (5 g) was added thereto and the reaction mixture was stirred at 90° C. for 3 h. After the mixture was filtrated with Celite, the residue was purified by the silica gel column chromatography, and the compound 2 (3.66 g) was obtained.

MS m/z 229 [M+H]+, APCI(+)

To an acetic acid (30 ml) solution of the compound 2 (1 g) was added bromine (0.34 ml), and the reaction solution was stirred at 50° C. for 3 h. After the reaction solution was concentrated, the residue was washed with an aqueous solution saturated with sodium bicarbonate and extracted with ethyl acetate. After the organic layer was washed with a saturated saline, the organic layer was dried with anhydrous sodium sulfate. After the organic layer was filtrated and concentrated, the residue was purified by the silica gel column chromatography affording the compound 3 (0.14 g).

MS m/z 307/309 [M+H]+, APCI(+)

The compound 3 (26 mg) and the compound 6 (14 mg) were dissolved in DMF (1 ml) followed by the addition of sodium bicarbonate (7 mg) thereto, and the mixed solution was stirred at 80° C. for 20 h. After the solution was diluted with ethyl acetate, the solution was washed sequentially with water and a saturated saline. After the organic layer was dried with anhydrous sodium sulfate, the organic layer was filtrated. After the organic layer was concentrated, the residue was purified by the silica gel column chromatography affording the compound 4 (2.6 mg).

MS m/z 372 [M+H]+, APCI(+)

Example 180

3-(6-methoxypyridin-3-yl)-2-pyridin-2-yl-6-(trifluoromethyl)pyrazolo[1,5-a]pyrimidine

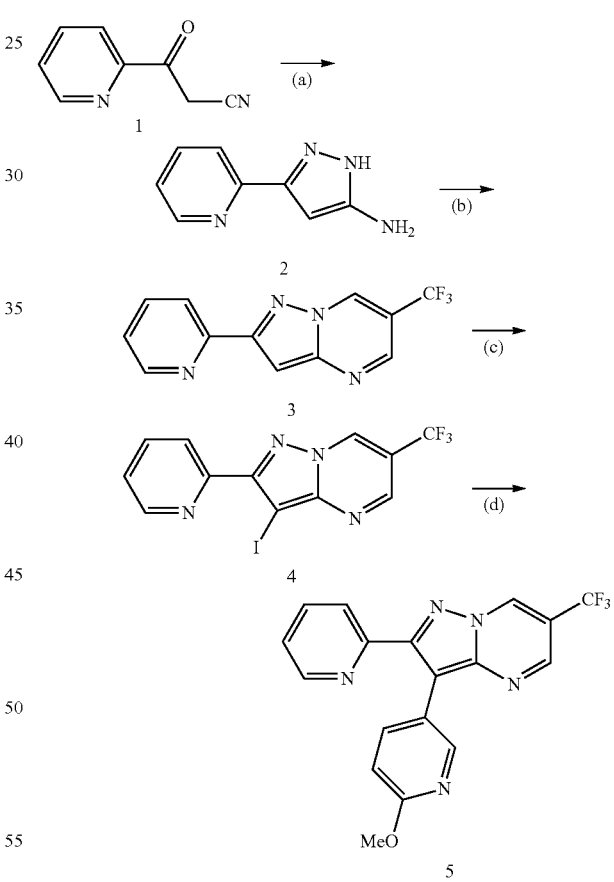

To an ethanol (75 ml) solution of 3-oxo-3-(2-pyridinyl)propanenitrile (5 g) were added a hydrazine monohydrate (2.49 ml) solution and acetic acid (2.50 ml) at room temperature, and the mixture solution was refluxed under heating for 20 h. After the mixture was concentrated, the residue was diluted with ethyl acetate, and washed sequentially with water and with a saturated saline. After the organic layer was dried with anhydrous sodium sulfate, the organic layer was filtrated. After the filtrate was concentrated, the residue was purified by the silica gel column chromatography affording the compound 2 (2.51 g).

MS m/z 161 [M+H]+, APCI(+)

DMF was heated to 50° C., and 3,3,3-trifluoropropionic acid (1.5 ml) was added thereto and the solution was stirred. The mixture was heated to 70° C., and phosphorus oxychloride (2.60 ml) was added thereto by drops for 1 h. After the mixture was stirred for 3 h, the reaction solution was concentrated i vacuo. The residue was dissolved in acetonitrile (6 ml), and at 0° C., the compound 2 (300 mg) and sodium methoxide (546 mg) were added slowly. After the reaction solution was stirred at room temperature for 2 h, an insoluble material was filtrated and diluted by ethyl acetate. The organic layer was washed sequentially with water and with a saturated saline. The organic layer was dried with anhydrous sodium sulfate and filtrated The filtrate was concentrated, and the residue was purified by the silica gel column chromatography affording the compound 3 (125 mg) was obtained.

MS m/z 265 [M+H]+, APCI(+)

The compound 3 (122.5 mg) was dissolved in acetonitrile, and N-iodosuccinimide (522 mg) was added in small portions, followed by stirring at 50° C. for 3 h. After the reaction solution was diluted by ethyl acetate, the solution was washed sequentially with water and with a saturated saline. The organic layer was dried with anhydrous sodium sulfate and then filtrated. The filtrate was concentrated, and the residue was purified by the silica gel column chromatography affording the compound 4 (131.6 mg).

MS m/z 391 [M+H]+, APCI(+)

Under an argon atmosphere, the compound 4 (130.5 mg) was dissolved in 1,2-dimethoxyethane (2.6 ml), and to the solution were added 2-methoxy-5-pyridine boronic acid (73.4 mg), a palladium chloride 1,1'-ferrocene bisdiphenylphosphino ferrocene complex (23.4 mg) and potassium carbonate (88.4 mg), and the reaction mixture was stirred at 90° C. for 20 h.

After an insoluble material was filtrated by Celite, the filtrate was concentrated. The residue was purified by the silica gel column chromatography affording the compound 5 (34.4 mg).

MS m/z 372 [M+H]+, APCI(+)

Example 181

2-(5-fluoropyridin-2-yl)-3-(6-methoxypyridin-3-yl)-7-(trifluoromethyl)imidazo[1,2-b]pyridazine

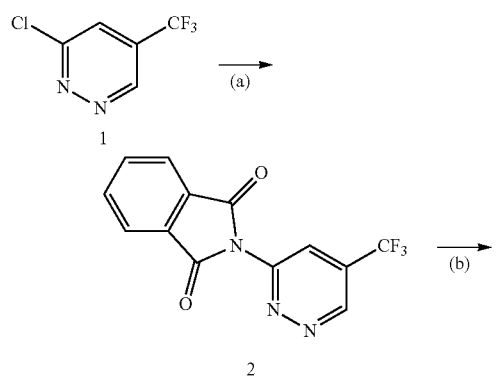

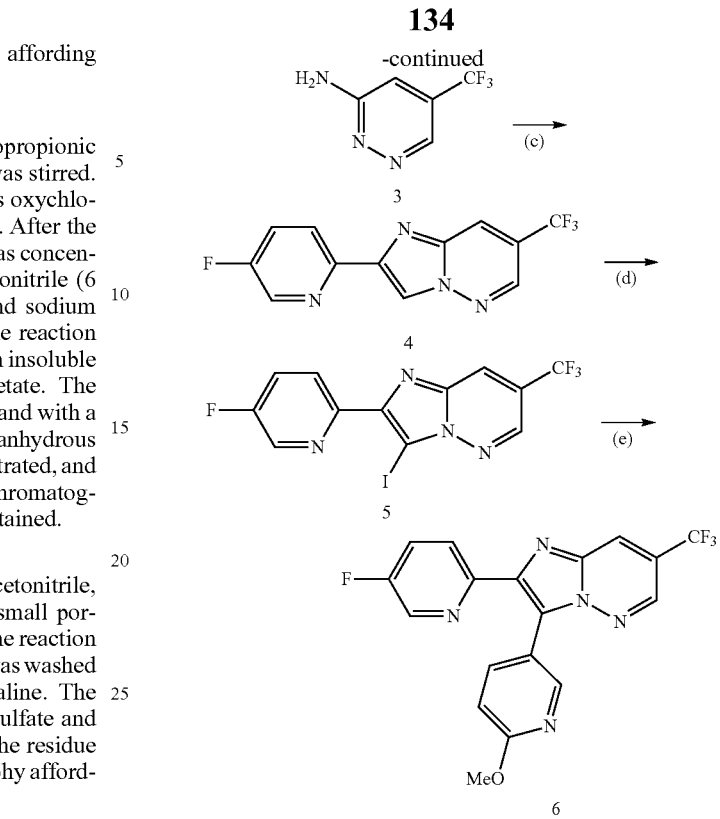

To a DMF (14 ml) solution of the compound 1 (2 g) was added a potassium salt of phthalimide (3.04 g), and the reaction solution was heated to 130° C. by irradiation of microwave, followed by stirring for 1.5 h. The reaction solution was diluted by ethyl acetate and washed with sequentially with water and with a saturated saline. The organic layer was dried with anhydrous sodium sulfate and filtrated. The filtrate was concentrated, and the residue was purified by the silica gel column chromatography affording the compound 2 (2.06 g). To a 1,2-dimethoxyethane (41 ml) solution of the compound 2 (2.06 g) was added a 80% hydrazine monohydrate (17 ml), and the mixture was stirred at 60° C. for 3 h. To the mixture was added water, and the mixture was extracted by ethyl acetate. The organic layer was dried with anhydrous sodium sulfate and filtrated. The filtrate was concentrated, and the residue was purified by the silica gel column chromatography affording the compound 3 (0.71 g).

MS m/z 164 [M+H]+, APCI(+)

The compound 3 (270 mg) and 2-bromo-1-(5-fluoro-pyridin-2-yl)-ethanone hydrobromate (990 mg) was dissolved in a mixed solvent of toluene (5 ml) and ethanol (1 ml), and sodium bicarbonate (1.39 g) was added thereto, and the mixed solution was refluxed for 20 h under heating. After the reaction solution was concentrated, the residue was diluted by ethyl acetate and washed sequentially with water and with a saturated saline. After the organic layer was dried with anhydrous sodium sulfate, the organic layer was filtrated. The filtrate was concentrated, and the residue was purified by the silica gel column chromatography affording the compound 4 (95.1 mg).

MS m/z 283 [M+H]+, APCI(+)

To an acetonitrile (2 ml) solution of the compound 4 (92.2 mg), N-iodosuccinimide (221 mg) was added, and the solution was stirred at room temperature for 20 h. Acetonitrile (2 ml), N-iodosuccinimide (221 mg) and acetic acid (1 drop) were added thereto, and the mixture was stirred at 50° C. for 4 h. The reaction mixture was diluted by ethyl acetate, and washed sequentially with water and with a saturated saline. The organic layer was dried with anhydrous sodium sulfate, and filtrated. The filtrate was concentrated, and the residue was purified by the silica gel column chromatography affording the compound 5 (122 mg).

MS m/z 409 [M+H]+, APCI(+)

Under an argon atmosphere, to a 1,2-dimethoxyethane (2.4 ml) solution of the compound 5 (119.3 mg) were added 2-methoxy-5-pyridineboronic acid (67.1 mg), tetrakis-triphenylphosphine palladium (33 8 mg), and an aqueous solution of sodium hydroxide (5 mol/l, 117 µl), and the mixture solution was stirred at 90° C. for 3 h. After the reaction solution was filtrated by Celite, the solution was concentrated in vacuo. The residue was purified by the silica gel column chromatography affording the compound 6 (89.1 mg).

MS m/z 390 [M+H]+, APCI(+)

Example 182

1-(6-methoxypyridin-3-yl)-2-pyridin-2-yl-5-(trifluoromethyl)-1H-indole

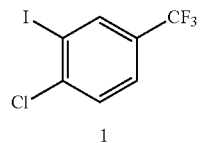

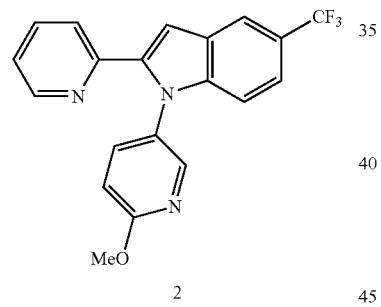

4-Chloro-3-iodobenzenetrifluoride (306 mg) was dissolved in toluene (3 ml), and thereto were added 2-ethynylpyridine (155 mg), copper iodide (19.0 mg), 1,3-bis-(2,6-diisopropylphenyl)-imidazolium chloride (42.5 mg), acetic acid palladium (II) (22.5 mg) and cesium carbonate (489 mg), and the mixture was heated to 100° C. After the mixture was stirred for 3 h, the mixture was kept standing to cool to room temperature, and thereto were added 3-amino-6-methoxypyridine (149 mg) and potassium-t-butoxide (168 mg), and the reaction mixture was heated to 100° C. After the reaction mixture was stirred all day and all night, it was kept standing to cool to room temperature, and to the reaction solution were added ethyl acetate and water. After an insoluble material was filtrated, the organic layer was separated. The organic layer was washed with a saturated saline and dried with anhydrous sodium sulfate. After the organic layer was filtrated and concentrated, the residue was purified by the silica gel column chromatography affording the compound 2 (77.0 mg).

MS m/z 370 [M+H]+, APCI(+)

Example 183

1-(6-methoxypyridin-3-yl)-2-pyridin-2-yl-5-(trifluoromethyl)-1H-pyrrolo[2,3-b]pyridine

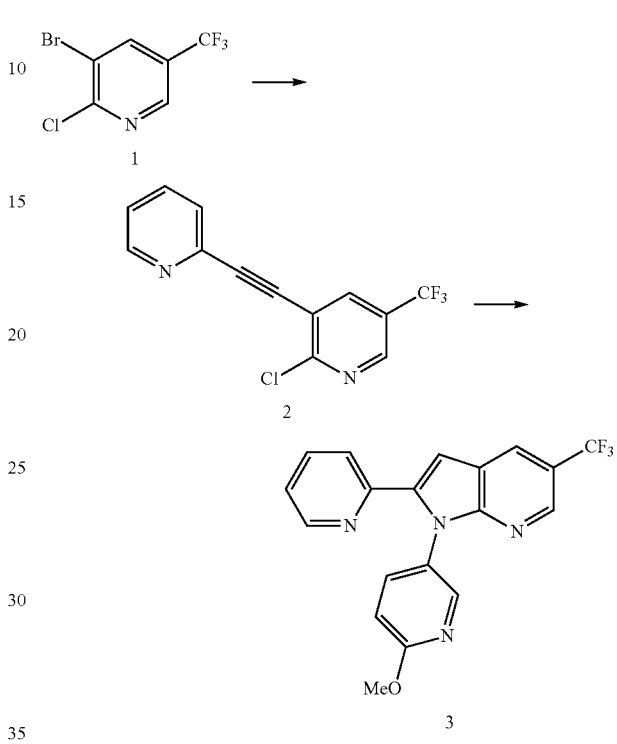

A mixture of 3-bromo-2-chloro-5-(trifluoromethyl)pyridine (260 mg), tetrakis-triphenylphosphine palladium (0) (23.1 mg), copper iodide (19.0 mg), triethylamine (8 ml) and benzene (2 ml) was heated to 100° C. After the reaction mixture was stirred for 3 h, it was kept standing to cool to room temperature, and thereto were added ethyl acetate and water. An insoluble material was filtrated, and then, the organic layer was separated. The organic layer was washed with a saturated saline and dried with anhydrous sodium sulfate. The organic layer was filtrated and concentrated, and then, the residue was purified by the silica gel column chromatography affording the compound 2 (78.9 mg).

MS m/z 283/285 [M+H]+, APCI(+)

A mixture of the compound 2 (40.0 mg), 3-amino-6-methoxypyridine (21.2 mg), acetic acid palladium (II) (1.6 mg), potassium-t-butoxide (47.8 mg), 1,3-bis(2,6-diisopropylphenyl)-imidazolium chloride (3.0 mg) and toluene (1 ml) was heated to 100° C. After 7 h, the reaction mixture was kept standing to cool to room temperature, and ethyl acetate and water were added thereto. After an insoluble material was filtrated, the organic layer was separated. The organic layer was washed with a saturated saline and dried with anhydrous sodium sulfate. After the organic layer was filtrated and concentrated, the residue was purified by the silica gel column chromatography affording the compound 3 (11.3 mg) was obtained.

MS m/z 370 [M+H]+, APCI(+)

Example 184

2-(5-fluoropyridin-2-yl)-1-(6-methoxypyridin-3-yl)-5-(trifluoromethyl)-1H-pyrrolo[2,3-b]pyridine

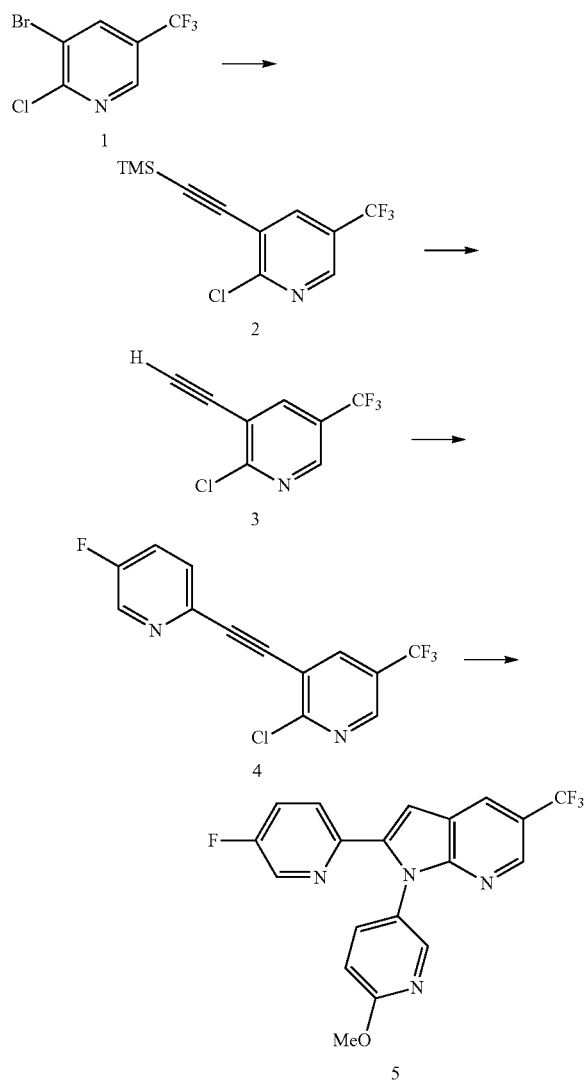

A mixture of 3-bromo-2-chloro-5-(trifluoromethyl)pyridine (260 mg), trimethylsilyl acetylene (98.2 mg), tetrakis-triphenylphosphine palladium (0) (23.1 mg), copper iodide (3.8 mg), triethylamine (4 ml) and benzene (1 ml) was heated to 60° C. After the reaction mixture was stirred all night and all day, it was kept standing to cool to room temperature, and the, the solvent was distilled off in vacuo. To the residue was added ethyl acetate, and the organic layer was separated. The organic layer was washed with a saturated saline, and dried with anhydrous sodium sulfate. Then, the organic layer was filtrated and concentrated, and the residue was purified by the silica gel column chromatography affording the compound 2 (226 mg). The compound 2 (224 mg) was dissolved in THF (2 ml), and thereto was added a HF solution (1M, 1.2 ml) of tetrabutylammonium fluoride at room temperature. After the reaction solution was stirred for 1 h, ethyl acetate and water were added thereto. The organic layer was separated, washed with a saturated saline, and dried with anhydrous sodium sulfate. After the organic layer was filtrated and concentrated, the residue was purified by the silica gel column chromatography affording the compound 3 (168 mg). A mixture of the compound 4 (164 mg), 2-bromo-5-fluoro-pyridine (168 mg), tetrakis-triphenylphosphine palladium (0) (18.4 mg), copper iodide (3.0 mg), triethylamine (4 ml) and benzene (1 ml) was heated to 100° C. After the reaction mixture was stirred for 5 h, it was kept standing to cool to room temperature, and then, the solvent was distilled off in vacuo. To the residue were added ethyl acetate and water, and then, an insoluble material was filtrated. After the organic layer was separated, it was washed with a saturated saline and dried with anhydrous sodium sulfate. After the organic layer was filtrated and concentrated, the residue was purified by the silica gel column chromatography affording the compound 4 (79.2 mg) was obtained.

MS m/z 301 [M+H]+, APCI(+)

A mixture of compound 4 (77.8 mg), 3-amino-6-methoxypyridine (38.6 mg), acetic acid palladium (II) (2.9 mg), potassium-t-butoxide (87.2 mg), 1,3-bis(2,6-diisopropylphenyl)-imidazolium chloride (5.5 mg) and toluene (1 ml) was heated to 100° C. After the reaction mixture was stirred for 6 h, it was kept standing to cool to room temperature, and thereto were added ethyl acetate and water. After the organic layer was separated, it was washed with a saturated saline and dried with anhydrous sodium sulfate. After the organic layer was filtrated and concentrated, the residue was purified by the silica gel column chromatography affording the compound 5 (37.6 mg).

MS m/z 389 [M+H]+, APCI(+)

Example 185

2-(5-fluoropyridin-2-yl)-3-(6-methoxypyridin-3-yl)-6-(trifluoromethyl)-2H-indazole

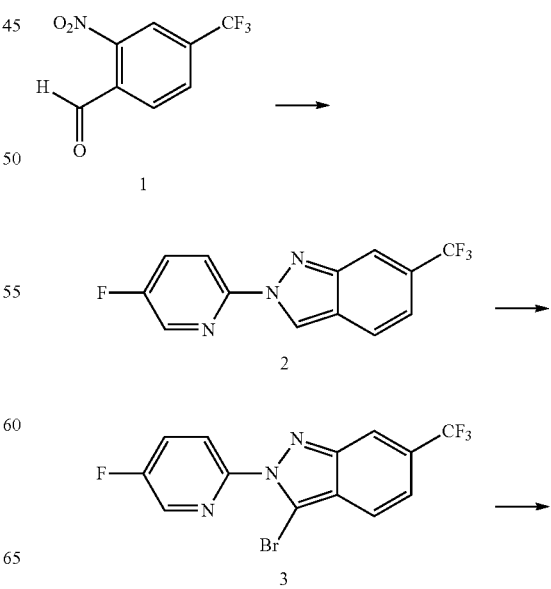

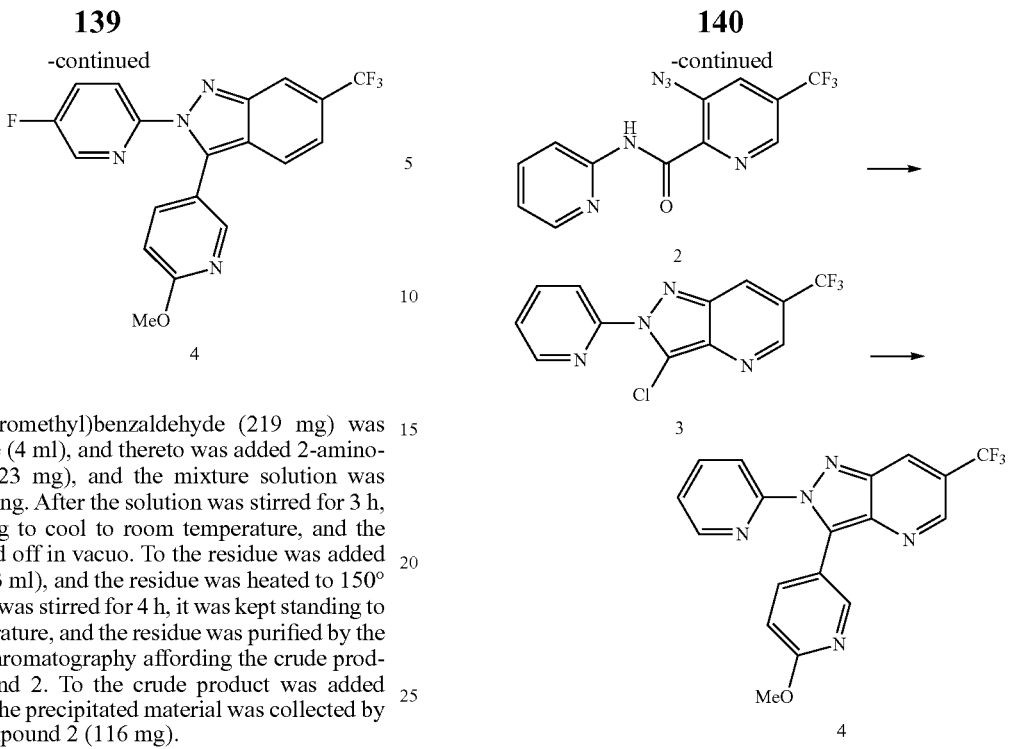

2-Nitro-4-(trifluoromethyl)benzaldehyde (219 mg) was dissolved in toluene (4 ml), and thereto was added 2-amino-5-fluoropyridine (123 mg), and the mixture solution was refluxed under heating. After the solution was stirred for 3 h, it was kept standing to cool to room temperature, and the solvent was distilled off in vacuo. To the residue was added triethyl phosphite (3 ml), and the residue was heated to 150° C. After the residue was stirred for 4 h, it was kept standing to cool to room temperature, and the residue was purified by the silica gel column chromatography affording the crude product of the compound 2. To the crude product was added hexane (2 ml), and the precipitated material was collected by filtration as the compound 2 (116 mg).

MS m/z 282 [M+H]+, APCI(+)

The compound 2 (116 mg) was dissolved in acetic acid (1 ml), and thereto was added bromine (21 μl), and followed by heating to 50° C. After the mixture solution was stirred for 1 h, thereto were added acetic acid (2 ml) and bromine (42 μl), and followed by heating to 80° C. After the reaction mixture was stirred all day and all night, thereto were added ethyl acetate, water and an aqueous solution saturated with sodium bicarbonate. The organic layer was separated, and then, the organic layer was washed sequentially with water and with a saturated saline, and successively dried with anhydrous sodium sulfate. After the organic layer was filtrated and concentrated, the residue was purified by the silica gel column chromatography affording the compound 3 (118 mg).

MS m/z 360/362 [M+H]+, APCI(+)

The compound 3 (114 mg) was dissolved in 1,4-dioxane (2 ml), and thereto were added 2-methoxy-5-pyridineboronic acid (72.8 mg), a palladium chloride 1,1'-ferrocene bisdiphenylphosphino ferrocene complex (11.6 mg) and potassium phosphate (101 mg), and followed by heating to 100° C. After the reaction mixture was stirred for 4 h, it was kept standing to cool to room temperature, and thereto were added ethyl acetate and water. After an insoluble material was filtrated, the organic layer was separated. The organic layer was washed with a saturated saline, and dried with anhydrous sodium sulfate. After the organic layer was filtrated and concentrated, the residue was purified by the silica gel column chromatography affording the compound 4 (108 mg).

MS m/z 389 [M+H]+, APCI(+)

Example 186

3-(6-methoxypyridin-3-yl)-2-pyridin-2-yl-6-(trifluoromethyl)-2H-pyrazolo[4,3-b]pyridine

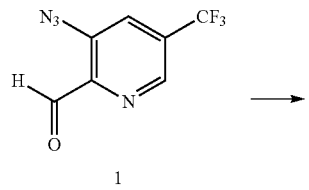

The compound 1 (165 mg) was dissolved in DMF (2 ml), and thereto were added HATU (324 mg), 2-aminopyridine (80.3 mg) and diisopropylethylamine (149 μl), and followed by stirring at room temperature all day and all night. To the reaction solution, were added ethyl acetate and water, and the organic layer was separated. The organic layer was washed sequentially with water and a saturated saline, and dried with anhydrous sodium sulfate. After the organic layer was filtrated and concentrated, the residue was purified by the silica gel column chromatography affording the compound 2 (208 mg).

MS m/z 309 [M+H]+, APCI(+)

The compound 2 (50.0 mg) was dissolved in thionyl chloride (1 ml), and the solution was refluxed for 7 h under heating. After the solution was kept standing to cool to room temperature, the solvent was distilled off in vacuo. To the residue were added ethyl acetate and an aqueous solution saturated sodium bicarbonate, then the organic layer was separated. The organic layer was washed with a saturated saline and dried with sodium sulfate. After the organic layer was filtrated and concentrated, the residue was purified by the silica gel column chromatography affording the compound 3 (11.2 mg).

MS m/z 299/301 [M+H]+, APCI(+)

The compound 3 (28.5 mg) was dissolved in 1,4-dioxane (1 ml), and thereto were added 2-methoxy-5-pyridineboronic acid (21.9 mg), a palladium chloride 1,1'-ferrocene bisdiphenylphosphino ferrocene complex (7.0 mg) and potassium phosphate (30.4 mg), and followed by heating to 100° C. After the mixture solution was stirred all day and all night, it was kept standing to cool to room temperature, and thereto were added ethyl acetate and water. After the organic layer was separated, the organic layer was washed with a saturated saline and dried with sodium sulfate. After the organic layer was filtrated and concentrated, the residue was purified by the silica gel column chromatography affording the compound 4 (20.5 mg).

MS m/z 389 [M+H]+, APCI(+)

TABLE 3

| Example | Structure | MS |
|---|---|---|
| Example 187 | 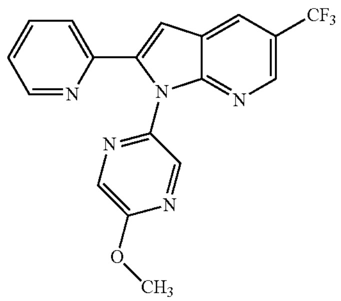 [SMILES: COc1cnc(-n2c(-c3ccccn3)cc3cc(C(F)(F)F)cnc32)cn1] | MS: 372 [M + H]+ APCI |
| Example 188 | 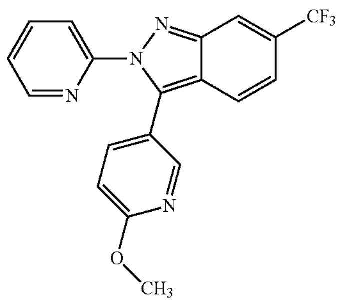 [SMILES: COc1ccc(-c2c3ccc(C(F)(F)F)cc3nn2-c2ccccn2)cn1] | MS: 371 [M + H]+ APCI |
| Example 189 | 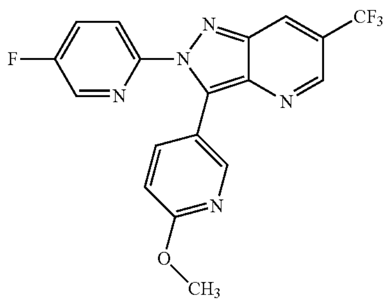 [SMILES: COc1ccc(-c2c3ncc(C(F)(F)F)cc3nn2-c2ccc(F)cn2)cn1] | MS: 390 [M + H]+ APCI |
| Example 190 | 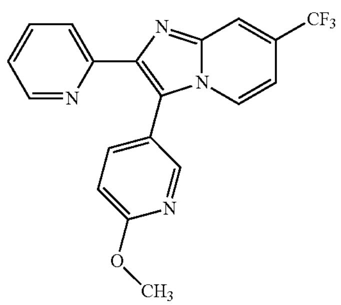 [SMILES: COc1ccc(-c2c(-c3ccccn3)nc3cc(C(F)(F)F)ccn23)cn1] | MS: 371 [M + H]+ APCI |
| Example 191 | 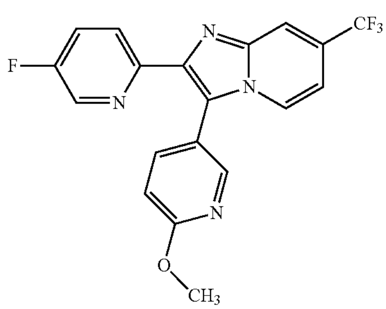 [SMILES: COc1ccc(-c2c(-c3ccc(F)cn3)nc3cc(C(F)(F)F)ccn23)cn1] | MS: 389 [M + H]+ APCI |

TABLE 3-continued

| Example | Structure | MS |
|---|---|---|
| Example 192 | 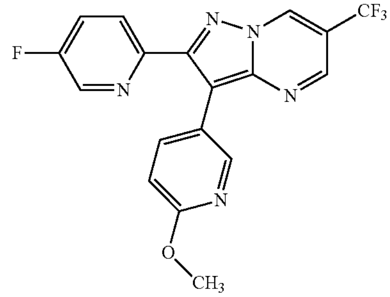 [SMILES: COc1ccc(-c2c(-c3ccc(F)cn3)nn3cc(C(F)(F)F)cnc23)cn1] | MS: 390 [M + H]+ APCI |

REFERENCE EXAMPLES

In the followings are explained specifically the synthetic intermediates of the compounds of the present invention. However, the scope of the present invention is not limited to the following Reference Examples.

Reference Example 1

$N^1$-(6-methoxypyridin-3-yl)-4-(trifluoromethyl)benzene-1,2-diamine

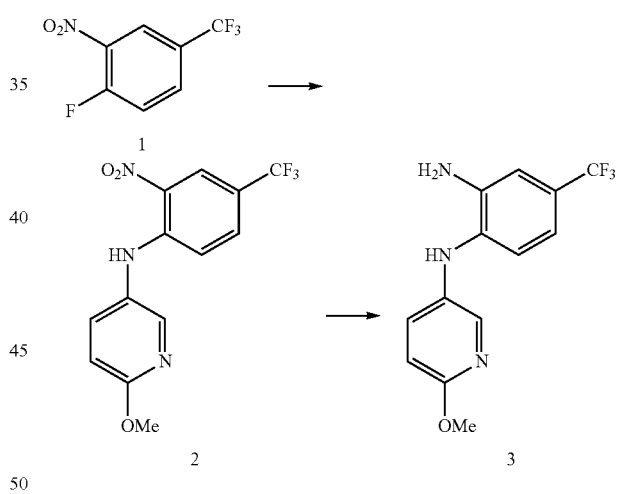

4-Fluoro-3-nitrobenzenetrifluoride (5.00 g) was dissolved in DMSO (25 ml), and thereto was added 5-amino-2-methoxypyridine (2.97 g), then followed by heating to 100° C. After the reaction mixture was stirred for 4 h, it was kept standing to cool to 0° C., and thereto were added water (75 ml) and an aqueous solution saturated sodium bicarbonate (25 ml). A precipitated solid was collected by filtration, and the compound 2 (7.11 g) was obtained. The obtained compound 2 (7.11 g) was suspended in ethanol (35 ml), and thereto was added a 10% palladium carbon (350 mg). The suspension was stirred at room temperature for 18 h under a hydrogen atmosphere. After an insoluble material was filtrated, the filtrate was concentrated affording the compound 3 (3.11 g).

MS m/z 284[M+H]+, APCI(+)

Reference Example 2

N$^1$-(6-methoxypyridazin-3-yl)-4-(trifluoromethyl)benzene-1,2-diamine

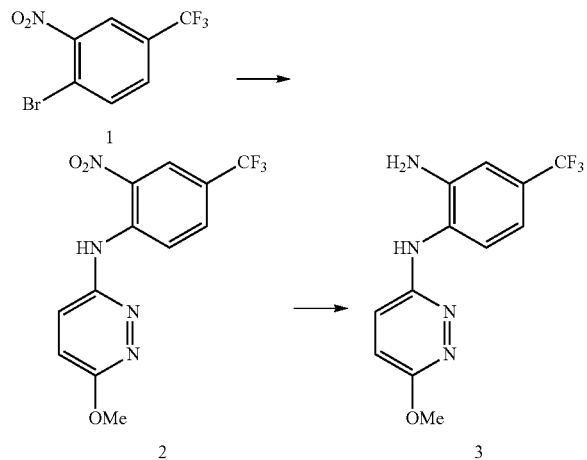

4-Bromo-3-nitrobenzotrifluoride (47.9 g) was dissolved in 1,2-dimethoxyethane (100 ml), and thereto were added 3-amino-6-methoxypyridazine (33.3 g), tris(dibenzylidene acetone)dipalladium (0) (8.10 g), 2-dicyclohexylphosphino-2',4',6'-triisopropylbiphenyl (6.97 g) and potassium phosphate (67.6 g), and followed by heating to 110° C. After the reaction mixture was stirred for 2 h, it was kept standing to cool to room temperature, then an insoluble material was filtrated. To the filtrate were added ethyl acetate (400 ml) and water (400 ml), then, the organic layer was separated. The organic layer was washed with a saturated saline and dried with anhydrous sodium sulfate. After the organic layer was filtrated and concentrated, ethanol (400 ml) was added to the residue, and the solution was stirred at 80° C. for 30 min. After the solution was kept standing to cool to room temperature, the compound 2 (36.3 g) was obtained by filtrating and collecting precipitates.

MS m/z 315 [M+H]+, APCI(+)

The compound 2 (40.0 g) was suspended in methanol (400 ml), and thereto were added iron (III) chloride (2.06 g), hydrazine monohydrate (39.7 g) and active carbon (4 g), then the reaction mixture was heated to 80° C. After the mixture was stirred for 2 h, it was kept standing to cool to room temperature, then, an insoluble material was filtrated and washed well with a chloroform:methanol=10:1 solution. After the filtrate was concentrated, chloroform (500 ml) was added thereto, and the solution was stirred all day and all night. A crude product (25.3 g) of the compound 3 was obtained by filtrating and collecting precipitates. The filtrate was also concentrated, and after the similar procedure above, a crude product (8.91 g) of the compound 3 was obtained. The obtained crude products were collected and dissolved in ethanol (250 ml) by heating. After the solution was kept standing to cool to room temperature, the compound 3 (29.3 g) was obtained by filtrating and collecting precipitates.

MS m/z 285 [M+H]+, APCI(+)

Reference Example 3

N$^1$-(6-methoxypyridazin-3-yl)-4-(trifluoromethoxy)benzene-1,2-diamine

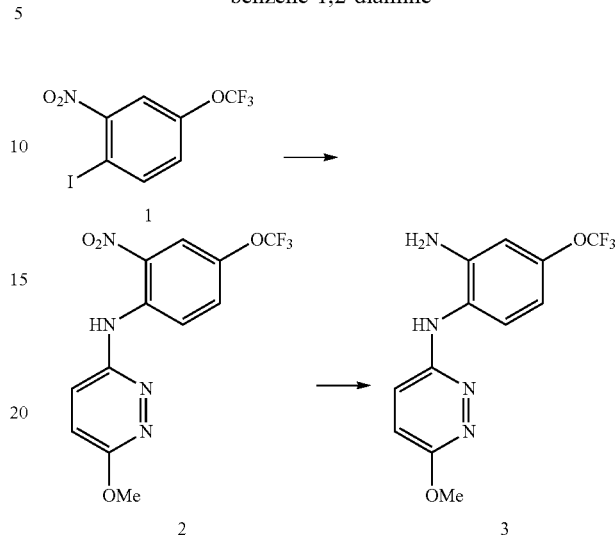

In toluene (20 ml) were suspended 2-nitro-4-(trifluoromethoxy)-iodobenzene (2.0 g), 3-amino-6-methoxypyridazine (1.88 g), N,N'-dimethylethylenediamine (106 mg), potassium phosphate (2.55 g) and copper iodide (114 mg), and the mixture was heated to 100° C. After the mixture was stirred all day and all night, it was kept standing to cool to room temperature, and ethyl acetate was added thereto. After the organic layer was separated, the organic layer was washed sequentially with water and a saturated saline, and then dried with magnesium sulfate. After the organic layer was filtrated and concentrated, the residue was purified by the silica gel column chromatography affording the compound 2 (0.899 g)

MS m/z 331 [M+H]+, APCI(+)

The compound 2 (0.899 g) was dissolved in methanol (14 ml), and thereto were added iron (III) chloride (88 mg), hydrazine monohydrate (681 mg) and active carbon (160 mg), then, the solution was refluxed for 2 h under heating. The solution was kept standing to cool to room temperature, and an insoluble material was filtrated. After the filtrate was concentrated, to the residue were added ethyl acetate, chloroform and water, then, the organic layer was separated. After the organic layer was concentrated, the residue was purified by the silica gel column chromatography affording the compound 3 (0.714 g).

MS m/z 301 [M+H]+, APCI(+)

Reference Example 4

N$^2$-(6-methoxypyridin-3-yl)-5-(trifluoromethyl)pyridin-2,3-diamine

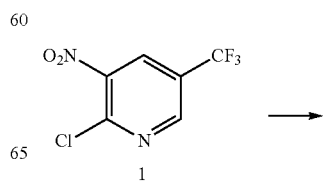

-continued

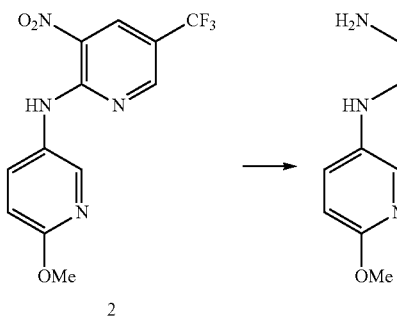

2-Chloro-3-nitro-5-(trifluoromethyl)pyridine (8.90 g) was dissolved in DMF (90 ml), and 5-amino-2-methoxypyridine (5.85 g) and potassium carbonate (6.51 g) were added thereto. After the mixture was stirred at room temperature all day and all night, water was added thereto, and the mixture was extracted with ethyl acetate. The organic layer was washed with a saturated saline and dried with sodium sulfate. After the organic layer was filtrated and concentrated, ethanol (50 ml) was added to dissolve the residue under heating. The solution was kept standing to cool to room temperature, and the compound 2 (10.9 g) was obtained by filtrating and collecting precipitates.

MS m/z 315 [M+H]+, APCI(+)

The compound 2 (11.5 g) was suspended in methanol (120 ml), and thereto were added iron (III) chloride (1.19 g), hydrazine monohydrate (9.16 g) and active carbon (1 g), and the mixture was heated to 100° C. After the mixture was stirred for 3 h, it was kept standing to cool to room temperature, and an insoluble material was filtrated and washed well with methanol. After the filtrate was concentrated, the residue was dissolved in ethyl acetate, washed sequentially with water and a saturated saline, and dried with anhydrous sodium sulfate. After the organic layer was filtrated and concentrated, ethyl acetate and n-heptane were added to the residue, and the compound 3 (10.9 g) was obtained by filtrating and collecting precipitates.

MS m/z 285 [M+H]+, APCI(+)

Reference Example 5

$N^2$-(5-methoxypyrazine-2-yl)-5-(trifluoromethyl)pyridin-2,3-diamine

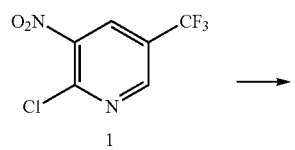

-continued

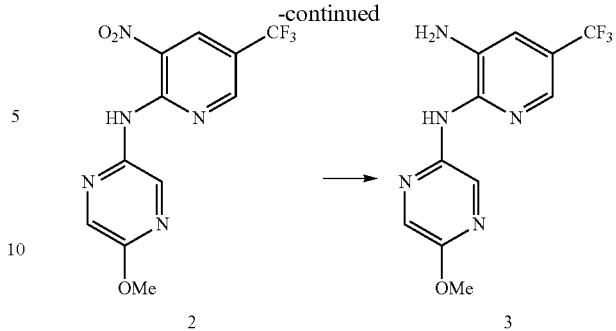

2-Chloro-3-nitro-5-(trifluoromethyl)pyridine (500 mg) was dissolved in 1,2-dimethoxyethane (7.4 ml), and thereto were added 5-methoxypyrazine-2-amine (414 mg), tris (dibenzylidene acetone)dipalladium (0) (101 mg), potassium phosphate (843 mg) and 2-dicyclohexylphosphino-2'-(N,N-dimethylamino)biphenyl (87 mg), and the mixture was heated to 100° C. After the mixture was stirred all day and all night, it was kept standing to cool to room temperature, and water and chloroform were added thereto. After an insoluble material was filtrated, the organic layer was separated. After the organic layer was concentrated, the residue was purified by the silica gel column chromatography affording the compound 2 (502 mg).

MS m/z 316[M+H]+, APCI(+)

The compound 2 (502 mg) was suspended in methanol (16 ml), and thereto were added active carbon (100 mg), iron (III) chloride (52 mg) and hydrazine monohydrate (0.39 mL), and the mixture was refluxed for 3 h under heating. After the mixture was kept standing to cool to room temperature, an insoluble material was filtrated and washed well with methanol. After the filtrate was concentrated, to the residue were added ethyl acetate, chloroform and water, then, the organic layer was separated. After the organic layer was concentrated, the residue was purified by the silica gel column chromatography affording the compound 3 (350 mg).

MS m/z 286 [M+H]+, APCI(+)

Reference Example 6

$N^2$-[6-(methoxyamino)pyridin-3-yl]-5-(trifluoromethyl)pyridin-2,3-diamine

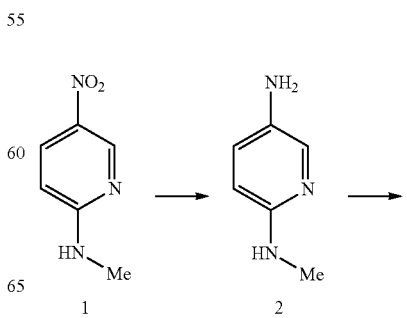

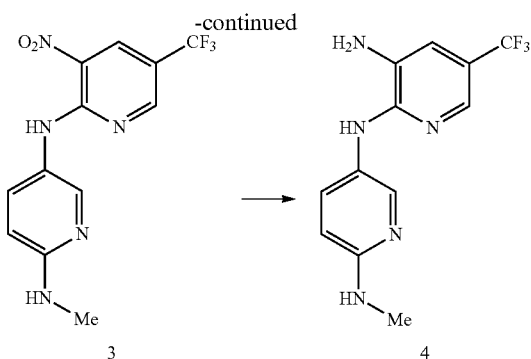

2-N-methylamino-5-nitropyridine (474 mg) was suspended in methanol (15.5 ml), and thereto were added active carbon (185 mg), iron (III) chloride (100 mg) and hydrazine monohydrate (0.75 ml), then, the mixture was refluxed for 4 h under heating. After the mixture was kept standing to cool to room temperature, an insoluble material was filtrated and washed well with methanol. After the filtrate was concentrated, to the residue were added ethyl acetate, chloroform, water, sodium chloride and potassium carbonate, the organic layer was separated. After the organic layer was concentrated, a mixture of the compound 2 was obtained. The obtained residue was dissolved in DMF (10.3 ml), 2-chloro-3-nitro-5-(trifluoromethyl)pyridine (701 mg) and potassium carbonate (513 mg) were added thereto at 0° C., and the mixture was stirred at room temperature all day and all night. Water was added to the reaction solution, and the reaction solution was extracted with ethyl acetate. The organic layer was washed with a saturated saline and dried with magnesium sulfate. After the organic layer was filtrated and concentrated, the residue was purified by the silica gel column chromatography affording the compound 3 (483 mg).

MS m/z 314 [M+H]+, APCI(+)

The compound 3 (483 mg) was dissolved in methanol (15 ml), and thereto were added active carbon (100 mg), iron (III) chloride (50 mg) and hydrazine monohydrate (0.37 ml), and the mixture was refluxed for 3 h under heating. After the mixture was kept standing to cool to room temperature, an insoluble material was filtrated and washed well with methanol. After the filtrate was concentrated, to the residue were added ethyl acetate, chloroform and water, and the organic layer was separated. After the organic layer was concentrated, the residue was purified by the silica gel column chromatography affording the compound 4 (173 mg).

MS m/z 284 [M+H]+, APCI(+)

Experimental Examples

1. Platelet Aggregation Inhibitory Activity

A blood of a guinea pig was sampled by using a 1/10 volume of a 3.8% sodium citrate as a platelet aggregation inhibitor, and a platelet rich plasma (PRP) was separated by centrifuging the blood sample at 1100 rpm for 10 min. After fractionating the PRP in the upper layer, the lower layer was centrifuged at 3000 rpm for 10 min to fractionate the platelet poor plasma (PPP). To 100 μL of PRP, a 1 μL solution of each compound was added, and after still standing at 37° C. for 1 min, the mixture was stirred at 37° C. for 1 min by a stirrer. Then, 11 μL of collagen, ristocetin, or ADP was added thereto to induce the platelet aggregation. The platelet aggregation ability was measured by using the mCM hematolaser 313M (L-M-S Inc.). Based on the assumption that a light transmittance of PPP corresponds to a 100% coagulation value, an aggregation rate at each concentration of the compound was determined, then, an $IC_{50}$ value was calculated therefrom.

[Platelet Aggregation Inhibitory Activities: Collagen-Induced Platelet Aggregation]

TABLE 4

|  | $IC_{50}$ μM |
|---|---|
| Example 1 | 0.033 |
| Example 2 | 0.18 |
| Example 3 | 0.032 |
| Example 4 | 0.021 |
| Example 5 | 0.089 |
| Example 6 | 0.257 |
| Example 7 | 0.025 |
| Example 8 | 0.15 |
| Example 9 | 0.15 |
| Example 10 | 0.018 |
| Example 11 | 0.13 |
| Example 12 | 0.23 |
| Example 13 | 0.042 |
| Example 14 | 0.2 |
| Example 15 | 0.28 |
| Example 17 | 0.11 |
| Example 18 | 0.49 |
| Example 19 | 10.4 |
| Example 20 | 0.062 |
| Example 21 | 0.13 |
| Example 23 | 4.47 |
| Example 24 | 0.05 |
| Example 27 | 0.19 |
| Example 31 | 0.25 |
| Example 35 | 0.044 |
| Example 36 | 0.049 |
| Example 37 | 2.38 |
| Example 40 | 0.33 |
| Example 49 | 15 |
| Example 52 | 0.054 |
| Example 53 | 0.057 |
| Example 54 | 0.19 |
| Example 55 | 0.084 |
| Example 56 | 0.047 |
| Example 58 | 0.17 |
| Example 62 | 0.017 |
| Example 67 | 0.17 |
| Example 71 | 0.078 |
| Example 72 | 0.18 |
| Example 73 | 0.08 |
| Example 75 | 0.2 |
| Example 81 | 0.22 |
| Example 88 | 0.12 |
| Example 89 | 0.053 |
| Example 90 | 0.06 |
| Example 94 | 0.19 |
| Example 107 | 0.066 |
| Example 108 | 0.21 |
| Example 109 | 0.095 |
| Example 110 | 0.13 |
| Example 118 | 0.24 |
| Example 122 | 0.034 |
| Example 125 | 0.029 |
| Example 126 | 0.194 |
| Example 130 | 0.177 |
| Example 139 | 0.06 |
| Example 144 | 0.03 |
| Example 145 | 0.074 |
| Example 146 | 0.078 |
| Example 147 | 0.026 |
| Example 148 | 0.081 |
| Example 149 | 0.23 |
| Example 150 | 0.205 |
| Example 151 | 0.024 |
| Example 152 | 0.086 |
| Example 153 | 0.291 |
| Example 154 | 0.129 |
| Example 155 | 0.029 |
| Example 156 | 0.076 |
| Example 157 | 0.074 |

TABLE 4-continued

| | IC$_{50}$ μM |
|---|---|
| Example 158 | 0.06 |
| Example 159 | 0.028 |
| Example 160 | 0.163 |
| Example 161 | 0.268 |
| Example 162 | 0.185 |
| Example 163 | 0.125 |
| Example 164 | 0.161 |
| Example 165 | 0.203 |
| Example 166 | 0.316 |
| Example 167 | 0.157 |
| Example 168 | 0.259 |
| Example 169 | 0.123 |
| Example 170 | 0.279 |
| Example 171 | 0.091 |
| Example 172 | 0.275 |
| Example 173 | 0.077 |
| Example 174 | 0.084 |
| Example 175 | 0.075 |
| Example 176 | 0.055 |
| Example 177 | 0.021 |
| Example 178 | 0.094 |
| Example 179 | 0.075 |
| Example 180 | 0.055 |
| Example 181 | 0.033 |
| Example 182 | 0.116 |
| Example 183 | 0.024 |
| Example 184 | 0.017 |
| Example 185 | 0.07 |
| Example 186 | 0.016 |
| Example 187 | 0.04 |
| Example 188 | 0.03 |
| Example 190 | 0.218 |
| Example 191 | 0.79 |
| Example 192 | 0.06 |

[Platelet Aggregation Inhibitory Activities: Ristocetin-Induced Platelet Aggregation]

TABLE 5

| | IC$_{50}$ μM |
|---|---|
| Example 1 | 0.1 |
| Example 2 | 0.092 |
| Example 3 | 0.032 |
| Example 4 | 0.024 |
| Example 7 | 0.06 |
| Example 8 | 0.095 |
| Example 9 | 0.14 |
| Example 10 | 0.015 |
| Example 11 | 0.057 |
| Example 12 | 0.19 |
| Example 13 | 0.041 |
| Example 15 | 0.15 |
| Example 17 | 0.16 |
| Example 18 | 0.12 |
| Example 20 | 0.21 |
| Example 21 | 0.39 |
| Example 24 | 0.13 |
| Example 27 | 0.17 |
| Example 31 | 0.87 |
| Example 36 | 0.18 |
| Example 40 | 0.17 |
| Example 52 | 0.041 |
| Example 53 | 0.042 |
| Example 54 | 0.1 |
| Example 55 | 0.06 |
| Example 56 | 0.028 |
| Example 58 | 0.28 |
| Example 62 | 0.027 |
| Example 67 | 0.23 |
| Example 71 | 0.043 |
| Example 72 | 0.13 |
| Example 73 | 0.083 |
| Example 75 | 0.38 |
| Example 81 | 0.5 |

TABLE 5-continued

| | IC$_{50}$ μM |
|---|---|
| Example 88 | 0.08 |
| Example 89 | 0.07 |
| Example 90 | 0.02 |
| Example 94 | 0.1 |
| Example 107 | 0.035 |
| Example 108 | 0.1 |
| Example 109 | 0.023 |
| Example 110 | 0.12 |
| Example 122 | 0.04 |
| Example 125 | 0.027 |
| Example 126 | 0.09 |
| Example 130 | 0.17 |
| Example 139 | 0.086 |
| Example 144 | 0.022 |
| Example 145 | 0.106 |
| Example 146 | 0.066 |
| Example 147 | 0.013 |
| Example 150 | 0.205 |
| Example 151 | 0.024 |
| Example 152 | 0.086 |
| Example 154 | 0.129 |
| Example 155 | 0.029 |
| Example 158 | 0.06 |
| Example 159 | 0.028 |
| Example 160 | 0.163 |
| Example 167 | 0.135 |
| Example 169 | 0.148 |
| Example 173 | 0.085 |
| Example 174 | 0.087 |
| Example 175 | 0.075 |
| Example 176 | 0.063 |
| Example 177 | 0.011 |
| Example 178 | 0.047 |
| Example 179 | 0.034 |
| Example 180 | 0.014 |
| Example 181 | 0.027 |
| Example 183 | 0.009 |
| Example 186 | 0.009 |
| Example 192 | 0.027 |

[Platelet Aggregation Inhibitory Activities: ADP-Induced Platelet Aggregation]

TABLE 6

| | IC$_{50}$ μM |
|---|---|
| Example 1 | >10 |
| Example 3 | >10 |
| Example 4 | >10 |
| Example 7 | >10 |
| Example 13 | >10 |
| Example 14 | >10 |
| Example 36 | >10 |
| Example 40 | >10 |
| Example 52 | >10 |
| Example 62 | >10 |
| Example 71 | >10 |
| Example 88 | >10 |
| Example 147 | >10 |
| Example 160 | >10 |
| Example 167 | >10 |
| Example 169 | >10 |
| Example 177 | >10 |
| Example 178 | >10 |
| Example 179 | >10 |
| Example 180 | >10 |
| Example 181 | >10 |
| Example 182 | >10 |
| Example 183 | >10 |
| Example 184 | >10 |
| Example 185 | >10 |
| Example 186 | >10 |
| Example 192 | >10 |

INDUSTRIAL APPLICABILITY

The specified heterocyclic derivatives of the present invention exhibit an antiplatelet action, and may be effective medicines for preventing or treating diseases related to the action.

The invention claimed is:
1. A compound of formula IIa:

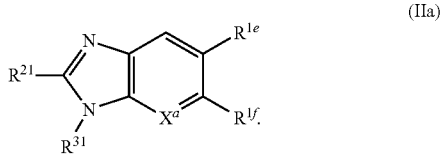

(IIa)

wherein:
$X^a$ is N or CH;
$R^{1e}$ is i) an alkyl optionally substituted with an aryl or a halogen, ii) an alkoxy optionally substituted with an aryl, a halogen, or a cycloalkyl, iii) an alkylthio optionally substituted with an aryl, a halogen, or a cycloalkyl, iv) an alkenyl, v) cyano, vi) a cycloalkyl, vii) a halogen, or viii) an amino optionally substituted with 1 or 2 alkyl;
$R^{1f}$ is hydrogen, an alkyl, an alkoxy, hydroxyl, cyano, or a halogen;
$R^{21}$ is pyrrolyl, imidazolyl, pyrazolyl, thiazolyl, isoxazolyl, oxazolyl, triazolyl, pyrazinyl, pyridazinyl, pyrimidyl, pyridyl, or quinolyl, each of which may be substituted with the same or different 1-3 substituents selected from the group consisting of an optionally substituted alkyl; an optionally substituted alkoxy; an optionally substituted alkylthio; an alkenyl; a halogen; cyano; a carbamoyl optionally substituted with 1 or 2 alkyl; an amino optionally substituted with 1 or 2 alkyl; hydroxyl; an alkanoyl; a cycloalkylcarbonyl; an arylcarbonyl; nitro; an optionally substituted aliphatic heteromonocyclic group; an aryl; and a heteroaryl, and
$R^{31}$ is pyridyl, pyrazinyl, pyrimidyl, or pyridazinyl, each of which may be substituted with the same or different 1-3 substituents selected from the group consisting of an optionally substituted alkyl; an optionally substituted alkoxy; an optionally substituted alkylthio; a cycloalkyl; an amino optionally substituted with 1 or 2 alkyl; an aliphatic heteromonocycle; and a halogen,
or a pharmaceutically acceptable salt thereof.

2. The compound of claim 1, wherein $R^{1e}$ is an alkyl substituted with a halogen or an alkoxy substituted with a halogen,
or a pharmaceutically acceptable salt thereof.

3. The compound of claim 1, wherein $R^{1e}$ is trifluoromethyl or trifluoromethoxy,
or a pharmaceutically acceptable salt thereof.

4. The compound of claim 1, wherein $R^{1f}$ is hydrogen,
or a pharmaceutically acceptable salt thereof.

5. The compound of claim 1, wherein $R^{21}$ is pyrrolyl, imidazolyl, pyrazolyl, thiazolyl, isoxazolyl, oxazolyl, triazolyl, pyrazinyl, pyridazinyl, pyrimidyl, pyridyl, or quinolyl, each of which may be substituted with the same or different 1-3 substituents selected from the group consisting of: an optionally substituted alkyl; an optionally substituted alkoxy; a halogen; cyano; a carbamoyl optionally substituted with 1 or 2 alkyl; an amino optionally substituted with 1 or 2 alkyl; hydroxyl; nitro; and an optionally substituted aliphatic hetero-monocyclic group,
or a pharmaceutically acceptable salt thereof.

6. The compound of claim 5, wherein $R^{21}$ is pyrrolyl, imidazolyl, pyrazolyl, thiazolyl, isoxazolyl, oxazolyl, triazolyl, pyrazinyl, pyridazinyl, pyrimidyl, pridyl, or quinolyl, each of which may be substituted with the same or different 1-3 substituents selected from the group consisting of an alkyl, an alkoxy, a halogen, cyano, a carbamoyl optionally substituted with 1 or 2 alkyl, and nitro,
or a pharmaceutically acceptable salt thereof.

7. The compound of claim 5, wherein $R^{21}$ is pyrrolyl, imidazolyl, pyrazolyl, thiazolyl, isoxazolyl, oxazolyl, triazolyl, pyrazinyl, pyridazinyl, pyrimidyl, pridyl, or quinolyl, each of which may be substituted with the same or different 1-3 substituents selected from the group consisting of an alkyl, a halogen, and cyano,
or a pharmaceutically acceptable salt thereof.

8. The compound of claim 1, wherein $R^{31}$ is pyridyl, pyrazinyl, pyrimidyl, or pyridazinyl, each of which may be substituted with the same or different 1-3 substituents selected from the group consisting of an alkyl, an alkoxy, a halogen, and an amino optionally substituted with 1 or 2 alkyl,
or a pharmaceutically acceptable salt thereof.

9. The compound of claim 1, wherein $X^a$ is N,
or a pharmaceutically acceptable salt thereof.

10. A compound selected from the group consisting of:
1-(6-methoxypyridazin-3-yl)-2-pyridin-2-yl-5-(trifluoromethyl)-1H-benzimidazole;
2-(6-fluoropyridin-2-yl)-1-(6-methoxypyridazin-3-yl)-5-(trifluoromethyl)-1H-benzimidazole;
1-(6-methoxypyridazin-3-yl)-2-pyridin-2-yl-5-(trifluoromethoxy)-1H-benzimidazole;
2-(5-fluoropyridin-2-yl)-3-(6-methoxypyridin-3-yl)-6-(trifluoromethyl)-3H-imidazo[4,5-b]pyridine;
N-methyl-5-[2-pyridin-2-yl-6-(trifluoromethyl)-3H-imidazo[4,5-b]pyridin-3-yl]pyridin-2-amine;
N,N-dimethyl-5-[2-pyridin-2-yl-6-(trifluoromethyl)-3H-imidazo[4,5-b]pyridin-3-yl]pyridin-2-amine;
6-[1-(6-methoxypyridazin-3-yl)-5-(trifluoromethyl)-1H-benzimidazole-2-yl]nicotinonitrile;
5-[3-(6-methoxypyridin-3-yl)-6-(trifluoromethyl)-3H-imidazo[4,5-b]pyridin-2-yl]pyrazine-2-carbonitrile;
2-(6-methoxypyridazin-3-yl)-1-(6-methoxypyridin-3-yl)-5-(trifluoromethyl)-1H-benzimidazole;
3-(6-methoxypyridin-3-yl)-2-(1H-pyrrol-2-yl)-6-(trifluoromethyl)-3H-imidazo[4,5-b]pyridine;
2-(1H-imidazol-4-yl)-3-(6-methoxypyridin-3-yl)-6-(trifluoromethyl)-3H-imidazo[4,5-b]pyridine;
1,2-dipyridin-2-yl-5-(trifluoromethyl)-1H-benzimidazole;
3-(6-methoxypyridin-3-yl)-2-pyridin-2-yl-6-(trifluoromethyl)-3H-imidazo[4,5-b]pyridine;
1-(6-methoxypyridin-3-yl)-2-pyridin-2-yl-5-(trifluoromethyl)-1H-benzimidazole;
1-(6-methoxypyridazin-3-yl)-2-(1-methyl-1H-pyrazol-4-yl)-5-(trifluoromethyl)-1H-benzimidazole;
5-ethyl-1-(6-methoxypyridin-3-yl)-2-pyridin-2-yl-1H-benzimidazole;
2-(5-bromopyridin-2-yl)-1-(6-methoxypyridin-3-yl)-5-(trifluoromethyl)-1H-benzimidazole;
2-(5-fluoropyridin-2-yl)-1-(6-methoxypyridin-3-yl)-5-(trifluoromethyl)-1H-benzimidazole;
1,2-bis(6-methoxypyridin-3-yl)-5-(trifluoromethyl)-1H-benzimidazole;
5-cyclopropyl-1-(6-methoxypyridin-3-yl)-2-pyridin-2-yl-1H-benzimidazole;
5-(cyclopropylmethoxy)-1-(6-methoxypyridin-3-yl)-2-pyridin-2-yl-1H-benzimidazole;

2-(5-bromopyridin-2-yl)-1-(6-methoxypyridazin-3-yl)-5-(trifluoromethyl)-1H-benzimidazole;
2-(5-chloropyridin-2-yl)-1-(6-methoxypyridin-3-yl)-5-(trifluoromethyl)-1H-benzimidazole;
1-(6-methoxypyridin-3-yl)-2-pyridin-2-yl-5-(trifluoromethoxy)-1H-benzimidazole;
1-(6-methoxypyridazin-3-yl)-2-(1-methyl-1H-pyrazol-3-yl)-5-(trifluoromethyl)-1H-benzimidazole;
1-(6-methoxypyridazin-3-yl)-2-(5-nitropyridin-2-yl)-5-(trifluoromethyl)-1H-benzimidazole;
1-(6-methoxypyridazin-3-yl)-2-(1,3-thiazol-2-yl)-5-(trifluoromethyl)-1H-benzimidazole;
6-chloro-1-(6-methoxypyridin-3-yl)-2-pyridin-2-yl-5-(trifluoromethyl)-1H-benzimidazole;
2-(5-ethylpyridin-2-yl)-1-(6-methoxypyridazin-3-yl)-5-(trifluoromethyl)-1H-benzimidazole;
1-(6-methoxypyridazin-3-yl)-2-(4-methylpyridin-2-yl)-5-(trifluoromethyl)-1H-benzimidazole;
2-(5-fluoropyridin-2-yl)-1-(6-methoxypyridazin-3-yl)-5-(trifluoromethyl)-1H-benzimidazole;
1-[6-(methylthio)pyridazin-3-yl]-2-pyridin-2-yl-5-(trifluoromethyl)-1H-benzimidazole;
2-(5-fluoropyridin-2-yl)-1-(6-methoxypyridin-3-yl)-5-(trifluoromethoxy)-1H-benzimidazole;
2-(5-methylisoxazol-3-yl)-1-(6-methoxypyridazin-3-yl)-5-(trifluoromethyl)-1H-benzimidazole;
3-(6-methoxypyridin-3-yl)-2-(1-methyl-1H-pyrazol-3-yl)-6-(trifluoromethyl)-3H-imidazo[4,5-b]pyridine;
2-(4-bromopyridin-2-yl)-1-(6-methoxypyridazin-3-yl)-5-(trifluoromethyl)-1H-benzimidazole;
2-[1-(6-methoxypyridazin-3-yl)-5-(trifluoromethyl)-1H-benzimidazole-2-yl]nicotinonitrile;
1-(6-methoxypyridazin-3-yl)-2-(1,3-oxazol-4-yl)-5-(trifluoromethyl)-1H-benzimidazole;
1-(6-methoxypyridazin-3-yl)-2-(1,3-thiazol-4-yl)-5-(trifluoromethyl)-1H-benzimidazole;
1-(6-methoxypyridazin-3-yl)-2-(5-methylpyrazine-2-yl)-5-(trifluoromethyl)-1H-benzimidazole;
1-(6-methoxypyridazin-3-yl)-2-(2-methyl-1,3-thiazol-4-yl)-5-(trifluoromethyl)-1H-benzimidazole;
3-(6-methoxypyridin-3-yl)-2-(1,3-oxazol-4-yl)-6-(trifluoromethyl)-3H-imidazo[4,5-b]pyridine;
3-(6-methoxypyridin-3-yl)-2-(5-methylisoxazol-3-yl)-6-(trifluoromethyl)-3H-imidazo[4,5-b]pyridine;
3-(6-methoxypyridin-3-yl)-2-(1,3-thiazol-4-yl)-6-(trifluoromethyl)-3H-imidazo[4,5-b]pyridine;
3-(6-methoxypyridin-3-yl)-2-(2-methyl-1,3-thiazol-4-yl)-6-(trifluoromethyl)-3H-imidazo[4,5-b]pyridine;
3-(6-methylpyridin-3-yl)-2-pyridin-2-yl-6-(trifluoromethyl)-3H-imidazo[4,5-b]pyridine;
3-(6-methoxypyridin-3-yl)-2-(2-methyl-1,3-oxazol-4-yl)-6-(trifluoromethyl)-3H-imidazo[4,5-b]pyridine;
3-(5-methoxypyrazine-2-yl)-2-pyridin-2-yl-6-(trifluoromethyl)-3H-imidazo[4,5-b]pyridine;
3-(6-methoxypyridin-3-yl)-2-(5-methyl-1,3-oxazol-4-yl)-6-(trifluoromethyl)-3H-imidazo[4,5-b]pyridine;
6-[3-(6-methylpyridin-3-yl)-6-(trifluoromethyl)-3H-imidazo[4,5-b]pyridin-2-yl]nicotinonitrile;
1-(6-methoxypyridazin-3-yl)-2-(2-methyl-1,3-oxazol-4-yl)-5-(trifluoromethyl)-1H-benzimidazole;
2-(5-fluoropyridin-2-yl)-3-(5-methoxypyrazine-2-yl)-6-(trifluoromethyl)-3H-imidazo[4,5-b]pyridine;
6-isopropoxy-3-(6-methoxypyridin-3-yl)-2-pyridin-2-yl-3H-imidazo[4,5-b]pyridine;
6-(difluoromethoxy)-3-(6-methoxypyridin-3-yl)-2-pyridin-2-yl-3H-imidazo[4,5-b]pyridine;
3-(6-methoxypyridin-3-yl)-2-pyridin-2-yl-6-(trifluoromethoxy)-3H-imidazo[4,5-b]pyridine;
3-(5-methoxypyrazine-2-yl)-2-(1,3-thiazol-4-yl)-6-(trifluoromethyl)-3H-imidazo[4,5-b]pyridine;
5-[2-(5-fluoropyridin-2-yl)-6-(trifluoromethyl)-3H-imidazo[4,5-b]pyridin-3-yl]-N-methylpyridin-2-amine;
6-{3-[6-(methylamino)pyridin-3-yl]-6-(trifluoromethyl)-3H-imidazo[4,5-b]pyridin-2-yl}nicotinonitrile;
3-(5-methoxypyrazine-2-yl)-2-(1,3-oxazol-4-yl)-6-(trifluoromethyl)-3H-imidazo[4,5-b]pyridine;
3-(5-methoxypyrazine-2-yl)-2-(2-methyl-1,3-oxazol-4-yl)-(trifluoromethyl)-3H-imidazo[4,5-b]pyridine;
3-(5-methoxypyrazine-2-yl)-2-(1-methyl-1H-pyrazol-3-yl)-6-(trifluoromethyl)-3H-imidazo[4,5-b]pyridine;
3-(5-methoxypyrazine-2-yl)-2-(5-methylisoxazol-3-yl)-6-(trifluoromethyl)-3H-imidazo[4,5-b]pyridine;
1-(6-methoxypyridazin-3-yl)-2-(1,3-oxazol-4-yl)-5-(trifluoromethoxy)-1H-benzimidazole;
1-(6-methoxypyridazin-3-yl)-2-(1-methyl-1H-pyrazol-3-yl)-5-(trifluoromethoxy)-1H-benzimidazole;
5-[3-(5-methoxypyridazin-2-yl)-6-(trifluoromethyl)-3H-imidazo[4,5-b]pyridin-2-yl]pyrazine-2-carbonitrile;
1-(6-methoxypyridazin-3-yl)-2-(2-methyl-1,3-oxazol-4-yl)-5-(trifluoromethoxy)-1H-benzimidazole;
2-(5-chloropyridin-2-yl)-3-(6-methoxypyridin-3-yl)-6-(trifluoromethyl)-3H-imidazo[4,5-b]pyridine;
3-(6-methoxypyridin-3-yl)-2-(1-methyl-1H-1,2,3-triazol-4-yl)-6-(trifluoromethyl)-3H-imidazo[4,5-b]pyridine;
1-(5-methoxypyrazine-2-yl)-2-pyridin-2-yl-5-(trifluoromethyl)-1H-benzimidazole;
3-(6-methoxypyridin-3-yl)-2-(1-methyl-1H-pyrazol-3-yl)-6-(trifluoromethyl)-3H-imidazo[4,5-b]pyridine;
1-(6-methoxypyridazin-3-yl)-2-(1-methyl-1H-1,2,3-triazol-4-yl)-5-(trifluoromethyl)-1H-benzimidazole;
3-(5-methoxypyrazine-2-yl)-2-(1-methyl-1H-1,2,3-triazol-4-yl)-6-(trifluoromethyl)-3H-imidazo[4,5-b]pyridine;
3-(5-methoxypyrazine-2-yl)-2-(1-methyl-1H-pyrazol-4-yl)-6-(trifluoromethyl)-3H-imidazo[4,5-b]pyridine;
1-(6-methoxypyridazin-3-yl)-2-(1-methyl-1H-pyrazol-4-yl)-5-(trifluoromethoxy)-1H-benzimidazole;
1-(6-methoxypyridazin-3-yl)-2-(1-methyl-1H-1,2,3-triazol-4-yl)-5-(trifluoromethoxy)-1H-benzimidazole;
1-(6-methoxypyridazin-3-yl)-2-(5-methylisoxazol-3-yl)-5-(trifluoromethoxy)-1H-benzimidazole;
3-(5-methoxypyrazine-2-yl)-2-(1-methyl-1H-imidazol-4-yl)-6-(trifluoromethyl)-3H-imidazo[4,5-b]pyridine;
6-ethoxy-3-(6-methoxypyridin-3-yl)-2-pyridin-2-yl-3H-imidazo[4,5-b]pyridine;
6-(cyclopropylmethoxy)-3-(6-methoxypyridin-3-yl)-2-pyridin-2-yl-3H-imidazo[4,5-b]pyridine;
2-(2-ethyl-1,3-oxazol-4-yl)-3-(6-methoxypyridin-3-yl)-6-(trifluoromethyl)-3H-imidazo[4,5-b]pyridine;
3-(6-methoxypyridin-3-yl)-6-propoxy-2-pyridin-2-yl-3H-imidazo[4,5-b]pyridine;
6-isobuthoxy-3-(6-methoxypyridin-3-yl)-2-pyridin-2-yl-3H-imidazo[4,5-b]pyridine;
3-(6-methoxypyridin-3-yl)-2-pyridin-2-yl-6-(2,2,2-trifluoroethoxy)-3H-imidazo[4,5-b]pyridine;
3-(6-methoxypyridin-3-yl)-2-pyridin-2-yl-6-(2,2,2-trifluoro-1-methylethoxy)-3H-imidazo[4,5-b]pyridine;
2-(5-fluoropyridin-2-yl)-3-(6-methoxypyridin-3-yl)-6-(trifluoromethoxy)-3H-imidazo[4,5-b]pyridine;
6-(difluoromethoxy)-2-(5-fluoropyridin-2-yl)-3-(6-methoxypyridin-3-yl)-3H-imidazo[4,5-b]pyridine;
2-(5-fluoropyridin-2-yl)-3-(6-methoxypyridin-3-yl)-6-(trifluoromethyl)pyrazolo[1,5-a]pyrimidine,
or a pharmaceutically acceptable salt thereof.

11. A pharmaceutical composition, comprising an active ingredient comprising the compound of claim 1, or a pharmaceutically acceptable salt thereof.

12. A medicine, comprising:
an active ingredient comprising the compound of claim 1 or a pharmaceutically acceptable salt thereof; and
a pharmaceutically acceptable additive.

13. The compound of claim 1, wherein
$R^{1e}$ is trifluoromethyl or trifluoromethoxy,
$R^{1f}$ is hydrogen,
$R^{21}$ is pyridyl or pyrazinyl, each of which may be substituted with the same or different 1-3 substituents selected from the group consisting of an alkyl, a halogen, and cyano,
$R^{31}$ is pyridyl or pyrazinyl, each of which may be substituted with the same or different 1-3 substituents selected from the group consisting of an alkyl, an alkoxy, a halogen, and an amino optionally substituted with 1 or 2 alkyl, and
$X^a$ is N,
or a pharmaceutically acceptable salt thereof.

14. A pharmaceutical composition, comprising an active ingredient comprising the compound of claim 10, or a pharmaceutically acceptable salt thereof.

15. A medicine, comprising:
an active ingredient comprising the compound of claim 10 or a pharmaceutically acceptable salt thereof and
a pharmaceutically acceptable additive.

16. A pharmaceutical composition, comprising an active ingredient comprising the compound of claim 13, or a pharmaceutically acceptable salt thereof.

17. A medicine, comprising:
an active ingredient comprising the compound of claim 13 or a pharmaceutically acceptable salt thereof; and
a pharmaceutically acceptable additive.

* * * * *

UNITED STATES PATENT AND TRADEMARK OFFICE
CERTIFICATE OF CORRECTION

PATENT NO. : 8,703,760 B2  
APPLICATION NO. : 13/516952  
DATED : April 22, 2014  
INVENTOR(S) : Hiroshi Sato et al.

Page 1 of 1

It is certified that error appears in the above-identified patent and that said Letters Patent is hereby corrected as shown below:

In the Claims

Column 154, lines 61-66, claim 10:

"2-(5-fluoropyridin-2-yl)-3-(6-methoxypyridin-3-yl)-6-(trifluoromethoxy)-3H-imidazo[4,5-b]pyridine; 6-(difluoromethoxy-2-(5-fluoropyridin-2-yl)-3-(6-methoxypyridin-3-yl)-3H-imidazo[4,5-b]pyridine; 2-(5-fluoropyridin-2-yl)-3-(6-methoxypyridin-3-yl)-6-(trifluoromethyl)pyrazolo[1,5-a]pyrimidine," is DELETED and in its place
--2-(5-fluoropyridin-2-yl)-3-(6-methoxypyridin-3-yl)-6-(trifluoromethoxy)-3H-imidazo[4,5-b]pyridine; and 6-(difluoromethoxy)-2-(5-fluoropyridin-2-yl)-3-(6-methoxypyridin-3-yl)-3H-imidazo[4,5-b]pyridine,-- is INSERTED Signed and Sealed this
Twenty-third Day of December, 2014

Michelle K. Lee
*Deputy Director of the United States Patent and Trademark Office*